United States Patent
Fischer et al.

[11] Patent Number: 5,610,122
[45] Date of Patent: Mar. 11, 1997

[54] 3-ARYL-4-HYDROXY-DELTA3-DIHYDRO-FURANONE DERIVATIVES

[75] Inventors: Reiner Fischer, Monheim; Thomas Bretschneider, Lohmar; Bernd-Wieland Krüger, Bergisch Gladbach; Hans-Joachim Santel; Markus Dollinger, both of Leverkusen; Ulrike Wachendorff-Neumann, Monheim; Christoph Erdelen, Leichlingen, all of Germany

[73] Assignee: Bayer Aktiengesellschaft, Leverkusen, Germany

[21] Appl. No.: 303,987

[22] Filed: Sep. 9, 1994

[30] Foreign Application Priority Data

Sep. 17, 1993 [DE] Germany .......................... 43 31 672.7
Nov. 5, 1993 [DE] Germany .......................... 43 37 853.6

[51] Int. Cl.$^6$ .................................. A01N 43/08
[52] U.S. Cl. ..................... 504/251; 504/299; 514/336; 514/462; 514/473; 546/15; 546/284.4; 549/315; 549/318; 549/220; 549/222
[58] Field of Search .................................. 549/315, 318; 514/462, 473, 336; 546/268; 504/251, 299

[56] References Cited

U.S. PATENT DOCUMENTS 4,525,201  6/1985  Kollmeyer et al. .......................... 71/76
5,262,383  11/1993  Fischer et al. .......................... 504/195

FOREIGN PATENT DOCUMENTS 0528156  2/1993  European Pat. Off. .

Primary Examiner—Amelia A. Owens
Attorney, Agent, or Firm—Sprung Horn Kramer & Woods

[57] ABSTRACT

The present invention relates to a new 3-aryl-4-hydroxy-$\Delta^3$-dihydrofuranone derivatives of the general formula (I)

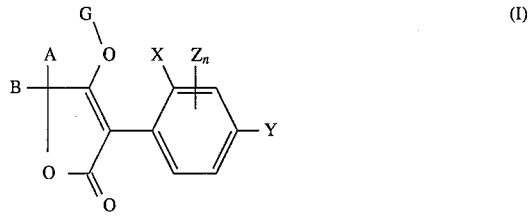

in which the radicals A, B, G, X, Y, Z and n have the meaning given in the description, to a plurality of processes for their preparation, and to their use as pesticides.

14 Claims, No Drawings

3-ARYL-4-HYDROXY-DELTA3-DIHYDROFURANONE DERIVATIVES

The present invention relates to new 3-aryl-4-hydroxy-$\Delta^3$-dihydrofuranone derivatives, to processes for their preparation and to their use as pesticides.

It has been disclosed that certain substituted $\Delta^3$-dihydrofuran-2-one derivatives have herbicidal properties (cf. DE-A 4,014,420). DE-A 4,014,420 also describes the synthesis of the tetronic acid derivatives used as starting compounds (such as, for example, 3-(2-methylphenyl)-4-hydroxy-5-(4-fluorophenyl)-$\Delta^3$-dihydrofuran-2-one). Compounds which have a similar structure are known from the publication Campbell et al., J. Chem. Soc., Perkin Trans. 1 1985, (8) 1567–76, but no insecticidal and/or acaricidal activity is indicated. Furthermore, EP 528,156 discloses 3-aryl-$\Delta^3$-dihydrofuranone derivatives having herbicidal, acaricidal and insecticidal properties, but the activity described therein is not always sufficient.

New 3-aryl-4-hydroxy-$\Delta^3$-dihydrofuranone derivatives of the formula (I)

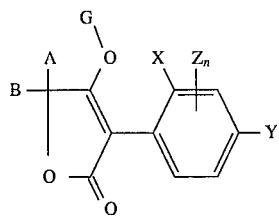

in which

X represents alkyl, halogen, alkoxy or halogenoalkyl,

Y represents hydrogen, alkyl, halogen, alkoxy or halogenoalkyl,

Z represents alkyl, halogen or alkoxy, n represents a number from 0–3, or in which the radicals X and Z together with the phenyl radical to which they are bonded form the naphthalene radical of the formula

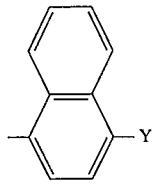

in which Y has the abovementioned meaning,

G represents hydrogen (a) or the groups

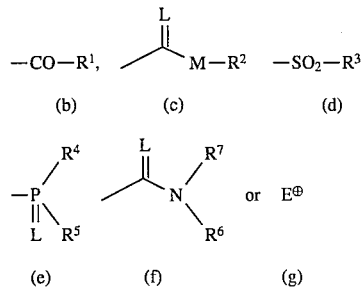

A and B together with the carbon atom to which they are bonded form a cycle which is substituted by alkoxy, alkylthio, alkylsulphoxyl, alkylsulphonyl, carboxyl or $CO_2^{R2}$ or A and B together with the carbon atom to which they are bonded represent a cycle in which two substituents together with the carbon atoms to which they are bonded represent a saturated cycle which is optionally substituted by alkyl, alkoxy or halogen and which can be interrupted by oxygen or sulphur, $E^\oplus$ represents a metal ion equivalent or an ammonium ion, L and M represent in each case oxygen or sulphur, $R^1$ represents in each case optionally substituted alkyl, alkenyl, alkoxyalkyl, alkylthioalkyl, polyalkoxyalkyl or cycloalkyl which can be interrupted by at least one hetero atom, in each case optionally substituted phenyl, phenylalkyl, hetaryl, phenoxyalkyl or hetaryloxyalkyl and $R^2$ represents alkyl, cycloalkyl, alkenyl, alkoxyalkyl or polyalkoxyalkyl, each of which is optionally substituted or represents in each case optionally substituted phenyl or benzyl, $R^3$, $R^4$ and $R^5$ independently of one another represent alkyl, alkoxy, alkylamino, dialkylamino, alkylthio, alkenylthio, alkinylthio or cycloalkylthio, each of which is optionally substituted by halogen, and in each case optionally substituted phenyl, phenoxy or phenylthio, $R^6$ and $R^7$ independently of one another represent hydrogen, or represent alkyl, alkenyl, alkoxy or alkoxyalkyl, each of which is optionally substituted by halogen, optionally substituted phenyl, optionally substituted benzyl, or in which $R^6$ and $R^7$ together represent an alkylene radical which is optionally interrupted by oxygen or sulphur, and the stereomerically and enantiomerically pure forms of compounds of the formula (1) have now been found.

Taking into account the various meanings (a), (b), (c), (d), (e), (f) and (g) of Group G of the general formula (I), the following main structures (Ia) to (Ig) result:

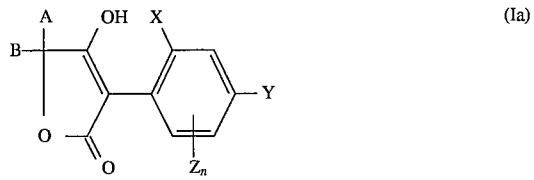
(Ia)

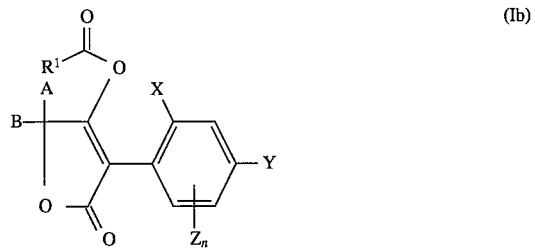
(Ib)

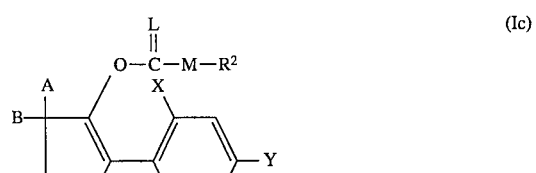
(Ic)

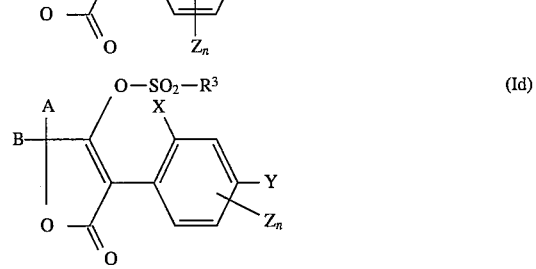
(Id)

-continued (Ie)

(If)

(Ig)

in which

A, B, E, L, M, X, Y, Z, $R^1$, $R^2$, $R^3$, $R^4$, $R^5$, $R^6$, $R^7$ and n have the abovementioned meanings.

Furthermore, it has been found that 3-aryl-4-hydroxy-$\Delta^3$-dihydrofuranone derivatives of the formula (Ia)

(Ia)

in which

A, B, X, Y, Z and n have the abovementioned meaning, are obtained when (A)

carboxylic esters of the formula (II)

(II)

in which

A, B, X, Y, Z and n have the abovementioned meaning and $R^8$ represents alkyl, are subjected to an intramolecular condensation reaction in the presence of a diluent and in the presence of a base.

(B)

Furthermore, it has been found that compounds of the formula (Ib)

(Ib)

in which

A, B, X, Y, Z, $R^1$ and n have the abovementioned meaning, are obtained when compounds of the formula (Ia)

(Ia)

in which

A, B, X, Y, Z and n have the abovementioned meaning,

α) are reacted with acid halides of the general formula (III)

$$\text{Hal}-\underset{\underset{O}{\|}}{C}-R^1 \qquad \text{(III)}$$

in which $R^1$ has the abovementioned meaning and

Hal represents halogen, in particular chlorine or bromine, if appropriate in the presence of a diluent, and if appropriate in the presence of an acid-binding agent, or β) are reacted with carboxylic anhydrides of the general formula (IV)

$$R^1-CO-O-CO-R^1 \qquad \text{(IV)}$$

in which $R^1$ has the abovementioned meaning, if appropriate in the presence of a diluent and if appropriate in the presence of an acid-binding agent.

(C)

Furthermore, it has been found that compounds of the formula (Ic)

(Ic)

in which

A, B, X, Y, Z, $R^2$ and n have the abovementioned meaning,

L represents oxygen and

M represents oxygen or sulphur, are obtained when compounds of the formula (Ia)

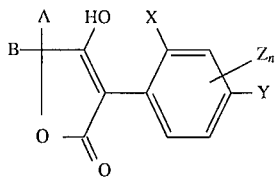 (Ia)

in which

A, B, X, Y, Z and n have the abovementioned meaning, are reacted with chloroformic esters or chloroformic thioesters of the general formula (V)

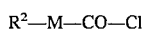 (V)

$R^2$—M—CO—Cl in which $R^2$ and M have the abovementioned meaning, if appropriate in the presence of a diluent and if appropriate in the presence of an acid-binding agent.

(D) Furthermore, it has been found that compounds of the formula (Ic)

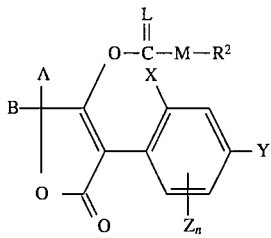 (Ic)

in which

A, B, $R^2$, X, Y, Z and n have the abovementioned meaning,

L represents sulphur
and

M represents oxygen or sulphur,
are obtained when compounds of the formula (Ia)

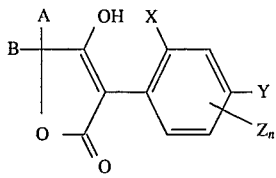 (Ia)

in which

A, B, X, Y, Z and n have the abovementioned meaning are reacted with chloromonothioformic esters or chlorodithioformic esters of the general formula (VI)

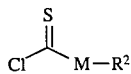 (VI)

in which

M and $R^2$ have the abovementioned meaning,
if appropriate in the presence of a diluent and if appropriate in the presence of an acid-binding agent.

(E) Furthermore, it has been found that compounds of the formula (Id)

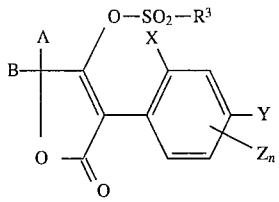 (Id)

in which

A, B, X, Y, Z, $R^3$ and n have the abovementioned meaning, are obtained when compounds of the formula (Ia)

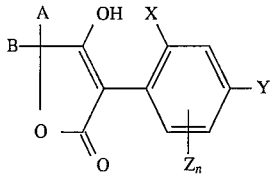 (Ia)

in which

A, B, X, Y, Z and n have the abovementioned meaning, are reacted with sulphonyl chlorides of the general formula (VII)

 (VII)

$R^3$—$SO_2$—Cl in which $R^3$ has the abovementioned meaning, if appropriate in the presence of a diluent and if appropriate in the presence of an acid-binding agent.

(F) Furthermore, it has been found that compounds of the formula (Ie)

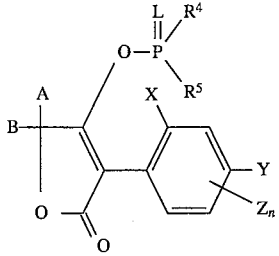 (Ie)

in which

A, B, L, X, Y, Z, $R^4$, $R^5$ and n have the abovementioned meaning,
are obtained when
compounds of the formula (Ia)

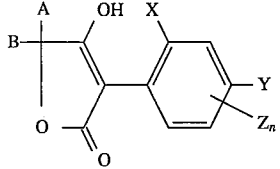 (Ia)

in which

A, B, X, Y, Z and n have the abovementioned meaning are reacted with phosphorus compounds of the general formula (IX)

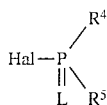

(VIII)

in which

L, $R^4$ and $R^5$ have the abovementioned meaning and

Hal represents halogen, in particular chlorine or bromine, if appropriate in the presence of a diluent and if appropriate in the presence of an acid-binding agent.

(G) Furthermore, it has been found that compounds of the formula (If)

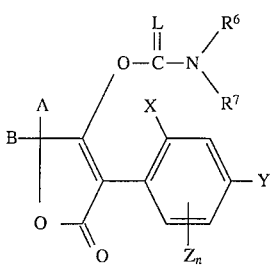

(If)

in which

A, B, L, X, Y, Z, $R^6$, $R^7$ and n have the abovementioned meaning, are obtained when compounds of the formula (Ia)

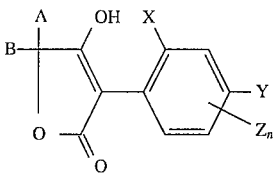

(Ia)

in which

A, B, X, Y, Z and n have the abovementioned meaning

α) are reacted with isocyanates of the general formula (IX)

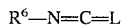

(IX)

in which

L and $R^6$ have the abovementioned meaning, if appropriate in the presence of a diluent and if appropriate in the presence of a catalyst, or β) are reacted with carbamoyl chlorides or thiocarbamoyl chlorides of the general formula (X)

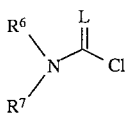

(X)

in which

L, $R^6$ and $R^7$ have the abovementioned meaning, if appropriate in the presence of a diluent and if appropriate in the presence of an acid-binding agent.

H) Furthermore, it has been found that compounds of the formula (Ig)

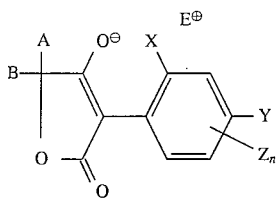

(Ig)

in which

X, Y, Z, A, B and n have the abovementioned meaning, and $E^\oplus$ represents a metal ion equivalent or an ammonium ion, are obtained when compounds of the formula (Ia)

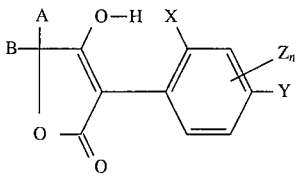

(Ia)

in which

X, Y, Z, A, B and n have the abovementioned meaning, are reacted with metal compounds or amines of the general formulae (XI) and (XII)

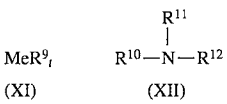

in which

Me represents mono- or divalent metal ions, t represents the number 1 or 2, $R^9$ represents hydrogen, hydroxy or alkoxy and $R^{10}$, $R^{11}$, and $R^{12}$ independently of one another represent hydrogen or alkyl, if appropriate in the presence of a diluent.

Furthermore, it has been found that the new 3-aryl-4-hydroxy-Δ³-dihydrofuranone derivatives of the formula (I) are distinguished by outstanding acaricidal, insecticidal and herbicidal activities, which makes them suitable for use as pesticides.

Preferred compounds of the formula (I) are those in which

X represents $C_1$–$C_6$-alkyl, halogen, $C_1$–$C_6$-alkoxy or $C_1$–$C_3$-halogenoalkyl, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number from 0 to 3, or in which the radicals X and Z together with the phenyl radical to which they are bonded form the naphthalene radical of the formula

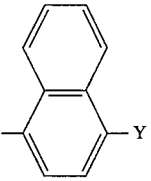

in which Y has the abovementioned meaning, or in which

A and B together with the carbon atom to which they are bonded form a saturated or unsaturated 3- to 8-membered ring which is substituted by $C_1-C_6$-alkoxy, $C_1-C_4$-alkylthio, $C_1-C_4$-alkylsulphoxyl or $C_1-C_4$-alkylsulphonyl, carboxyl or $CO_2R^2$ or A and B together with the carbon atom to which they are bonded represent a $C_3-C_8$-membered ring in which two substituents together with the carbon atoms to which they are bonded represent a saturated $C_5-C_7$-ring which is optionally substituted by $C_1-C_6$-alkyl, $C_1-C_6$-alkoxy or halogen and which can be interrupted by oxygen or sulphur, G represents hydrogen (a) or the groups

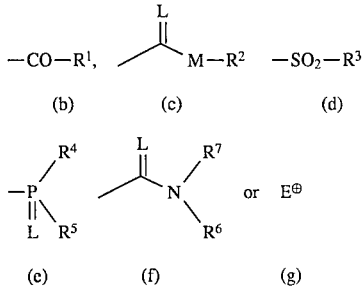

(b)   (c)   (d)

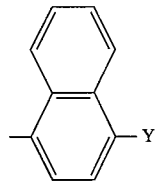 or $E^\oplus$ (e)   (f)   (g)

in which $E^\oplus$ represents a metal ion equivalent or an ammonium ion,

L and M in each case represent oxygen or sulphur, $R^1$ represents in each case optionally halogen-substituted $C_1-C_{20}$-alkyl, $C_2-C_{20}$-alkenyl, $C_1-C_8$-alkoxy-$C_1-C_8$-alkyl, $C_1-C_8$-alkylthio-$C_1-C_8$-alkyl, $C_1-C_8$-polyalkoxy-$C_1-C_8$-alkyl or $C_3-C_8$-cycloalkyl, which is optionally substituted by halogen or $C_1-C_6$-alkyl and which can be interrupted by at least one oxygen and/or sulphur atom, phenyl which is optionally substituted by halogen, nitro, $C_1-C_6$-alkyl, $C_1-C_6$-alkoxy, $C_1-C_6$-halogenoalkyl or $C_1-C_6$-halogenoalkoxy, phenyl-$C_1-C_6$-alkyl which is optionally substituted by halogen, $C_1-C_6$-alkyl, $C_1-C_6$-alkoxy, $C_1-C_6$-halogenoalkyl or $C_1-C_6$-halogenoalkoxy, hetaryl which is optionally substituted by halogen and/or $C_1-C_6$-alkyl, phenoxy-$C_1-C_6$-alkyl which is optionally substituted by halogen and/or $C_1-C_6$-alkyl, hetaryloxy-$C_1-C_6$-alkyl which is optionally substituted by halogen, amino and/or $C_1-C_6$-alkyl, $R^2$ represents $C_1-C_{20}$-alkyl, $C_3-C_{20}$-alkenyl, $C_1-C_6$-alkoxy-$C_2-C_8$-alkyl or $C_1-C_8$-polyalkoxy-$C_2-C_8$-alkyl, each of which is optionally substituted by halogen, $C_3-C_8$-cycloalkyl, which is optionally substituted by halogen or $C_1-C_6$-alkyl, phenyl or benzyl, each of which is optionally substituted by halogen, nitro, $C_1-C_6$-alkyl, $C_1-C_6$-alkoxy or $C_1-C_6$-halogenalkyl, $R^3$, $R^4$ and $R^5$ independently of one another represent $C_1-C_8$-alkyl, $C_1-C_8$-alkoxy, $C_1-C_8$-alkylamino, di-($C_1-C_8$-alkylamino, $C_1-C_8$-alkylthio, $C_2-C_5$-alkenylthio, $C_2-C_5$-alkinylthio or $C_3-C_7$-cycloalkylthio, each of which is optionally substituted by halogen, or represent phenyl, phenoxy or phenylthio, each of which is optionally substituted by halogen, nitro, cyano, $C_1-C_4$-alkoxy, $C_1-C_4$-halogenoalkoxy, $C_1-C_4$-alkylthio, $C_1-C_4$-halogenoalkylthio, $C_1-C_4$-alkyl or $C_1-C_4$-halogenoalkyl, $R^6$ and $R^7$ independently of one another represent hydrogen or represent $C_1-C_{20}$-alkyl, $C_1-C_{20}$-alkoxy, $C_3-C_8$-alkenyl or $C_1-C_{20}$-alkoxy-$C_1-C_{20}$-alkyl, each of which is optionally substituted by halogen, phenyl which is optionally substituted by halogen, $C_1-C_{20}$-halogenoalkyl, $C_1-C_{20}$-alkyl or $C_1-C_{20}$-alkoxy, benzyl which is optionally substituted by halogen, $C_1-C_{20}$-alkyl, $C_1-C_{20}$-halogenoalkyl or $C_1-C_{20}$-alkoxy, or together represent a $C_4-C_6$-alkylene ring which is optionally interrupted by oxygen or sulphur, and the stereomerically and enantiomerically pure forms of compounds of the formula (I).

Particularly preferred compounds of the formula (I) are those in which

X represents $C_1-C_6$-alkyl, halogen, $C_1-C_6$-alkoxy or $C_1-C_2$-halogenoalkyl, Y represents hydrogen, $C_1-C_6$-alkyl, halogen, $C_1-C_6$-alkoxy or $C_1-C_2$-halogenoalkyl, Z represents $C_1-C_4$-alkyl, halogen or $C_1-C_4$-alkoxy, n represents a number from 0 to 2, or in which the radicals X and Z together with the phenyl radical to which they are bonded form the naphthalene radical of the formula

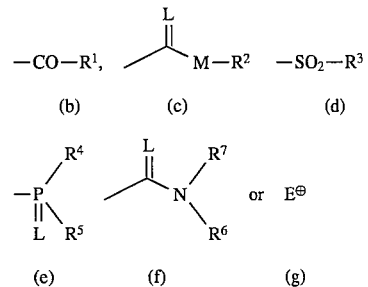

in which Y has the abovementioned meaning,

A and B together with the carbon atom to which they are bonded form saturated or unsaturated, 5- to 7-membered ring which is substituted by $C_1-C_5$-alkoxy, $C_1-C_3$-alkylthio, $C_1-C_3$-alkylsulphoxyl or $C_1-C_3$-alkylsulphonyl, carboxyl or 2 or $CO_2R^2$ or A and B together with the carbon atom to which they are bonded represent a $C_4-C_7$-membered ring in which two substituents together with the carbon atoms to which they are bonded represent a saturated $C_5-C_6$-ring which is optionally substituted by $C_1-C_3$-alkyl, $C_1-C_3$-alkoxy, fluorine or chlorine and which can be interrupted by oxygen or sulphur, G represents hydrogen (a) or the groups $-CO-R^1$,   $M-R^2$   $-SO_2-R^3$ (b)   (c)   (d)

or $E^\oplus$ (e)   (f)   (g)

in which $E^\oplus$ represents a metal ion equivalent or an ammonium ion,

L and M in each case represent oxygen or sulphur, $R^1$ represents in each case optionally halogen-substituted $C_1-C_{16}$-alkyl, $C_2-C_{16}$-alkenyl, $C_1-C_6$-alkoxy-$C_1-C_6$-alkyl, $C_1-C_6$-alkylthio-$C_1-C_6$-alkyl, $C_1-C_6$-polyalkoxy-$C_1-C_6$-alkyl or $C_{3-C7}$-cycloalkyl, which is optionally substituted by chlorine or $C_1-C_4$-alkyl and which can be interrupted by 1–2 oxygen and/or sulphur atoms, phenyl which is optionally substituted by halogen, nitro, $C_1-C_4$-alkyl, $C_1-C_4$-alkoxy, $C_1-C_3$-halogenoalkyl or $C_1-C_3$-halogenoalkoxy, or represents phenyl-$C_1-C_4$-alkyl which is optionally substituted by halogen, $C_1-C_4$-alkyl, $C_1-C_4$-alkoxy, $C_1-C_3$-halogenoalkyl, or $C_1-C_3$-halogenoalkoxy, or represents furanyl, thienyl, pyridyl, pyrimidyl, thiazolyl or pyrazolyl each of which is optionally substituted by halogen and/or $C_1$–$C_6$-alkyl, phenoxy-$C_1$–$C_5$-alkyl which is optionally substituted by halogen and/or $C_1$–$C_4$-alkyl, pyridyloxy-$C_1$–$C_5$-alkyl, pyrimidyloxy-$C_1$–$C_5$-alkyl or thiazolyloxy-$C_1$–$C_5$-alkyl, each of which is optionally substituted by halogen, amino and/or $C_1$–$C_4$-alkyl, $R^2$ represents in each case optionally halogen-substituted $C_1$–$C_6$-alkyl, $C_3$–$C_6$-alkenyl, $C_1$–$C_6$-alkoxy-$C_2$–$C_6$-alkyl or $C_1$–$C_6$polyalkoxy-$C_2$–$C_6$-alkyl, or represents $C_3$–$C_7$-cycloalkyl, which is optionally substituted by fluorine, chlorine or $C_1$–$C_4$-alkyl, phenyl or benzyl, each of which is optionally substituted by halogen, nitro, $C_1$–$C_4$-alkyl, $C_1$–$C_3$-alkoxy or $C_1$–$C_3$-halogenoalkyl, $R^3$, $R^4$ and $R^5$ independently of one another represent $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio, $C_2$–$C_4$-alkinylthio or $C_3$–$C_6$-cycloalkylthio, each of which is optionally substituted by halogen, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ and $R^7$ independently of one another represent hydrogen or represent $C_1$–$C_{20}$-alkyl, $C_1$–$C_{20}$-alkoxy, $C_3$–$C_8$-alkenyl or $C_1$–$C_{20}$-alkoxy-$C_1$–$C_{20}$-alkyl, each of which is optionally substituted by halogen, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, or together represent a $C_4$–$C_6$-alkylene ring which is optionally interrupted by oxygen or sulphur, and the stereomerically and enantiomerically pure forms of compounds of formula (I).

Very particularly preferred compounds of the formula (I) are those in which

X represents methyl, ethyl, propyl, i-propyl, fluorine, chlorine, bromine, methoxy, ethoxy or trifluoromethyl, Y represents hydrogen, methyl, ethyl, propyl, i-propyl, butyl, i-butyl, tert-butyl, fluorine, chlorine, bromine, methoxy, ethoxy or trifluoromethyl, Z represents methyl, ethyl, i-propyl, butyl, i-butyl, tert-butyl, fluorine, chlorine, bromine, methoxy or ethoxy, n represents 0 or 1, A and B together with the carbon atom to which they are bonded form a saturated or unsaturated 5- to 6-membered ring which is substituted by $C_1$–$C_4$-alkoxy, $C_1$–$C_2$-alkylthio, $C_1$–$C_2$-alkylsulphoxyl or $C_1$–$C_2$-alkylsulphonyl, carboxyl or $CO_2R^2$ or A and B together with the carbon atom to which they are bonded represent a $C_4$–$C_6$-membered ring in which two substituents together with the carbon atoms to which they are bonded represent a saturated $C_5$–$C_6$-ring which is optionally substituted by methyl, ethyl, methoxy, ethoxy, fluorine or chlorine and which can be interrupted by oxygen or sulphur, G represents hydrogen (a) or the groups

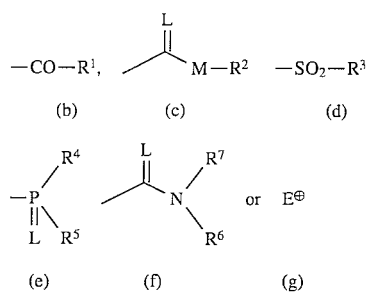

in which $E^\oplus$ represents a metal ion equivalent or an ammonium ion,

L and M in each case represent oxygen or sulphur, $R^1$ represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_1$–$C_4$-alkyl or $C_3$–$C_6$-cycloalkyl, which is optionally substituted by fluorine, chlorine, methyl or ethyl and which can be interrupted by 1–2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy or nitro, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents furanyl, thienyl, pyridyl, pyrimidyl, thiazolyl or pyrazolyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl, $R^2$ represents $C_1$–$C_{14}$-alkyl, $C_3$–$C_{14}$-alkenyl, $C_1$–$C_{14}$-alkoxy-$C_2$–$C_6$-alkyl or $C_1$–$C_4$-polyalkoxy-$C_2$–$C_6$-alkyl, each of which is optionally substituted by fluorine or chlorine, or represents $C_3$–$C_6$-cycloalkyl, which is optionally substituted by fluorine, chlorine, methyl or ethyl, or represents phenyl or benzyl, each of which is optionally substituted by fluorine, chlorine, nitro, methyl, ethyl, propyl, i-propyl, methoxy, ethoxy or trifluoromethyl, $R^3$, $R^4$ and $R^5$ independently of one another represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represents phenyl, phenoxy or phenylthio, each of which is optionally substituted by fluorine, chlorine, bromine, nitro, cyano, $C_1$–$C_2$-alkoxy, $C_1$–$C_4$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl, $R^6$ and $R^7$ independently of one another represent hydrogen or represent $C_1$–$C_{10}$-alkyl, $C_3$–$C_6$-alkenyl, $C_1$–$C_{10}$-alkoxy or $C_1$–$C_{10}$-alkoxy-$C_1$–$C_{10}$-alkyl, each of which is optionally substituted by fluorine, chlorine or bromine, or represent phenyl which is optionally substituted by fluorine, chlorine, bromine, $C_1$–$C_2$-halogenoalkyl, $C_1$–$C_2$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_1$-alkoxy, or together represent a $C_4$–$C_6$-alkylene ring which is optionally interrupted by oxygen or sulphur, and the stereomerically and enantiomerically pure forms of compounds of the formula (I).

The following 3-aryl-4-hydroxy-$\Delta^3$-dihydrofuranone derivatives of the formula (Ia) may be mentioned individually in addition to the compounds mentioned in the preparation examples:

TABLE 1

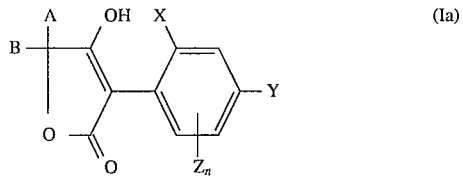

(Ia)

| X | Y | $Z_n$ | A | B |
|---|---|---|---|---|
| Cl | Cl | H | —(CH$_2$)$_4$—CH(OCH$_3$)— | |
| Cl | Cl | H | —(CH$_2$)$_3$—CH(OCH$_3$)—CH$_2$— | |
| Cl | Cl | H | —(CH$_2$)$_2$—CH(OCH$_3$)—(CH$_2$)$_2$— | |
| Cl | Cl | H | —(CH$_2$)$_2$—CH(OC$_2$H$_5$)—(CH$_2$)$_2$— | |
| Cl | Cl | H | —(CH$_2$)$_2$—CH(OC$_3$H$_7$)—(CH$_2$)$_2$— | |
| Cl | Cl | H | —(CH$_2$)$_2$—CH(O-i-C$_3$H$_7$)—(CH$_2$)$_2$— | |
| Cl | Cl | H | —(CH$_2$)$_2$—CH(O-t-C$_4$H$_9$)—(CH$_2$)$_2$— | |
| Cl | Cl | H | —(CH$_2$)$_3$—CH(SCH$_3$)—CH$_2$— | |
| Cl | Cl | H | —(CH$_2$)$_2$—CH(SCH$_3$)—(CH$_2$)$_2$— | |
| Cl | Cl | H | —CH$_2$–cyclohexyl | |
| Cl | Cl | H | —CH$_2$–cyclohexyl–CH$_2$ | |
| Cl | Cl | H | —(CH$_2$)$_2$–cyclohexyl–CH$_2$ | |
| Cl | Cl | H | —(CH$_2$)$_2$–cyclopentyl–CH$_2$ | |
| Cl | Cl | H | —CH$_2$–cyclopentenyl | |
| Cl | Cl | H | —CH$_2$–cyclopentyl | |
| Cl | Cl | H | —CH$_2$–dihydrofuranyl | |

TABLE 1-continued

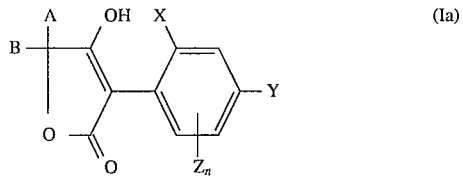

(Ia)

| X | Y | $Z_n$ | A | B |
|---|---|---|---|---|
| Cl | Cl | H | —CH$_2$–tetrahydrofuranyl | |
| CH$_3$ | CH$_3$ | H | —(CH$_2$)$_4$—CH(OCH$_3$)— | |
| CH$_3$ | CH$_3$ | H | —(CH$_2$)$_3$—CH(OCH$_3$)—CH$_2$— | |
| CH$_3$ | CH$_3$ | H | —(CH$_2$)$_2$—CH(OCH$_3$)—(CH$_2$)$_2$— | |
| CH$_3$ | CH$_3$ | H | —(CH$_2$)$_2$—CH(OC$_2$H$_5$)—(CH$_2$)$_2$— | |
| CH$_3$ | CH$_3$ | H | —(CH$_2$)$_2$—CH(OC$_3$H$_7$)—(CH$_2$)$_2$— | |
| CH$_3$ | CH$_3$ | H | —(CH$_2$)$_2$—CH(O-i-C$_3$H$_7$)—(CH$_2$)$_2$— | |
| CH$_3$ | CH$_3$ | H | —(CH$_2$)$_2$—CH(O-t-C$_4$H$_9$)—(CH$_2$)$_2$— | |
| CH$_3$ | CH$_3$ | H | —(CH$_2$)$_3$—CH(SCH$_3$)—CH$_2$— | |
| CH$_3$ | CH$_3$ | H | —(CH$_2$)$_2$—CH(SCH$_3$)—(CH$_2$)$_2$— | |
| CH$_3$ | CH$_3$ | H | —CH$_2$–cyclohexyl | |
| CH$_3$ | CH$_3$ | H | —CH$_2$–cyclohexyl–CH$_2$ | |
| CH$_3$ | CH$_3$ | H | —(CH$_2$)$_2$–cyclohexyl–CH$_2$ | |
| CH$_3$ | CH$_3$ | H | —(CH$_2$)$_2$–cyclopentyl–CH$_2$ | |
| CH$_3$ | CH$_3$ | H | —CH$_2$–cyclopentenyl | |
| CH$_3$ | CH$_3$ | H | —CH$_2$–cyclopentyl | |
| CH$_3$ | CH$_3$ | H | —CH$_2$–dihydrofuranyl | |

TABLE 1-continued

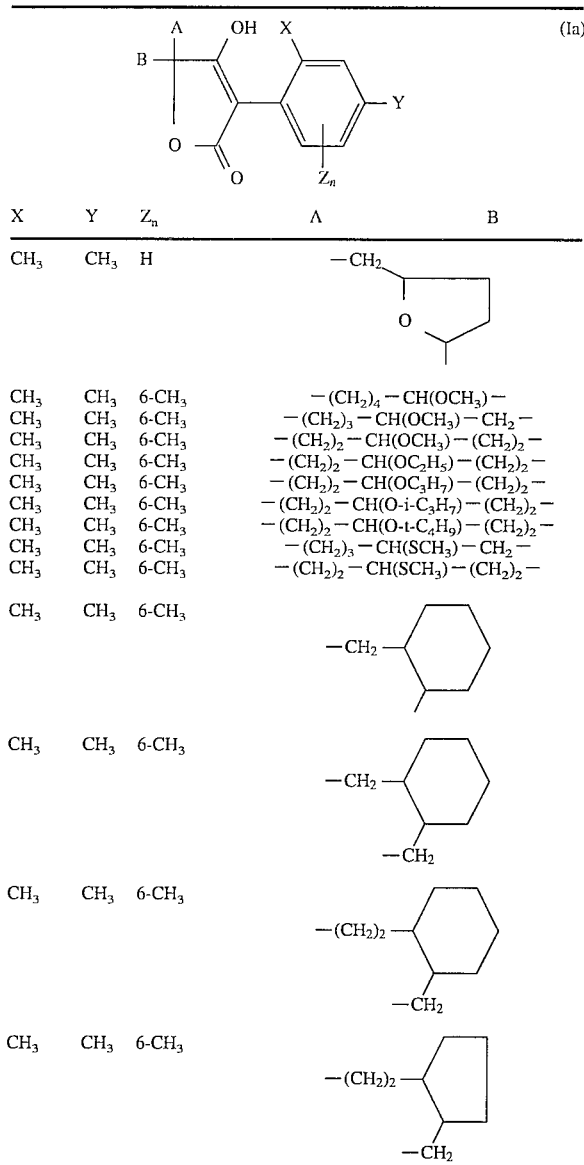

| X | Y | $Z_n$ | A | B |
|---|---|---|---|---|
| $CH_3$ | $CH_3$ | H | | |
| $CH_3$ | $CH_3$ | 6-$CH_3$ | $-(CH_2)_4-CH(OCH_3)-$ | |
| $CH_3$ | $CH_3$ | 6-$CH_3$ | $-(CH_2)_3-CH(OCH_3)-CH_2-$ | |
| $CH_3$ | $CH_3$ | 6-$CH_3$ | $-(CH_2)_2-CH(OCH_3)-(CH_2)_2-$ | |
| $CH_3$ | $CH_3$ | 6-$CH_3$ | $-(CH_2)_2-CH(OC_2H_5)-(CH_2)_2-$ | |
| $CH_3$ | $CH_3$ | 6-$CH_3$ | $-(CH_2)_2-CH(OC_3H_7)-(CH_2)_2-$ | |
| $CH_3$ | $CH_3$ | 6-$CH_3$ | $-(CH_2)_2-CH(O-i-C_3H_7)-(CH_2)_2-$ | |
| $CH_3$ | $CH_3$ | 6-$CH_3$ | $-(CH_2)_2-CH(O-t-C_4H_9)-(CH_2)_2-$ | |
| $CH_3$ | $CH_3$ | 6-$CH_3$ | $-(CH_2)_3-CH(SCH_3)-CH_2-$ | |
| $CH_3$ | $CH_3$ | 6-$CH_3$ | $-(CH_2)_2-CH(SCH_3)-(CH_2)_2-$ | |
| $CH_3$ | $CH_3$ | 6-$CH_3$ | | |
| $CH_3$ | $CH_3$ | 6-$CH_3$ | | |
| $CH_3$ | $CH_3$ | 6-$CH_3$ | | |
| $CH_3$ | $CH_3$ | 6-$CH_3$ | | |

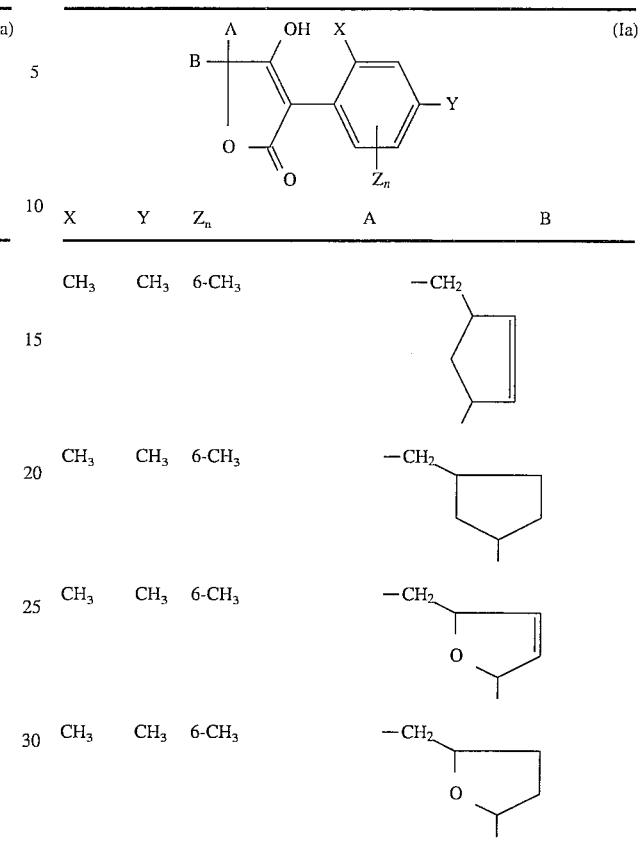

The following 3-aryl-4-hydroxy-$\Delta^3$-dihydrofuranone derivatives of the formula (Ib) may be mentioned individually in addition to the compounds mentioned in the preparation examples:

TABLE 2

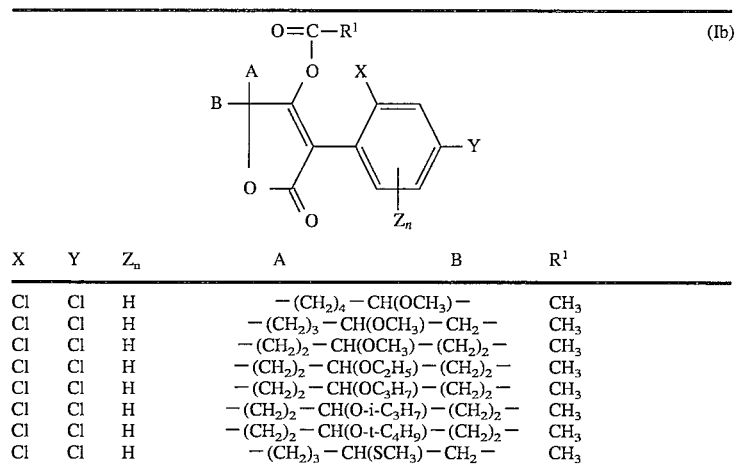

| X | Y | $Z_n$ | A | B | $R^1$ |
|---|---|---|---|---|---|
| Cl | Cl | H | $-(CH_2)_4-CH(OCH_3)-$ | | $CH_3$ |
| Cl | Cl | H | $-(CH_2)_3-CH(OCH_3)-CH_2-$ | | $CH_3$ |
| Cl | Cl | H | $-(CH_2)_2-CH(OCH_3)-(CH_2)_2-$ | | $CH_3$ |
| Cl | Cl | H | $-(CH_2)_2-CH(OC_2H_5)-(CH_2)_2-$ | | $CH_3$ |
| Cl | Cl | H | $-(CH_2)_2-CH(OC_3H_7)-(CH_2)_2-$ | | $CH_3$ |
| Cl | Cl | H | $-(CH_2)_2-CH(O-i-C_3H_7)-(CH_2)_2-$ | | $CH_3$ |
| Cl | Cl | H | $-(CH_2)_2-CH(O-t-C_4H_9)-(CH_2)_2-$ | | $CH_3$ |
| Cl | Cl | H | $-(CH_2)_3-CH(SCH_3)-CH_2-$ | | $CH_3$ |

TABLE 2-continued

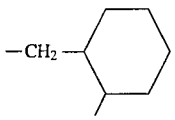

(Ib)

| X | Y | $Z_n$ | A B | $R^1$ |
|---|---|---|---|---|
| Cl | Cl | H | $-(CH_2)_2-CH(SCH_3)-(CH_2)_2-$ | $CH_3$ |
| Cl | Cl | H | 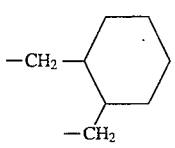 | $CH_3$ |
| Cl | Cl | H | 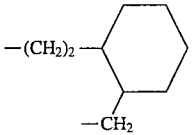 | $CH_3$ |
| Cl | Cl | H | 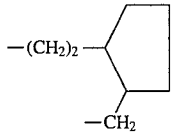 | $CH_3$ |
| Cl | Cl | H | 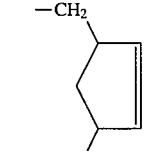 | $CH_3$ |
| Cl | Cl | H | 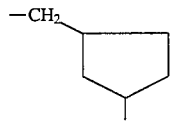 | $CH_3$ |
| Cl | Cl | H | 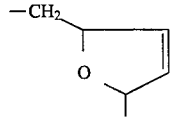 | $CH_3$ |
| Cl | Cl | H | 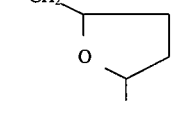 | $CH_3$ |
| Cl | Cl | H | | $CH_3$ |
| Cl | Cl | H | $-(CH_2)_4-CH(OCH_3)-$ | $i$-$C_3H_7$ |
| Cl | Cl | H | $-(CH_2)_3-CH(OCH_3)-CH_2-$ | $i$-$C_3H_7$ |
| Cl | Cl | H | $-(CH_2)_2-CH(OCH_3)-(CH_2)_2-$ | $i$-$C_3H_7$ |
| Cl | Cl | H | $-(CH_2)_2-CH(OC_2H_5)-(CH_2)_2-$ | $i$-$C_3H_7$ |
| Cl | Cl | H | $-(CH_2)_2-CH(OC_3H_7)-(CH_2)_2-$ | $i$-$C_3H_7$ |
| Cl | Cl | H | $-(CH_2)_2-CH(O\text{-}i\text{-}C_3H_7)-(CH_2)_2-$ | $i$-$C_3H_7$ |
| Cl | Cl | H | $-(CH_2)_2-CH(O\text{-}t\text{-}C_4H_9)-(CH_2)_2-$ | $i$-$C_3H_7$ |
| Cl | Cl | H | $-(CH_2)_3-CH(SCH_3)-CH_2-$ | $i$-$C_3H_7$ |
| Cl | Cl | H | $-(CH_2)_2-CH(SCH_3)-(CH_2)_2-$ | $i$-$C_3H_7$ |

TABLE 2-continued

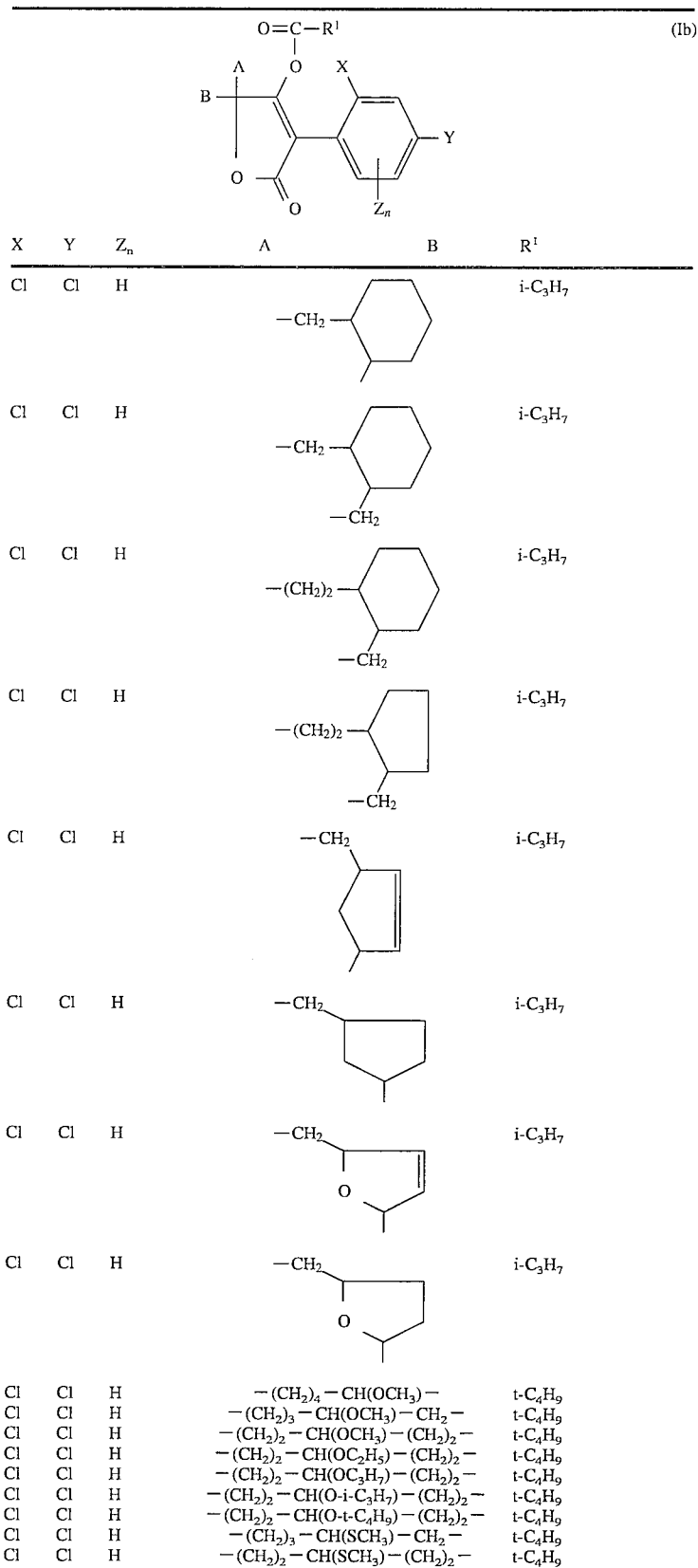

(Ib)

| X | Y | $Z_n$ | A | B | $R^1$ |
|---|---|---|---|---|---|
| Cl | Cl | H | —CH₂-cyclohexyl | | i-$C_3H_7$ |
| Cl | Cl | H | —CH₂-cyclohexyl-CH₂— | | i-$C_3H_7$ |
| Cl | Cl | H | —(CH₂)₂-cyclohexyl-CH₂— | | i-$C_3H_7$ |
| Cl | Cl | H | —(CH₂)₂-cyclopentyl-CH₂— | | i-$C_3H_7$ |
| Cl | Cl | H | —CH₂-cyclohexenyl- | | i-$C_3H_7$ |
| Cl | Cl | H | —CH₂-cyclopentyl- | | i-$C_3H_7$ |
| Cl | Cl | H | —CH₂-(2,5-dihydrofuryl)- | | i-$C_3H_7$ |
| Cl | Cl | H | —CH₂-(tetrahydrofuryl)- | | i-$C_3H_7$ |
| Cl | Cl | H | —(CH₂)₄—CH(OCH₃)— | | t-$C_4H_9$ |
| Cl | Cl | H | —(CH₂)₃—CH(OCH₃)—CH₂— | | t-$C_4H_9$ |
| Cl | Cl | H | —(CH₂)₂—CH(OCH₃)—(CH₂)₂— | | t-$C_4H_9$ |
| Cl | Cl | H | —(CH₂)₂—CH(OC₂H₅)—(CH₂)₂— | | t-$C_4H_9$ |
| Cl | Cl | H | —(CH₂)₂—CH(OC₃H₇)—(CH₂)₂— | | t-$C_4H_9$ |
| Cl | Cl | H | —(CH₂)₂—CH(O-i-C₃H₇)—(CH₂)₂— | | t-$C_4H_9$ |
| Cl | Cl | H | —(CH₂)₂—CH(O-t-C₄H₉)—(CH₂)₂— | | t-$C_4H_9$ |
| Cl | Cl | H | —(CH₂)₃—CH(SCH₃)—CH₂— | | t-$C_4H_9$ |
| Cl | Cl | H | —(CH₂)₂—CH(SCH₃)—(CH₂)₂— | | t-$C_4H_9$ |

TABLE 2-continued

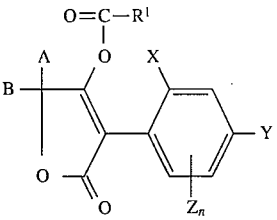

| X | Y | Z$_n$ | A | B | R$^1$ |
|---|---|---|---|---|---|
| Cl | Cl | H | (CH$_2$-cyclohexyl-methyl) | | t-C$_4$H$_9$ |
| Cl | Cl | H | (CH$_2$-cyclohexyl-CH$_2$) | | t-C$_4$H$_9$ |
| Cl | Cl | H | (−(CH$_2$)$_2$-cyclohexyl-CH$_2$) | | t-C$_4$H$_9$ |
| Cl | Cl | H | (−(CH$_2$)$_2$-cyclopentyl-CH$_2$) | | t-C$_4$H$_9$ |
| Cl | Cl | H | (−CH$_2$-cyclohexenyl-) | | t-C$_4$H$_9$ |
| Cl | Cl | H | (−CH$_2$-cyclopentyl-) | | t-C$_4$H$_9$ |
| Cl | Cl | H | (−CH$_2$-dihydrofuranyl-) | | t-C$_4$H$_9$ |
| Cl | Cl | H | (−CH$_2$-tetrahydrofuranyl-) | | t-C$_4$H$_9$ |
| Cl | Cl | H | −(CH$_2$)$_4$−CH(OCH$_3$)− | | (CH$_3$)$_2$CH$_2$Cl |
| Cl | Cl | H | −(CH$_2$)$_3$−CH(OCH$_3$)−CH$_2$− | | (CH$_3$)$_2$CH$_2$Cl |
| Cl | Cl | H | −(CH$_2$)$_2$−CH(OCH$_3$)−(CH$_2$)$_2$− | | (CH$_3$)$_2$CH$_2$Cl |
| Cl | Cl | H | −(CH$_2$)$_2$−CH(OC$_2$H$_5$)−(CH$_2$)$_2$− | | (CH$_3$)$_2$CH$_2$Cl |
| Cl | Cl | H | −(CH$_2$)$_2$−CH(OC$_3$H$_7$)−(CH$_2$)$_2$− | | (CH$_3$)$_2$CH$_2$Cl |
| Cl | Cl | H | −(CH$_2$)$_2$−CH(O-i-C$_3$H$_7$)−(CH$_2$)$_2$− | | −C(CH$_3$)$_2$CH$_2$Cl |
| Cl | Cl | H | −(CH$_2$)$_2$−CH(O-t-C$_4$H$_9$)−(CH$_2$)$_2$− | | −C(CH$_3$)$_2$CH$_2$Cl |
| Cl | Cl | H | −(CH$_2$)$_3$−CH(SCH$_3$)−CH$_2$− | | −C(CH$_3$)$_2$CH$_2$Cl |
| Cl | Cl | H | −(CH$_2$)$_2$−CH(SCH$_3$)−(CH$_2$)$_2$− | | −C(CH$_3$)$_2$CH$_2$Cl |

TABLE 2-continued

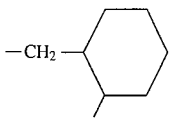

| X | Y | $Z_n$ | A | B | $R^1$ |
|---|---|---|---|---|---|
| Cl | Cl | H | $-CH_2$ | 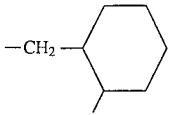 | $-C(CH_3)_2CH_2Cl$ |
| Cl | Cl | H | $-CH_2$ | 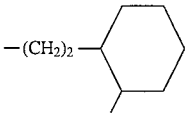 $-CH_2$ | $-C(CH_3)_2CH_2Cl$ |
| Cl | Cl | H | $-(CH_2)_2$ | 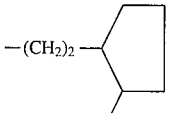 $-CH_2$ | $-C(CH_3)_2CH_2Cl$ |
| Cl | Cl | H | $-(CH_2)_2$ | 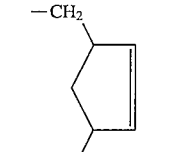 $-CH_2$ | $-C(CH_3)_2CH_2Cl$ |
| Cl | Cl | H | $-CH_2$ | 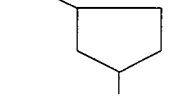 | $-C(CH_3)_2CH_2Cl$ |
| Cl | Cl | H | $-CH_2$ | 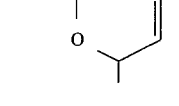 | $-C(CH_3)_2CH_2Cl$ |
| Cl | Cl | H | $-CH_2$ | 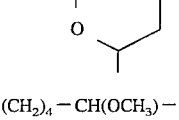 | $-C(CH_3)_2CH_2Cl$ |
| Cl | Cl | H | $-CH_2$ | | $-C(CH_3)_2CH_2Cl$ |
| Cl | Cl | H | $-(CH_2)_4-CH(OCH_3)-$ | | $-C(CH_3)_2CH_2CH_3$ |
| Cl | Cl | H | $-(CH_2)_3-CH(OCH_3)-CH_2-$ | | $-C(CH_3)_2CH_2CH_3$ |
| Cl | Cl | H | $-(CH_2)_2-CH(OCH_3)-(CH_2)_2-$ | | $-C(CH_3)_2CH_2CH_3$ |
| Cl | Cl | H | $-(CH_2)_2-CH(OC_2H_5)-(CH_2)_2-$ | | $-C(CH_3)_2CH_2CH_3$ |
| Cl | Cl | H | $-(CH_2)_2-CH(OC_3H_7)-(CH_2)_2-$ | | $-C(CH_3)_2CH_2CH_3$ |
| Cl | Cl | H | $-(CH_2)_2-CH(O\text{-}i\text{-}C_3H_7)-(CH_2)_2-$ | | $-C(CH_3)_2CH_2CH_3$ |
| Cl | Cl | H | $-(CH_2)_2-CH(O\text{-}t\text{-}C_4H_9)-(CH_2)_2-$ | | $-C(CH_3)_2CH_2CH_3$ |
| Cl | Cl | H | $-(CH_2)_3-CH(SCH_3)-CH_2-$ | | $-C(CH_3)_2CH_2CH_3$ |
| Cl | Cl | H | $-(CH_2)_2-CH(SCH_3)-(CH_2)_2-$ | | $-C(CH_3)_2CH_2CH_3$ |

TABLE 2-continued $$\text{(Ib)}$$

Structure (Ib): a substituted benzene ring bearing X, Y, and $Z_n$ substituents, connected to a vinyl group with a carboxylate $O-C(=O)-R^1$ and a cyclic ester (-C(A)(B)-O-C(=O)-) forming the A/B ring.

| X | Y | $Z_n$ | A | B | $R^1$ |
|---|---|---|---|---|---|
| Cl | Cl | H | —CH$_2$—(cyclohexyl, 1,2-disubst.) | | —C(CH$_3$)$_2$CH$_2$CH$_3$ |
| Cl | Cl | H | —CH$_2$—(cyclohexyl) | —CH$_2$— (1,2-disubst. cyclohexane) | —C(CH$_3$)$_2$CH$_2$CH$_3$ |
| Cl | Cl | H | —(CH$_2$)$_2$—(cyclohexyl) | —CH$_2$— | —C(CH$_3$)$_2$CH$_2$CH$_3$ |
| Cl | Cl | H | —(CH$_2$)$_2$—(cyclopentyl) | —CH$_2$— | —C(CH$_3$)$_2$CH$_2$CH$_3$ |
| Cl | Cl | H | —CH$_2$—(cyclopentenyl, 1,3-disubst.) | | —C(CH$_3$)$_2$CH$_2$CH$_3$ |
| Cl | Cl | H | —CH$_2$—(cyclopentyl, 1,3-disubst.) | | —C(CH$_3$)$_2$CH$_2$CH$_3$ |
| Cl | Cl | H | —CH$_2$—(2,5-disubst. 2,5-dihydrofuran) | | —C(CH$_3$)$_2$CH$_2$CH$_3$ |
| Cl | Cl | H | —CH$_2$—(2,5-disubst. tetrahydrofuran) | | —C(CH$_3$)$_2$CH$_2$CH$_3$ |
| CH$_3$ | CH$_3$ | H | —(CH$_2$)$_4$—CH(OCH$_3$)— | | CH$_3$ |
| CH$_3$ | CH$_3$ | H | —(CH$_2$)$_3$—CH(OCH$_3$)—CH$_2$— | | CH$_3$ |
| CH$_3$ | CH$_3$ | H | —(CH$_2$)$_2$—CH(OCH$_3$)—(CH$_2$)$_2$— | | CH$_3$ |
| CH$_3$ | CH$_3$ | H | —(CH$_2$)$_2$—CH(OC$_2$H$_5$)—(CH$_2$)$_2$— | | CH$_3$ |
| CH$_3$ | CH$_3$ | H | —(CH$_2$)$_2$—CH(OC$_3$H$_7$)—(CH$_2$)$_2$— | | CH$_3$ |
| CH$_3$ | CH$_3$ | H | —(CH$_2$)$_2$—CH(O-i-C$_3$H$_7$)—(CH$_2$)$_2$— | | CH$_3$ |
| CH$_3$ | CH$_3$ | H | —(CH$_2$)$_2$—CH(O-t-C$_4$H$_9$)—(CH$_2$)$_2$— | | CH$_3$ |
| CH$_3$ | CH$_3$ | H | —(CH$_2$)$_3$—CH(SCH$_3$)—CH$_2$— | | CH$_3$ |
| CH$_3$ | CH$_3$ | H | —(CH$_2$)$_2$—CH(SCH$_3$)—(CH$_2$)$_2$— | | CH$_3$ |

TABLE 2-continued

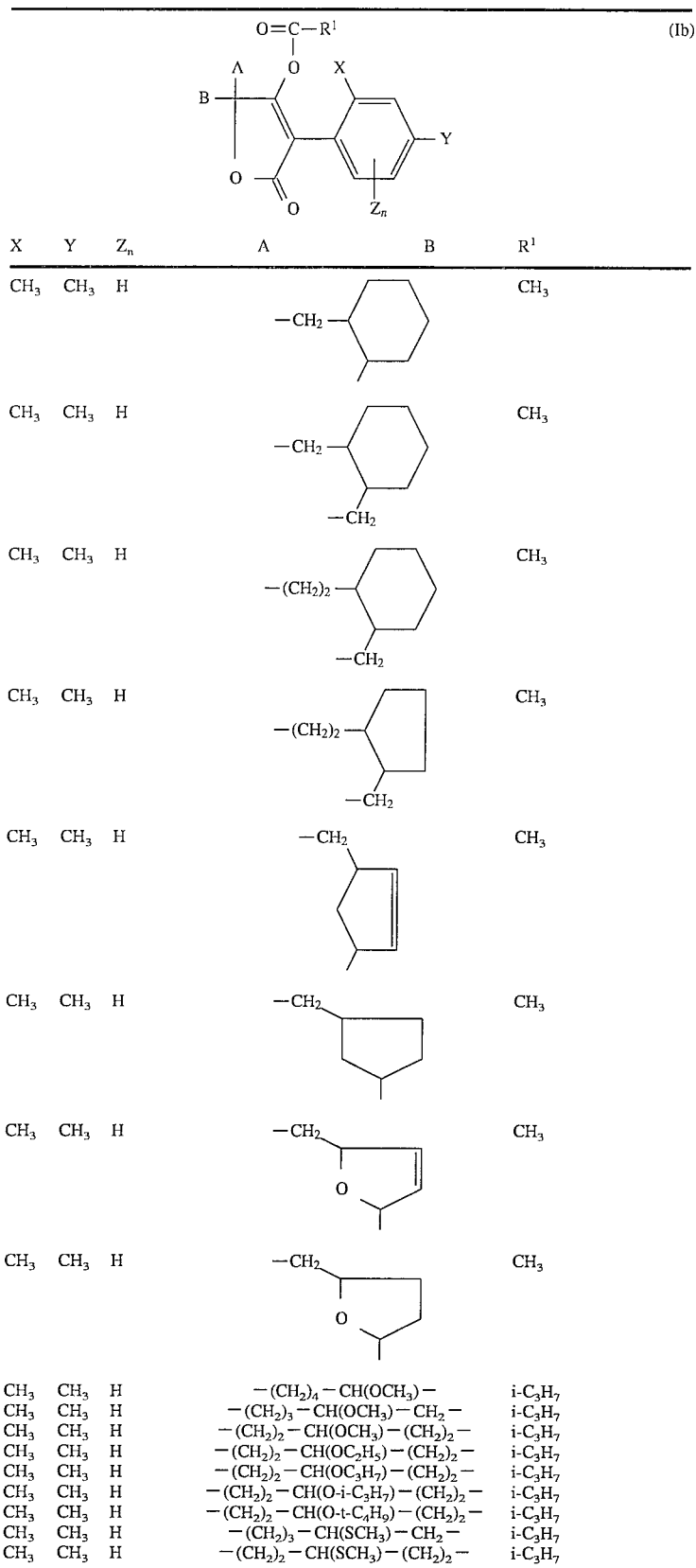

(Ib)

| X | Y | $Z_n$ | A | B | $R^1$ |
|---|---|---|---|---|---|
| $CH_3$ | $CH_3$ | H | —$CH_2$—(2-methylcyclohexyl) | | $CH_3$ |
| $CH_3$ | $CH_3$ | H | —$CH_2$—(2-(—$CH_2$)cyclohexyl) | | $CH_3$ |
| $CH_3$ | $CH_3$ | H | —$(CH_2)_2$—(2-(—$CH_2$)cyclohexyl) | | $CH_3$ |
| $CH_3$ | $CH_3$ | H | —$(CH_2)_2$—(2-(—$CH_2$)cyclopentyl) | | $CH_3$ |
| $CH_3$ | $CH_3$ | H | —$CH_2$—(cyclohexenyl-methyl) | | $CH_3$ |
| $CH_3$ | $CH_3$ | H | —$CH_2$—(methylcyclopentyl) | | $CH_3$ |
| $CH_3$ | $CH_3$ | H | —$CH_2$—(2,5-dihydrofuranyl) | | $CH_3$ |
| $CH_3$ | $CH_3$ | H | —$CH_2$—(tetrahydrofuranyl) | | $CH_3$ |
| $CH_3$ | $CH_3$ | H | —$(CH_2)_4$—CH(OCH$_3$)— | | i-$C_3H_7$ |
| $CH_3$ | $CH_3$ | H | —$(CH_2)_3$—CH(OCH$_3$)—CH$_2$— | | i-$C_3H_7$ |
| $CH_3$ | $CH_3$ | H | —$(CH_2)_2$—CH(OCH$_3$)—$(CH_2)_2$— | | i-$C_3H_7$ |
| $CH_3$ | $CH_3$ | H | —$(CH_2)_2$—CH(OC$_2$H$_5$)—$(CH_2)_2$— | | i-$C_3H_7$ |
| $CH_3$ | $CH_3$ | H | —$(CH_2)_2$—CH(OC$_3$H$_7$)—$(CH_2)_2$— | | i-$C_3H_7$ |
| $CH_3$ | $CH_3$ | H | —$(CH_2)_2$—CH(O-i-C$_3$H$_7$)—$(CH_2)_2$— | | i-$C_3H_7$ |
| $CH_3$ | $CH_3$ | H | —$(CH_2)_2$—CH(O-t-C$_4$H$_9$)—$(CH_2)_2$— | | i-$C_3H_7$ |
| $CH_3$ | $CH_3$ | H | —$(CH_2)_3$—CH(SCH$_3$)—CH$_2$— | | i-$C_3H_7$ |
| $CH_3$ | $CH_3$ | H | —$(CH_2)_2$—CH(SCH$_3$)—$(CH_2)_2$— | | i-$C_3H_7$ |

TABLE 2-continued

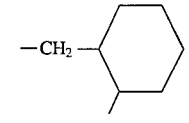

(Ib)

| X | Y | Z$_n$ | A | B | R$^1$ |
|---|---|---|---|---|---|
| CH$_3$ | CH$_3$ | H | 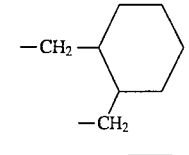 | | i-C$_3$H$_7$ |
| CH$_3$ | CH$_3$ | H | 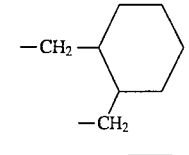 | | i-C$_3$H$_7$ |
| CH$_3$ | CH$_3$ | H | 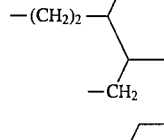 | | i-C$_3$H$_7$ |
| CH$_3$ | CH$_3$ | H | 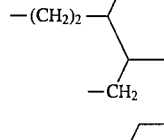 | | i-C$_3$H$_7$ |
| CH$_3$ | CH$_3$ | H | 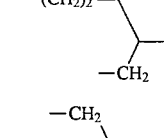 | | i-C$_3$H$_7$ |
| CH$_3$ | CH$_3$ | H | 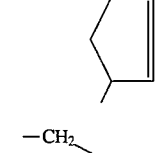 | | i-C$_3$H$_7$ |
| CH$_3$ | CH$_3$ | H | 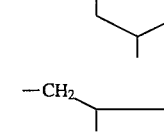 | | i-C$_3$H$_7$ |
| CH$_3$ | CH$_3$ | H | 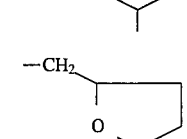 | | i-C$_3$H$_7$ |
| CH$_3$ | CH$_3$ | H | —(CH$_2$)$_4$—CH(OCH$_3$)— | | t-C$_4$H$_9$ |
| CH$_3$ | CH$_3$ | H | —(CH$_2$)$_3$—CH(OCH$_3$)—CH$_2$— | | t-C$_4$H$_9$ |
| CH$_3$ | CH$_3$ | H | —(CH$_2$)$_2$—CH(OCH$_3$)—(CH$_2$)$_2$— | | t-C$_4$H$_9$ |
| CH$_3$ | CH$_3$ | H | —(CH$_2$)$_2$—CH(OC$_2$H$_5$)—(CH$_2$)$_2$— | | t-C$_4$H$_9$ |
| CH$_3$ | CH$_3$ | H | —(CH$_2$)$_2$—CH(OC$_3$H$_7$)—(CH$_2$)$_2$— | | t-C$_4$H$_9$ |
| CH$_3$ | CH$_3$ | H | —(CH$_2$)$_2$—CH(O-i-C$_3$H$_7$)—(CH$_2$)$_2$— | | t-C$_4$H$_9$ |
| CH$_3$ | CH$_3$ | H | —(CH$_2$)$_2$—CH(O-t-C$_4$H$_9$)—(CH$_2$)$_2$— | | t-C$_4$H$_9$ |
| CH$_3$ | CH$_3$ | H | —(CH$_2$)$_3$—CH(SCH$_3$)—CH$_2$— | | t-C$_4$H$_9$ |
| CH$_3$ | CH$_3$ | H | —(CH$_2$)$_2$—CH(SCH$_3$)—(CH$_2$)$_2$— | | t-C$_4$H$_9$ |

TABLE 2-continued (Ib) structure: O=C−R¹ attached via O to A−B−C=C with aryl group bearing X, Y, Z_n substituents

| X | Y | Z_n | A B | R¹ |
|---|---|---|---|---|
| CH₃ | CH₃ | H | −CH₂−(methylcyclohexyl) | t-C₄H₉ |
| CH₃ | CH₃ | H | −CH₂−(cyclohexyl)−CH₂− | t-C₄H₉ |
| CH₃ | CH₃ | H | −(CH₂)₂−(cyclohexyl)−CH₂− | t-C₄H₉ |
| CH₃ | CH₃ | H | −(CH₂)₂−(cyclopentyl)−CH₂− | t-C₄H₉ |
| CH₃ | CH₃ | H | −CH₂−(cyclopentenyl)−CH₂− (with methyl) | t-C₄H₉ |
| CH₃ | CH₃ | H | −CH₂−(cyclopentyl)− | t-C₄H₉ |
| CH₃ | CH₃ | H | −CH₂−(2,5-dihydrofuranyl)− | t-C₄H₉ |
| CH₃ | CH₃ | H | −CH₂−(tetrahydrofuranyl)− | t-C₄H₉ |
| CH₃ | CH₃ | H | −(CH₂)₄−CH(OCH₃)− | −C(CH₃)₂CH₂Cl |
| CH₃ | CH₃ | H | −(CH₂)₃−CH(OCH₃)−CH₂− | −C(CH₃)₂CH₂Cl |
| CH₃ | CH₃ | H | −(CH₂)₂−CH(OCH₃)−(CH₂)₂− | −C(CH₃)₂CH₂Cl |
| CH₃ | CH₃ | H | −(CH₂)₂−CH(OC₂H₅)−(CH₂)₂− | −C(CH₃)₂CH₂Cl |
| CH₃ | CH₃ | H | −(CH₂)₂−CH(OC₃H₇)−(CH₂)₂− | −C(CH₃)₂CH₂Cl |
| CH₃ | CH₃ | H | −(CH₂)₂−CH(O-i-C₃H₇)−(CH₂)₂− | −C(CH₃)₂CH₂Cl |
| CH₃ | CH₃ | H | −(CH₂)₂−CH(O-t-C₄H₉)−(CH₂)₂− | −C(CH₃)₂CH₂Cl |
| CH₃ | CH₃ | H | −(CH₂)₃−CH(SCH₃)−CH₂− | −C(CH₃)₂CH₂Cl |
| CH₃ | CH₃ | H | −(CH₂)₂−CH(SCH₃)−(CH₂)₂− | −C(CH₃)₂CH₂Cl |

TABLE 2-continued $$\text{(Ib)}$$

Structure (Ib): A phenyl ring substituted at ortho with X, at para with Y, and with $Z_n$ on the ring; attached at another ortho position is a group =C(OC(=O)R$^1$)— connected to a carbon bearing substituents A and B, with a —C(=O)O— linkage forming a ring.

| X | Y | $Z_n$ | A | B | R$^1$ |
|---|---|---|---|---|---|
| CH$_3$ | CH$_3$ | H | —CH$_2$–(2-methylcyclohexyl) | | —C(CH$_3$)$_2$CH$_2$Cl |
| CH$_3$ | CH$_3$ | H | —CH$_2$– and —CH$_2$– on cyclohexane (1,2-bis(methylene)cyclohexane bridge) | | —C(CH$_3$)$_2$CH$_2$Cl |
| CH$_3$ | CH$_3$ | H | —(CH$_2$)$_2$– and —CH$_2$– on cyclohexane | | —C(CH$_3$)$_2$CH$_2$Cl |
| CH$_3$ | CH$_3$ | H | —(CH$_2$)$_2$– and —CH$_2$– on cyclopentane | | —C(CH$_3$)$_2$CH$_2$Cl |
| CH$_3$ | CH$_3$ | H | —CH$_2$–(4-methylcyclohex-2-enyl) | | —C(CH$_3$)$_2$CH$_2$Cl |
| CH$_3$ | CH$_3$ | H | —CH$_2$–(3-methylcyclopentyl) | | —C(CH$_3$)$_2$CH$_2$Cl |
| CH$_3$ | CH$_3$ | H | —CH$_2$–(5-methyl-2,5-dihydrofuran-2-yl) | | —C(CH$_3$)$_2$CH$_2$Cl |
| CH$_3$ | CH$_3$ | H | —CH$_2$–(5-methyltetrahydrofuran-2-yl) | | —C(CH$_3$)$_2$CH$_2$CH$_3$ |
| CH$_3$ | CH$_3$ | H | —(CH$_2$)$_4$—CH(OCH$_3$)— | | —C(CH$_3$)$_2$CH$_2$CH$_3$ |
| CH$_3$ | CH$_3$ | H | —(CH$_2$)$_3$—CH(OCH$_3$)—CH$_2$— | | —C(CH$_3$)$_2$CH$_2$CH$_3$ |
| CH$_3$ | CH$_3$ | H | —(CH$_2$)$_2$—CH(OCH$_3$)—(CH$_2$)$_2$— | | —C(CH$_3$)$_2$CH$_2$CH$_3$ |
| CH$_3$ | CH$_3$ | H | —(CH$_2$)$_2$—CH(OC$_2$H$_5$)—(CH$_2$)$_2$— | | —C(CH$_3$)$_2$CH$_2$CH$_3$ |
| CH$_3$ | CH$_3$ | H | —(CH$_2$)$_2$—CH(OC$_3$H$_7$)—(CH$_2$)$_2$— | | —C(CH$_3$)$_2$CH$_2$CH$_3$ |
| CH$_3$ | CH$_3$ | H | —(CH$_2$)$_2$—CH(O-i-C$_3$H$_7$)—(CH$_2$)$_2$— | | —C(CH$_3$)$_2$CH$_2$CH$_3$ |
| CH$_3$ | CH$_3$ | H | —(CH$_2$)$_2$—CH(O-t-C$_4$H$_9$)—(CH$_2$)$_2$— | | —C(CH$_3$)$_2$CH$_2$CH$_3$ |
| CH$_3$ | CH$_3$ | H | —(CH$_2$)$_3$—CH(SCH$_3$)—CH$_2$— | | —C(CH$_3$)$_2$CH$_2$CH$_3$ |
| CH$_3$ | CH$_3$ | H | —(CH$_2$)$_2$—CH(SCH$_3$)—(CH$_2$)$_2$— | | —C(CH$_3$)$_2$CH$_2$CH$_3$ |

TABLE 2-continued

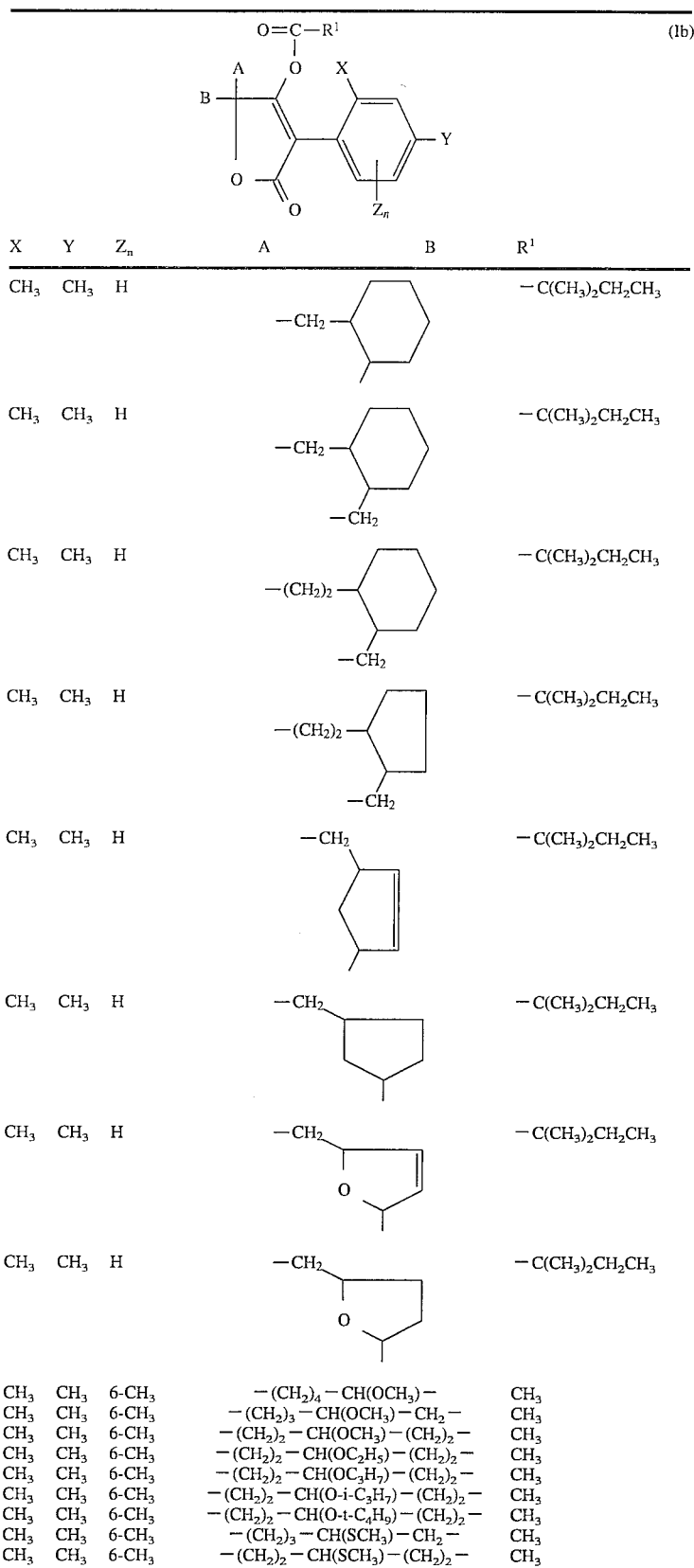

| X | Y | Z_n | A B | R^1 |
|---|---|---|---|---|
| $CH_3$ | $CH_3$ | H | | $-C(CH_3)_2CH_2CH_3$ |
| $CH_3$ | $CH_3$ | H | | $-C(CH_3)_2CH_2CH_3$ |
| $CH_3$ | $CH_3$ | H | | $-C(CH_3)_2CH_2CH_3$ |
| $CH_3$ | $CH_3$ | H | | $-C(CH_3)_2CH_2CH_3$ |
| $CH_3$ | $CH_3$ | H | | $-C(CH_3)_2CH_2CH_3$ |
| $CH_3$ | $CH_3$ | H | | $-C(CH_3)_2CH_2CH_3$ |
| $CH_3$ | $CH_3$ | H | | $-C(CH_3)_2CH_2CH_3$ |
| $CH_3$ | $CH_3$ | H | | $-C(CH_3)_2CH_2CH_3$ |
| $CH_3$ | $CH_3$ | 6-$CH_3$ | $-(CH_2)_4-CH(OCH_3)-$ | $CH_3$ |
| $CH_3$ | $CH_3$ | 6-$CH_3$ | $-(CH_2)_3-CH(OCH_3)-CH_2-$ | $CH_3$ |
| $CH_3$ | $CH_3$ | 6-$CH_3$ | $-(CH_2)_2-CH(OCH_3)-(CH_2)_2-$ | $CH_3$ |
| $CH_3$ | $CH_3$ | 6-$CH_3$ | $-(CH_2)_2-CH(OC_2H_5)-(CH_2)_2-$ | $CH_3$ |
| $CH_3$ | $CH_3$ | 6-$CH_3$ | $-(CH_2)_2-CH(OC_3H_7)-(CH_2)_2-$ | $CH_3$ |
| $CH_3$ | $CH_3$ | 6-$CH_3$ | $-(CH_2)_2-CH(O-i-C_3H_7)-(CH_2)_2-$ | $CH_3$ |
| $CH_3$ | $CH_3$ | 6-$CH_3$ | $-(CH_2)_2-CH(O-t-C_4H_9)-(CH_2)_2-$ | $CH_3$ |
| $CH_3$ | $CH_3$ | 6-$CH_3$ | $-(CH_2)_3-CH(SCH_3)-CH_2-$ | $CH_3$ |
| $CH_3$ | $CH_3$ | 6-$CH_3$ | $-(CH_2)_2-CH(SCH_3)-(CH_2)_2-$ | $CH_3$ |

TABLE 2-continued

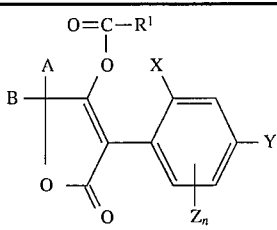
(Ib)

| X | Y | $Z_n$ | A | B | $R^1$ |
|---|---|---|---|---|---|
| $CH_3$ | $CH_3$ | 6-$CH_3$ | 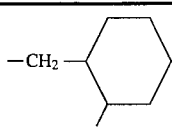 | | $CH_3$ |
| $CH_3$ | $CH_3$ | 6-$CH_3$ | 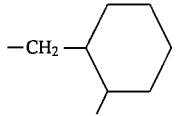 | | $CH_3$ |
| $CH_3$ | $CH_3$ | 6-$CH_3$ | 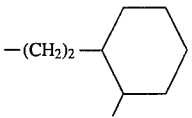 | | $CH_3$ |
| $CH_3$ | $CH_3$ | 6-$CH_3$ | 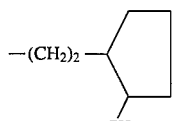 | | $CH_3$ |
| $CH_3$ | $CH_3$ | 6-$CH_3$ | 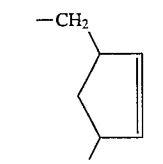 | | $CH_3$ |
| $CH_3$ | $CH_3$ | 6-$CH_3$ | 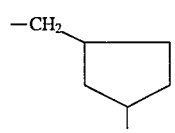 | | $CH_3$ |
| $CH_3$ | $CH_3$ | 6-$CH_3$ | 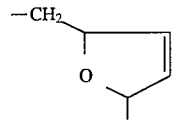 | | $CH_3$ |
| $CH_3$ | $CH_3$ | 6-$CH_3$ | 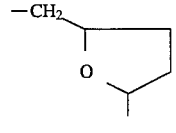 | | $CH_3$ |
| $CH_3$ | $CH_3$ | 6-$CH_3$ | $-(CH_2)_4-CH(OCH_3)-$ | | i-$C_3H_7$ |
| $CH_3$ | $CH_3$ | 6-$CH_3$ | $-(CH_2)_3-CH(OCH_3)-CH_2-$ | | i-$C_3H_7$ |
| $CH_3$ | $CH_3$ | 6-$CH_3$ | $-(CH_2)_2-CH(OCH_3)-(CH_2)_2-$ | | i-$C_3H_7$ |
| $CH_3$ | $CH_3$ | 6-$CH_3$ | $-(CH_2)_2-CH(OC_2H_5)-(CH_2)_2-$ | | i-$C_3H_7$ |
| $CH_3$ | $CH_3$ | 6-$CH_3$ | $-(CH_2)_2-CH(OC_3H_7)-(CH_2)_2-$ | | i-$C_3H_7$ |
| $CH_3$ | $CH_3$ | 6-$CH_3$ | $-(CH_2)_2-CH(O\text{-}i\text{-}C_3H_7)-(CH_2)_2-$ | | i-$C_3H_7$ |
| $CH_3$ | $CH_3$ | 6-$CH_3$ | $-(CH_2)_2-CH(O\text{-}t\text{-}C_4H_9)-(CH_2)_2-$ | | i-$C_3H_7$ |
| $CH_3$ | $CH_3$ | 6-$CH_3$ | $-(CH_2)_3-CH(SCH_3)-CH_2-$ | | i-$C_3H_7$ |
| $CH_3$ | $CH_3$ | 6-$CH_3$ | $-(CH_2)_2-CH(SCH_3)-(CH_2)_2-$ | | i-$C_3H_7$ |

TABLE 2-continued

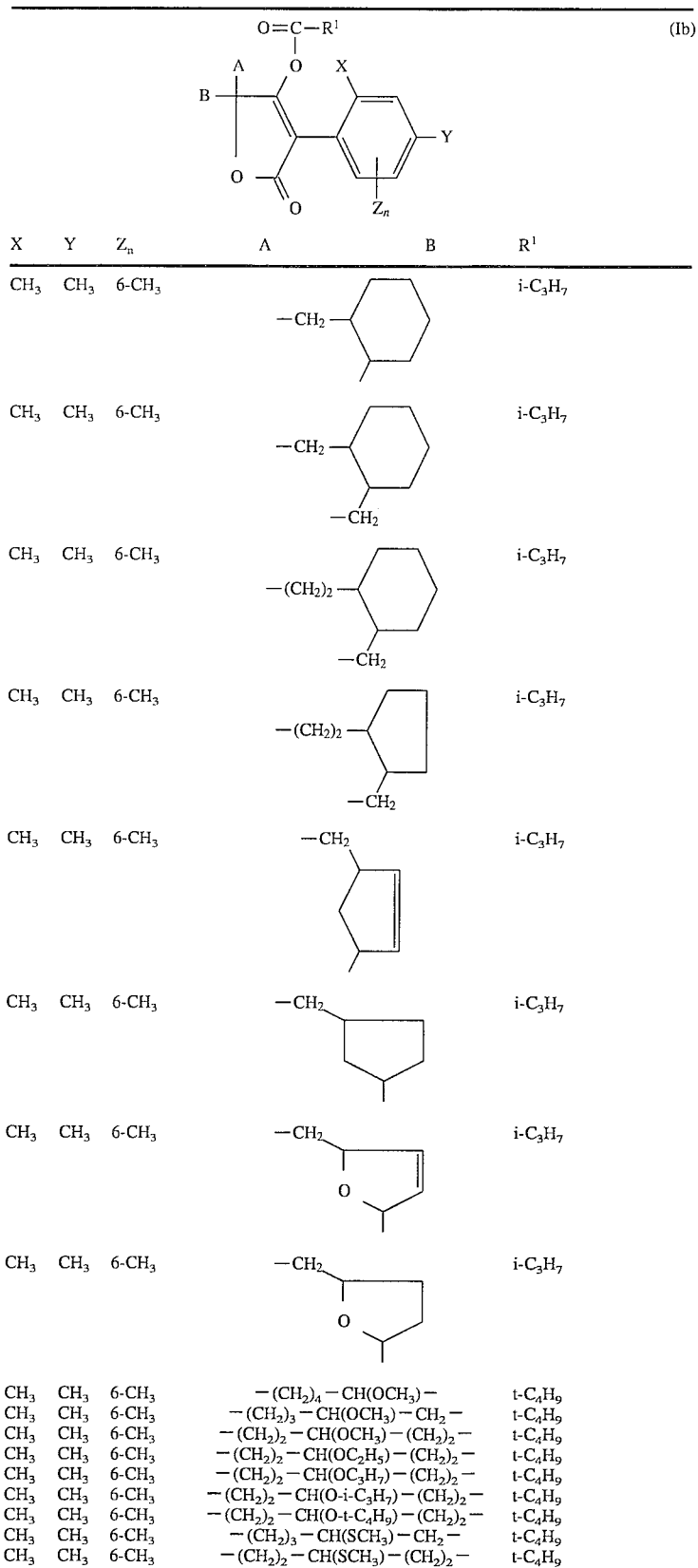

| X | Y | Z_n | A | B | R¹ |
|---|---|-----|---|---|-----|
| CH₃ | CH₃ | 6-CH₃ | —CH₂-(3-methylcyclohexyl) | | i-C₃H₇ |
| CH₃ | CH₃ | 6-CH₃ | —CH₂-(cyclohexyl)-CH₂— | | i-C₃H₇ |
| CH₃ | CH₃ | 6-CH₃ | —(CH₂)₂-(cyclohexyl)-CH₂— | | i-C₃H₇ |
| CH₃ | CH₃ | 6-CH₃ | —(CH₂)₂-(cyclopentyl)-CH₂— | | i-C₃H₇ |
| CH₃ | CH₃ | 6-CH₃ | —CH₂-(cyclohexenyl)- | | i-C₃H₇ |
| CH₃ | CH₃ | 6-CH₃ | —CH₂-(cyclopentyl)- | | i-C₃H₇ |
| CH₃ | CH₃ | 6-CH₃ | —CH₂-(2,5-dihydrofuranyl)- | | i-C₃H₇ |
| CH₃ | CH₃ | 6-CH₃ | —CH₂-(tetrahydrofuranyl)- | | i-C₃H₇ |
| CH₃ | CH₃ | 6-CH₃ | —(CH₂)₄—CH(OCH₃)— | | t-C₄H₉ |
| CH₃ | CH₃ | 6-CH₃ | —(CH₂)₃—CH(OCH₃)—CH₂— | | t-C₄H₉ |
| CH₃ | CH₃ | 6-CH₃ | —(CH₂)₂—CH(OCH₃)—(CH₂)₂— | | t-C₄H₉ |
| CH₃ | CH₃ | 6-CH₃ | —(CH₂)₂—CH(OC₂H₅)—(CH₂)₂— | | t-C₄H₉ |
| CH₃ | CH₃ | 6-CH₃ | —(CH₂)₂—CH(OC₃H₇)—(CH₂)₂— | | t-C₄H₉ |
| CH₃ | CH₃ | 6-CH₃ | —(CH₂)₂—CH(O-i-C₃H₇)—(CH₂)₂— | | t-C₄H₉ |
| CH₃ | CH₃ | 6-CH₃ | —(CH₂)₂—CH(O-t-C₄H₉)—(CH₂)₂— | | t-C₄H₉ |
| CH₃ | CH₃ | 6-CH₃ | —(CH₂)₃—CH(SCH₃)—CH₂— | | t-C₄H₉ |
| CH₃ | CH₃ | 6-CH₃ | —(CH₂)₂—CH(SCH₃)—(CH₂)₂— | | t-C₄H₉ |

TABLE 2-continued (Ib)

| X | Y | $Z_n$ | A | B | $R^1$ |
|---|---|---|---|---|---|
| $CH_3$ | $CH_3$ | 6-$CH_3$ | —$CH_2$–(methylcyclohexyl) | | t-$C_4H_9$ |
| $CH_3$ | $CH_3$ | 6-$CH_3$ | —$CH_2$– and —$CH_2$– (cyclohexane-1,2-diyl) | | t-$C_4H_9$ |
| $CH_3$ | $CH_3$ | 6-$CH_3$ | —$(CH_2)_2$– and —$CH_2$– (cyclohexane-1,2-diyl) | | t-$C_4H_9$ |
| $CH_3$ | $CH_3$ | 6-$CH_3$ | —$(CH_2)_2$– and —$CH_2$– (cyclopentane-1,2-diyl) | | t-$C_4H_9$ |
| $CH_3$ | $CH_3$ | 6-$CH_3$ | —$CH_2$– (cyclopentenyl, methyl substituted) | | t-$C_4H_9$ |
| $CH_3$ | $CH_3$ | 6-$CH_3$ | —$CH_2$– (methylcyclopentyl) | | t-$C_4H_9$ |
| $CH_3$ | $CH_3$ | 6-$CH_3$ | —$CH_2$– (2,5-dihydrofuranyl) | | t-$C_4H_9$ |
| $CH_3$ | $CH_3$ | 6-$CH_3$ | —$CH_2$– (tetrahydrofuranyl) | | t-$C_4H_9$ |
| $CH_3$ | $CH_3$ | 6-$CH_3$ | —$(CH_2)_4$—CH($OCH_3$)— | | —C($CH_3$)$_2$CH$_2$Cl |
| $CH_3$ | $CH_3$ | 6-$CH_3$ | —$(CH_2)_3$—CH($OCH_3$)—$CH_2$— | | —C($CH_3$)$_2$CH$_2$Cl |
| $CH_3$ | $CH_3$ | 6-$CH_3$ | —$(CH_2)_2$—CH($OCH_3$)—$(CH_2)_2$— | | —C($CH_3$)$_2$CH$_2$Cl |
| $CH_3$ | $CH_3$ | 6-$CH_3$ | —$(CH_2)_2$—CH($OC_2H_5$)—$(CH_2)_2$— | | —C($CH_3$)$_2$CH$_2$Cl |
| $CH_3$ | $CH_3$ | 6-$CH_3$ | —$(CH_2)_2$—CH($OC_3H_7$)—$(CH_2)_2$— | | —C($CH_3$)$_2$CH$_2$Cl |
| $CH_3$ | $CH_3$ | 6-$CH_3$ | —$(CH_2)_2$—CH(O-i-$C_3H_7$)—$(CH_2)_2$— | | —C($CH_3$)$_2$CH$_2$Cl |
| $CH_3$ | $CH_3$ | 6-$CH_3$ | —$(CH_2)_2$—CH(O-t-$C_4H_9$)—$(CH_2)_2$— | | —C($CH_3$)$_2$CH$_2$Cl |
| $CH_3$ | $CH_3$ | 6-$CH_3$ | —$(CH_2)_3$—CH($SCH_3$)—$CH_2$— | | —C($CH_3$)$_2$CH$_2$Cl |
| $CH_3$ | $CH_3$ | 6-$CH_3$ | —$(CH_2)_2$—CH($SCH_3$)—$(CH_2)_2$— | | —C($CH_3$)$_2$CH$_2$Cl |

TABLE 2-continued

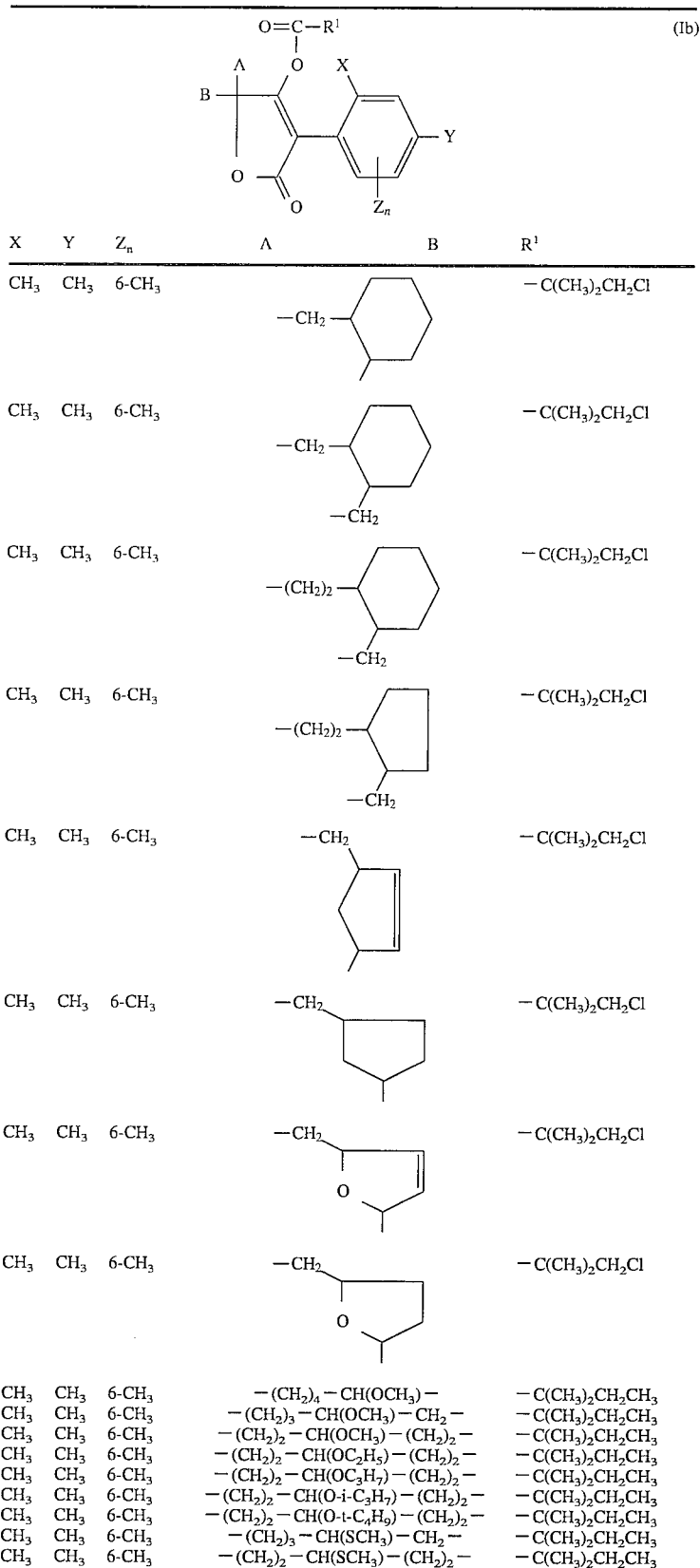

(Ib)

| X | Y | $Z_n$ | A | B | $R^1$ |
|---|---|---|---|---|---|
| $CH_3$ | $CH_3$ | 6-$CH_3$ | $-CH_2-$(methylcyclohexyl) | | $-C(CH_3)_2CH_2Cl$ |
| $CH_3$ | $CH_3$ | 6-$CH_3$ | $-CH_2-$(cyclohexyl)$-CH_2-$ | | $-C(CH_3)_2CH_2Cl$ |
| $CH_3$ | $CH_3$ | 6-$CH_3$ | $-(CH_2)_2-$(cyclohexyl)$-CH_2-$ | | $-C(CH_3)_2CH_2Cl$ |
| $CH_3$ | $CH_3$ | 6-$CH_3$ | $-(CH_2)_2-$(cyclopentyl)$-CH_2-$ | | $-C(CH_3)_2CH_2Cl$ |
| $CH_3$ | $CH_3$ | 6-$CH_3$ | $-CH_2-$(cyclopentenyl) | | $-C(CH_3)_2CH_2Cl$ |
| $CH_3$ | $CH_3$ | 6-$CH_3$ | $-CH_2-$(cyclopentyl) | | $-C(CH_3)_2CH_2Cl$ |
| $CH_3$ | $CH_3$ | 6-$CH_3$ | $-CH_2-$(dihydrofuranyl) | | $-C(CH_3)_2CH_2Cl$ |
| $CH_3$ | $CH_3$ | 6-$CH_3$ | $-CH_2-$(tetrahydrofuranyl) | | $-C(CH_3)_2CH_2Cl$ |
| $CH_3$ | $CH_3$ | 6-$CH_3$ | $-(CH_2)_4-CH(OCH_3)-$ | | $-C(CH_3)_2CH_2CH_3$ |
| $CH_3$ | $CH_3$ | 6-$CH_3$ | $-(CH_2)_3-CH(OCH_3)-CH_2-$ | | $-C(CH_3)_2CH_2CH_3$ |
| $CH_3$ | $CH_3$ | 6-$CH_3$ | $-(CH_2)_2-CH(OCH_3)-(CH_2)_2-$ | | $-C(CH_3)_2CH_2CH_3$ |
| $CH_3$ | $CH_3$ | 6-$CH_3$ | $-(CH_2)_2-CH(OC_2H_5)-(CH_2)_2-$ | | $-C(CH_3)_2CH_2CH_3$ |
| $CH_3$ | $CH_3$ | 6-$CH_3$ | $-(CH_2)_2-CH(OC_3H_7)-(CH_2)_2-$ | | $-C(CH_3)_2CH_2CH_3$ |
| $CH_3$ | $CH_3$ | 6-$CH_3$ | $-(CH_2)_2-CH(O\text{-}i\text{-}C_3H_7)-(CH_2)_2-$ | | $-C(CH_3)_2CH_2CH_3$ |
| $CH_3$ | $CH_3$ | 6-$CH_3$ | $-(CH_2)_2-CH(O\text{-}t\text{-}C_4H_9)-(CH_2)_2-$ | | $-C(CH_3)_2CH_2CH_3$ |
| $CH_3$ | $CH_3$ | 6-$CH_3$ | $-(CH_2)_3-CH(SCH_3)-CH_2-$ | | $-C(CH_3)_2CH_2CH_3$ |
| $CH_3$ | $CH_3$ | 6-$CH_3$ | $-(CH_2)_2-CH(SCH_3)-(CH_2)_2-$ | | $-C(CH_3)_2CH_2CH_3$ |

TABLE 2-continued (Ib)

$$O=C-R^1$$ structure with A, B substituents on the enol carbon, aryl group with X, Y, $Z_n$ substituents.

| X | Y | $Z_n$ | A | B | $R^1$ |
|---|---|---|---|---|---|
| CH₃ | CH₃ | 6-CH₃ | –CH₂– | cyclohexyl | –C(CH₃)₂CH₂CH₃ |
| CH₃ | CH₃ | 6-CH₃ | –CH₂– | –CH₂– (cyclohexane-1,2-diyl) | –C(CH₃)₂CH₂CH₃ |
| CH₃ | CH₃ | 6-CH₃ | –(CH₂)₂– | –CH₂– (cyclohexane) | –C(CH₃)₂CH₂CH₃ |
| CH₃ | CH₃ | 6-CH₃ | –(CH₂)₂– | –CH₂– (cyclopentane) | –C(CH₃)₂CH₂CH₃ |
| CH₃ | CH₃ | 6-CH₃ | –CH₂– | cyclopentenyl | –C(CH₃)₂CH₂CH₃ |
| CH₃ | CH₃ | 6-CH₃ | –CH₂– | cyclopentyl | –C(CH₃)₂CH₂CH₃ |
| CH₃ | CH₃ | 6-CH₃ | –CH₂– | 2,5-dihydrofuranyl | –C(CH₃)₂CH₂CH₃ |
| CH₃ | CH₃ | 6-CH₃ | –CH₂– | tetrahydrofuranyl | –C(CH₃)₂CH₂CH₃ |

The following 3-aryl-4-hydroxy-$\Delta^3$-dihydrofuranone derivatives of the formula (Ic) may be mentioned individually in addition to the compounds mentioned in the preparation examples:

TABLE 3

(Structure Ic: substituted phenyl with L=C-M-R² group, O-linked ring containing A-B, and C(=O)-O group)

| X | Y | Z_n | A | B | L | M | R² |
|---|---|---|---|---|---|---|---|
| Cl | Cl | H | —(CH$_2$)$_4$—CH(OCH$_3$)— | | O | O | C$_2$H$_5$ |
| Cl | Cl | H | —(CH$_2$)$_3$—CH(OCH$_3$)—CH$_2$— | | O | O | C$_2$H$_5$ |
| Cl | Cl | H | —(CH$_2$)$_2$—CH(OCH$_3$)—(CH$_2$)$_2$— | | O | O | C$_2$H$_5$ |
| Cl | Cl | H | —(CH$_2$)$_2$—CH(OC$_2$H$_5$)—(CH$_2$)$_2$— | | O | O | C$_2$H$_5$ |
| Cl | Cl | H | —(CH$_2$)$_2$—CH(OC$_3$H$_7$)—(CH$_2$)$_2$— | | O | O | C$_2$H$_5$ |
| Cl | Cl | H | —(CH$_2$)$_2$—CH(O-i-C$_3$H$_7$)—(CH$_2$)$_2$— | | O | O | C$_2$H$_5$ |
| Cl | Cl | H | —(CH$_2$)$_2$—CH(O-t-C$_4$H$_9$)—(CH$_2$)$_2$— | | O | O | C$_2$H$_5$ |
| Cl | Cl | H | —(CH$_2$)$_3$—CH(SCH$_3$)—CH$_2$— | | O | O | C$_2$H$_5$ |
| Cl | Cl | H | —(CH$_2$)$_2$—CH(SCH$_3$)—(CH$_2$)$_2$— | | O | O | C$_2$H$_5$ |
| Cl | Cl | H | —CH$_2$-(methylcyclohexyl) | | O | O | C$_2$H$_5$ |
| Cl | Cl | H | —CH$_2$-cyclohexyl-CH$_2$— | | O | O | C$_2$H$_5$ |
| Cl | Cl | H | —(CH$_2$)$_2$-cyclohexyl-CH$_2$— | | O | O | C$_2$H$_5$ |
| Cl | Cl | H | —(CH$_2$)$_2$-cyclopentyl-CH$_2$— | | O | O | C$_2$H$_5$ |
| Cl | Cl | H | —CH$_2$-(cyclopentenyl-methyl) | | O | O | C$_2$H$_5$ |
| Cl | Cl | H | —CH$_2$-(cyclopentyl-methyl) | | O | O | C$_2$H$_5$ |
| Cl | Cl | H | —CH$_2$-(2,5-dihydrofuranyl-methyl) | | O | O | C$_2$H$_5$ |
| Cl | Cl | H | —CH$_2$-(tetrahydrofuranyl-methyl) | | O | O | C$_2$H$_5$ |
| Cl | Cl | H | —(CH$_2$)$_4$—CH(OCH$_3$)— | | O | O | i-C$_3$H$_7$ |
| Cl | Cl | H | —(CH$_2$)$_3$—CH(OCH$_3$)—CH$_2$— | | O | O | i-C$_3$H$_7$ |

TABLE 3-continued

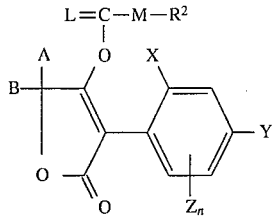
(Ic)

| X | Y | $Z_n$ | A | B | L | M | $R^2$ |
|---|---|---|---|---|---|---|---|
| Cl | Cl | H | —(CH$_2$)$_2$—CH(OCH$_3$)—(CH$_2$)$_2$— | | O | O | i-C$_3$H$_7$ |
| Cl | Cl | H | —(CH$_2$)$_2$—CH(OC$_2$H$_5$)—(CH$_2$)$_2$— | | O | O | i-C$_3$H$_7$ |
| Cl | Cl | H | —(CH$_2$)$_2$—CH(OC$_3$H$_7$)—(CH$_2$)$_2$— | | O | O | i-C$_3$H$_7$ |
| Cl | Cl | H | —(CH$_2$)$_2$—CH(O-i-C$_3$H$_7$)—(CH$_2$)$_2$— | | O | O | i-C$_3$H$_7$ |
| Cl | Cl | H | —(CH$_2$)$_2$—CH(O-t-C$_4$H$_9$)—(CH$_2$)$_2$— | | O | O | i-C$_3$H$_7$ |
| Cl | Cl | H | —(CH$_2$)$_3$—CH(SCH$_3$)—CH$_2$— | | O | O | i-C$_3$H$_7$ |
| Cl | Cl | H | —(CH$_2$)$_2$—CH(SCH$_3$)—(CH$_2$)$_2$— | | O | O | i-C$_3$H$_7$ |
| Cl | Cl | H | 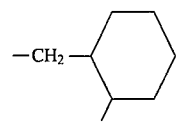 | | O | O | i-C$_3$H$_7$ |
| Cl | Cl | H | 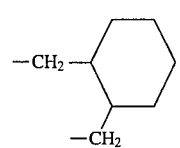 | | O | O | i-C$_3$H$_7$ |
| Cl | Cl | H | 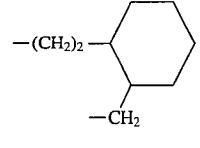 | | O | O | i-C$_3$H$_7$ |
| Cl | Cl | H | 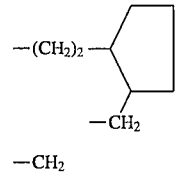 | | O | O | i-C$_3$H$_7$ |
| Cl | Cl | H | 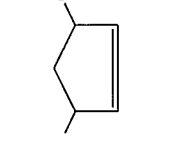 | | O | O | i-C$_3$H$_7$ |
| Cl | Cl | H | 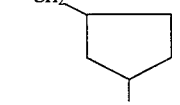 | | O | O | i-C$_3$H$_7$ |
| Cl | Cl | H | 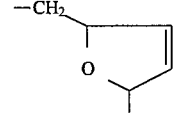 | | O | O | i-C$_3$H$_7$ |
| Cl | Cl | H | 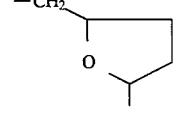 | | O | O | i-C$_3$H$_7$ |
| Cl | Cl | H | —(CH$_2$)$_4$—CH(OCH$_3$)— | | O | S | i-C$_3$H$_7$ |
| Cl | Cl | H | —(CH$_2$)$_3$—CH(OCH$_3$)—CH$_2$— | | O | S | i-C$_3$H$_7$ |
| Cl | Cl | H | —(CH$_2$)$_2$—CH(OCH$_3$)—(CH$_2$)$_2$— | | O | S | i-C$_3$H$_7$ |
| Cl | Cl | H | —(CH$_2$)$_2$—CH(OC$_2$H$_5$)—(CH$_2$)$_2$— | | O | S | i-C$_3$H$_7$ |

TABLE 3-continued $$\text{(Ic)}$$

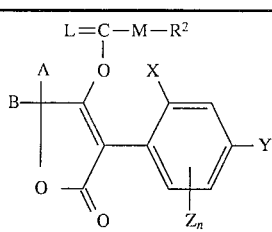

| X | Y | $Z_n$ | A B | L | M | $R^2$ |
|---|---|---|---|---|---|---|
| Cl | Cl | H | —(CH$_2$)$_2$—CH(OC$_3$H$_7$)—(CH$_2$)$_2$— | O | S | i-C$_3$H$_7$ |
| Cl | Cl | H | —(CH$_2$)$_2$—CH(O-i-C$_3$H$_7$)—(CH$_2$)$_2$— | O | S | i-C$_3$H$_7$ |
| Cl | Cl | H | —(CH$_2$)$_2$—CH(O-t-C$_4$H$_9$)—(CH$_2$)$_2$— | O | S | i-C$_3$H$_7$ |
| Cl | Cl | H | —(CH$_2$)$_3$—CH(SCH$_3$)—CH$_2$— | O | S | i-C$_3$H$_7$ |
| Cl | Cl | H | —(CH$_2$)$_2$—CH(SCH$_3$)—(CH$_2$)$_2$— | O | S | i-C$_3$H$_7$ |
| Cl | Cl | H | 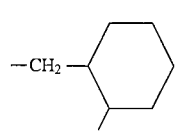 | O | S | i-C$_3$H$_7$ |
| Cl | Cl | H | 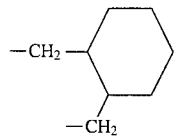 | O | S | i-C$_3$H$_7$ |
| Cl | Cl | H | 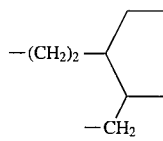 | O | S | i-C$_3$H$_7$ |
| Cl | Cl | H | 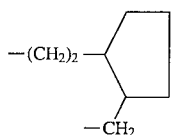 | O | S | i-C$_3$H$_7$ |
| Cl | Cl | H | 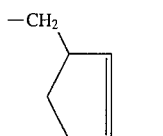 | O | S | i-C$_3$H$_7$ |
| Cl | Cl | H |  | O | S | i-C$_3$H$_7$ |
| Cl | Cl | H |  | O | S | i-C$_3$H$_7$ |
| Cl | Cl | H | 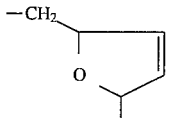 | O | S | i-C$_3$H$_7$ |
| Cl | Cl | H | —(CH$_2$)$_4$—CH(OCH$_3$)— | O | O | i-C$_4$H$_9$ |
| Cl | Cl | H | —(CH$_2$)$_3$—CH(OCH$_3$)—CH$_2$— | O | O | i-C$_4$H$_9$ |
| Cl | Cl | H | —(CH$_2$)$_2$—CH(OCH$_3$)—(CH$_2$)$_2$— | O | O | i-C$_4$H$_9$ |
| Cl | Cl | H | —(CH$_2$)$_2$—CH(OC$_2$H$_5$)—(CH$_2$)$_2$— | O | O | i-C$_4$H$_9$ |
| Cl | Cl | H | —(CH$_2$)$_2$—CH(OC$_3$H$_7$)—(CH$_2$)$_2$— | O | O | i-C$_4$H$_9$ |
| Cl | Cl | H | —(CH$_2$)$_2$—CH(O-i-C$_3$H$_7$)—(CH$_2$)$_2$— | O | O | i-C$_4$H$_9$ |

TABLE 3-continued

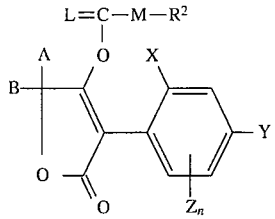
(Ic)

| X | Y | $Z_n$ | A B | L | M | $R^2$ |
|---|---|---|---|---|---|---|
| Cl | Cl | H | $-(CH_2)_2-CH(O\text{-}t\text{-}C_4H_9)-(CH_2)_2-$ | O | O | i-$C_4H_9$ |
| Cl | Cl | H | $-(CH_2)_3-CH(SCH_3)-CH_2-$ | O | O | i-$C_4H_9$ |
| Cl | Cl | H | $-(CH_2)_2-CH(SCH_3)-(CH_2)_2-$ | O | O | i-$C_4H_9$ |
| Cl | Cl | H | 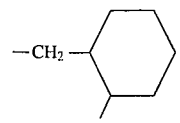 | O | O | i-$C_4H_9$ |
| Cl | Cl | H | 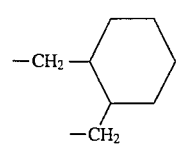 | O | O | i-$C_4H_9$ |
| Cl | Cl | H | 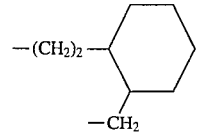 | O | O | i-$C_4H_9$ |
| Cl | Cl | H | 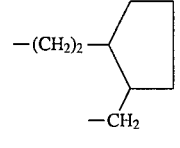 | O | O | i-$C_4H_9$ |
| Cl | Cl | H | 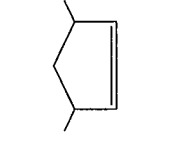 | O | O | i-$C_4H_9$ |
| Cl | Cl | H | 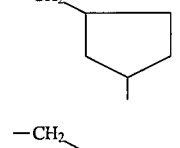 | O | O | i-$C_4H_9$ |
| Cl | Cl | H | 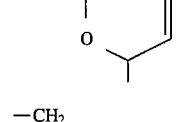 | O | O | i-$C_4H_7$ |
| Cl | Cl | H | 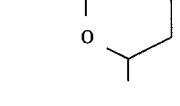 | O | O | i-$C_4H_7$ |
| Cl | Cl | H | $-(CH_2)_4-CH(OCH_3)-$ | O | O | s-$C_4H_9$ |
| Cl | Cl | H | $-(CH_2)_3-CH(OCH_3)-CH_2-$ | O | O | s-$C_4H_9$ |
| Cl | Cl | H | $-(CH_2)_2-CH(OCH_3)-(CH_2)_2-$ | O | O | s-$C_4H_9$ |
| Cl | Cl | H | $-(CH_2)_2-CH(OC_2H_5)-(CH_2)_2-$ | O | O | s-$C_4H_9$ |
| Cl | Cl | H | $-(CH_2)_2-CH(OC_3H_7)-(CH_2)_2-$ | O | O | s-$C_4H_9$ |
| Cl | Cl | H | $-(CH_2)_2-CH(O\text{-}i\text{-}C_3H_7)-(CH_2)_2-$ | O | O | s-$C_4H_9$ |
| Cl | Cl | H | $-(CH_2)_2-CH(O\text{-}t\text{-}C_4H_9)-(CH_2)_2-$ | O | O | s-$C_4H_9$ |
| Cl | Cl | H | $-(CH_2)_3-CH(SCH_3)-CH_2-$ | O | O | s-$C_4H_9$ |

TABLE 3-continued

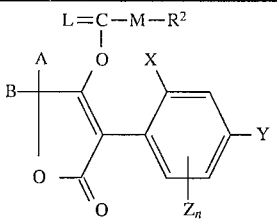

(Ic)

| X | Y | $Z_n$ | A B | L | M | $R^2$ |
|---|---|---|---|---|---|---|
| Cl | Cl | H | —(CH$_2$)$_2$—CH(SCH$_3$)—(CH$_2$)$_2$— | O | O | s-C$_4$H$_9$ |
| Cl | Cl | H | 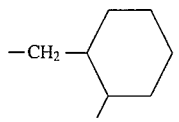 | O | O | s-C$_4$H$_9$ |
| Cl | Cl | H | 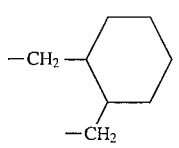 | O | O | s-C$_4$H$_9$ |
| Cl | Cl | H | 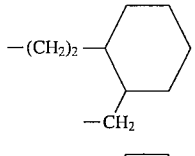 | O | O | s-C$_4$H$_9$ |
| Cl | Cl | H | 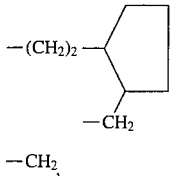 | O | O | s-C$_4$H$_9$ |
| Cl | Cl | H | 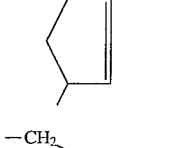 | O | O | s-C$_4$H$_9$ |
| Cl | Cl | H | 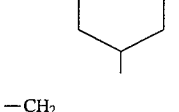 | O | O | s-C$_4$H$_9$ |
| Cl | Cl | H | 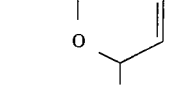 | O | O | s-C$_4$H$_9$ |
| Cl | Cl | H | 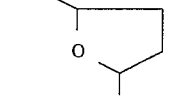 | O | O | s-C$_4$H$_9$ |
| CH$_3$ | CH$_3$ | H | —(CH$_2$)$_4$—CH(OCH$_3$)— | O | O | C$_2$H$_5$ |
| CH$_3$ | CH$_3$ | H | —(CH$_2$)$_3$—CH(OCH$_3$)—CH$_2$— | O | O | C$_2$H$_5$ |
| CH$_3$ | CH$_3$ | H | —(CH$_2$)$_2$—CH(OCH$_3$)—(CH$_2$)$_2$— | O | O | C$_2$H$_5$ |
| CH$_3$ | CH$_3$ | H | —(CH$_2$)$_2$—CH(OC$_2$H$_5$)—(CH$_2$)$_2$— | O | O | C$_2$H$_5$ |
| CH$_3$ | CH$_3$ | H | —(CH$_2$)$_2$—CH(OC$_3$H$_7$)—(CH$_2$)$_2$— | O | O | C$_2$H$_5$ |
| CH$_3$ | CH$_3$ | H | —(CH$_2$)$_2$—CH(O-i-C$_3$H$_7$)—(CH$_2$)$_2$— | O | O | C$_2$H$_5$ |
| CH$_3$ | CH$_3$ | H | —(CH$_2$)$_2$—CH(O-t-C$_4$H$_9$)—(CH$_2$)$_2$— | O | O | C$_2$H$_5$ |
| CH$_3$ | CH$_3$ | H | —(CH$_2$)$_3$—CH(SCH$_3$)—CH$_2$— | O | O | C$_2$H$_5$ |
| CH$_3$ | CH$_3$ | H | —(CH$_2$)$_2$—CH(SCH$_3$)—(CH$_2$)$_2$— | O | O | C$_2$H$_5$ |

TABLE 3-continued $$\text{(Ic)}$$

| X | Y | $Z_n$ | A | B | L | M | $R^2$ |
|---|---|---|---|---|---|---|---|
| CH$_3$ | CH$_3$ | H | \multicolumn{2}{l|}{—CH$_2$—(cyclohexyl)} | O | O | C$_2$H$_5$ |
| CH$_3$ | CH$_3$ | H | \multicolumn{2}{l|}{—CH$_2$—(cyclohexyl)—CH$_2$—} | O | O | C$_2$H$_5$ |
| CH$_3$ | CH$_3$ | H | \multicolumn{2}{l|}{—(CH$_2$)$_2$—(cyclohexyl)—CH$_2$—} | O | O | C$_2$H$_5$ |
| CH$_3$ | CH$_3$ | H | \multicolumn{2}{l|}{—(CH$_2$)$_2$—(cyclopentyl)—CH$_2$—} | O | O | C$_2$H$_5$ |
| CH$_3$ | CH$_3$ | H | \multicolumn{2}{l|}{—CH$_2$—(cyclopentenyl)—} | O | O | C$_2$H$_5$ |
| CH$_3$ | CH$_3$ | H | \multicolumn{2}{l|}{—CH$_2$—(cyclopentyl)—} | O | O | C$_2$H$_5$ |
| CH$_3$ | CH$_3$ | H | \multicolumn{2}{l|}{—CH$_2$—(dihydrofuryl)—} | O | O | C$_2$H$_5$ |
| CH$_3$ | CH$_3$ | H | \multicolumn{2}{l|}{—CH$_2$—(tetrahydrofuryl)—} | O | O | C$_2$H$_5$ |
| CH$_3$ | CH$_3$ | H | \multicolumn{2}{l|}{—(CH$_2$)$_4$—CH(OCH$_3$)—} | O | O | i-C$_3$H$_7$ |
| CH$_3$ | CH$_3$ | H | \multicolumn{2}{l|}{—(CH$_2$)$_3$—CH(OCH$_3$)—CH$_2$—} | O | O | i-C$_3$H$_7$ |
| CH$_3$ | CH$_3$ | H | \multicolumn{2}{l|}{—(CH$_2$)$_2$—CH(OCH$_3$)—(CH$_2$)$_2$—} | O | O | i-C$_3$H$_7$ |
| CH$_3$ | CH$_3$ | H | \multicolumn{2}{l|}{—(CH$_2$)$_2$—CH(OC$_2$H$_5$)—(CH$_2$)$_2$—} | O | O | i-C$_3$H$_7$ |
| CH$_3$ | CH$_3$ | H | \multicolumn{2}{l|}{—(CH$_2$)$_2$—CH(OC$_3$H$_7$)—(CH$_2$)$_2$—} | O | O | i-C$_3$H$_7$ |
| CH$_3$ | CH$_3$ | H | \multicolumn{2}{l|}{—(CH$_2$)$_2$—CH(O-i-C$_3$H$_7$)—(CH$_2$)$_2$—} | O | O | i-C$_3$H$_7$ |
| CH$_3$ | CH$_3$ | H | \multicolumn{2}{l|}{—(CH$_2$)$_2$—CH(O-t-C$_4$H$_9$)—(CH$_2$)$_2$—} | O | O | i-C$_3$H$_7$ |
| CH$_3$ | CH$_3$ | H | \multicolumn{2}{l|}{—(CH$_2$)$_3$—CH(SCH$_3$)—CH$_2$—} | O | O | i-C$_3$H$_7$ |
| CH$_3$ | CH$_3$ | H | \multicolumn{2}{l|}{—(CH$_2$)$_2$—CH(SCH$_3$)—(CH$_2$)$_2$—} | O | O | i-C$_3$H$_7$ |

TABLE 3-continued

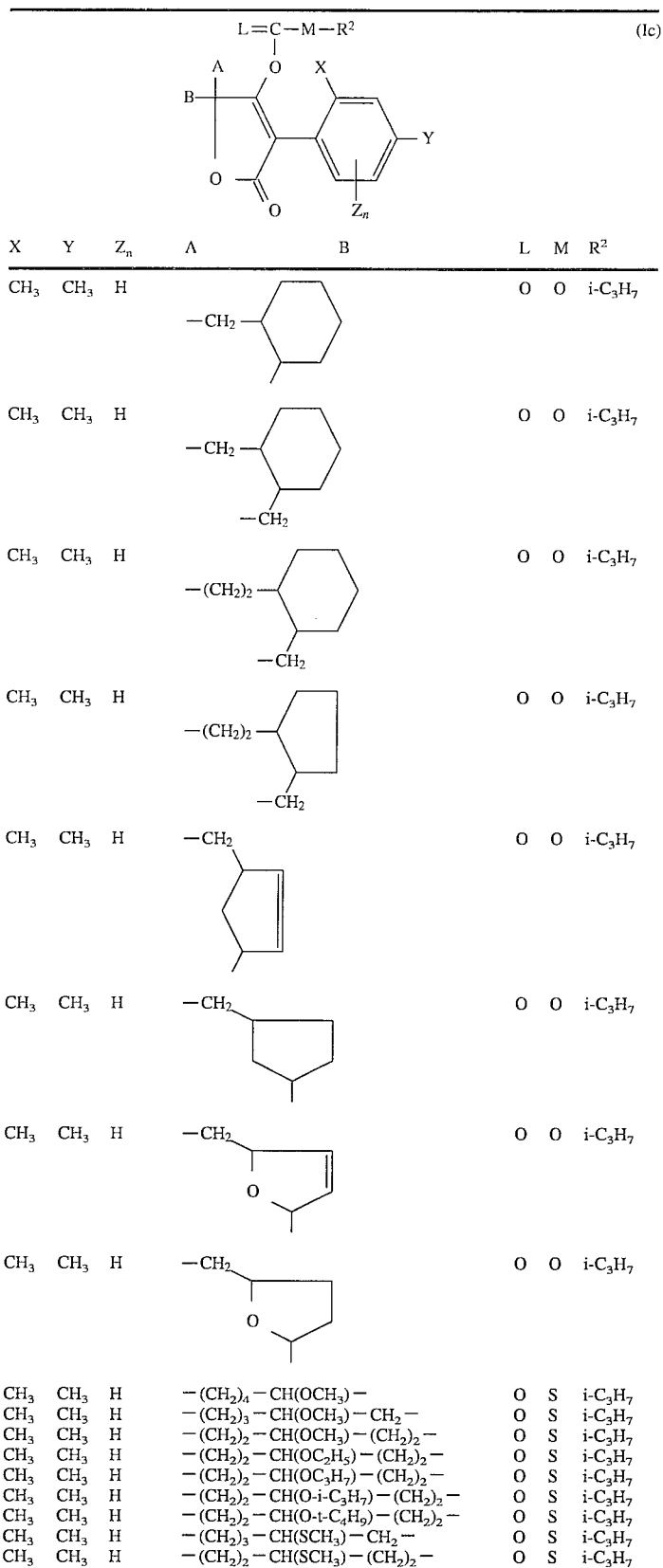

| X | Y | Z$_n$ | A | B | L | M | R$^2$ |
|---|---|---|---|---|---|---|---|
| CH$_3$ | CH$_3$ | H | \multicolumn{2}{c|}{—CH$_2$–(2-methylcyclohexyl)} | O | O | i-C$_3$H$_7$ |
| CH$_3$ | CH$_3$ | H | \multicolumn{2}{c|}{—CH$_2$–cyclohexyl–CH$_2$—} | O | O | i-C$_3$H$_7$ |
| CH$_3$ | CH$_3$ | H | \multicolumn{2}{c|}{—(CH$_2$)$_2$–cyclohexyl–CH$_2$—} | O | O | i-C$_3$H$_7$ |
| CH$_3$ | CH$_3$ | H | \multicolumn{2}{c|}{—(CH$_2$)$_2$–cyclopentyl–CH$_2$—} | O | O | i-C$_3$H$_7$ |
| CH$_3$ | CH$_3$ | H | \multicolumn{2}{c|}{—CH$_2$–cyclopentenyl–} | O | O | i-C$_3$H$_7$ |
| CH$_3$ | CH$_3$ | H | \multicolumn{2}{c|}{—CH$_2$–(3-methylcyclopentyl)} | O | O | i-C$_3$H$_7$ |
| CH$_3$ | CH$_3$ | H | \multicolumn{2}{c|}{—CH$_2$–dihydrofuryl–} | O | O | i-C$_3$H$_7$ |
| CH$_3$ | CH$_3$ | H | \multicolumn{2}{c|}{—CH$_2$–tetrahydrofuryl–} | O | O | i-C$_3$H$_7$ |
| CH$_3$ | CH$_3$ | H | \multicolumn{2}{c|}{—(CH$_2$)$_4$—CH(OCH$_3$)—} | O | S | i-C$_3$H$_7$ |
| CH$_3$ | CH$_3$ | H | \multicolumn{2}{c|}{—(CH$_2$)$_3$—CH(OCH$_3$)—CH$_2$—} | O | S | i-C$_3$H$_7$ |
| CH$_3$ | CH$_3$ | H | \multicolumn{2}{c|}{—(CH$_2$)$_2$—CH(OCH$_3$)—(CH$_2$)$_2$—} | O | S | i-C$_3$H$_7$ |
| CH$_3$ | CH$_3$ | H | \multicolumn{2}{c|}{—(CH$_2$)$_2$—CH(OC$_2$H$_5$)—(CH$_2$)$_2$—} | O | S | i-C$_3$H$_7$ |
| CH$_3$ | CH$_3$ | H | \multicolumn{2}{c|}{—(CH$_2$)$_2$—CH(OC$_3$H$_7$)—(CH$_2$)$_2$—} | O | S | i-C$_3$H$_7$ |
| CH$_3$ | CH$_3$ | H | \multicolumn{2}{c|}{—(CH$_2$)$_2$—CH(O-i-C$_3$H$_7$)—(CH$_2$)$_2$—} | O | S | i-C$_3$H$_7$ |
| CH$_3$ | CH$_3$ | H | \multicolumn{2}{c|}{—(CH$_2$)$_2$—CH(O-t-C$_4$H$_9$)—(CH$_2$)$_2$—} | O | S | i-C$_3$H$_7$ |
| CH$_3$ | CH$_3$ | H | \multicolumn{2}{c|}{—(CH$_2$)$_3$—CH(SCH$_3$)—CH$_2$—} | O | S | i-C$_3$H$_7$ |
| CH$_3$ | CH$_3$ | H | \multicolumn{2}{c|}{—(CH$_2$)$_2$—CH(SCH$_3$)—(CH$_2$)$_2$—} | O | S | i-C$_3$H$_7$ |

TABLE 3-continued $$\text{(Ic)}$$

| X | Y | $Z_n$ | A | B | L | M | $R^2$ |
|---|---|---|---|---|---|---|---|
| $CH_3$ | $CH_3$ | H | \multicolumn{2}{l|}{$-CH_2-$(2-methylcyclohexyl)} | O | S | $i-C_3H_7$ |
| $CH_3$ | $CH_3$ | H | \multicolumn{2}{l|}{$-CH_2-$(cyclohexane-1,2-diyl)$-CH_2-$} | O | S | $i-C_3H_7$ |
| $CH_3$ | $CH_3$ | H | \multicolumn{2}{l|}{$-(CH_2)_2-$(cyclohexane-1,2-diyl)$-CH_2-$} | O | S | $i-C_3H_7$ |
| $CH_3$ | $CH_3$ | H | \multicolumn{2}{l|}{$-(CH_2)_2-$(cyclopentane-1,3-diyl)$-CH_2-$} | O | S | $i-C_3H_7$ |
| $CH_3$ | $CH_3$ | H | \multicolumn{2}{l|}{$-CH_2-$(cyclopent-3-ene-1,3-diyl)} | O | S | $i-C_3H_7$ |
| $CH_3$ | $CH_3$ | H | \multicolumn{2}{l|}{$-CH_2-$(cyclopentane-1,3-diyl)} | O | S | $i-C_3H_7$ |
| $CH_3$ | $CH_3$ | H | \multicolumn{2}{l|}{$-CH_2-$(2,5-dihydrofuran-2,5-diyl)} | O | S | $i-C_3H_7$ |
| $CH_3$ | $CH_3$ | H | \multicolumn{2}{l|}{$-CH_2-$(tetrahydrofuran-2,5-diyl)} | O | S | $i-C_3H_7$ |
| $CH_3$ | $CH_3$ | H | \multicolumn{2}{l|}{$-(CH_2)_4-CH(OCH_3)-$} | O | O | $i-C_4H_9$ |
| $CH_3$ | $CH_3$ | H | \multicolumn{2}{l|}{$-(CH_2)_3-CH(OCH_3)-CH_2-$} | O | O | $i-C_4H_9$ |
| $CH_3$ | $CH_3$ | H | \multicolumn{2}{l|}{$-(CH_2)_2-CH(OCH_3)-(CH_2)_2-$} | O | O | $i-C_4H_9$ |
| $CH_3$ | $CH_3$ | H | \multicolumn{2}{l|}{$-(CH_2)_2-CH(OC_2H_5)-(CH_2)_2-$} | O | O | $i-C_4H_9$ |
| $CH_3$ | $CH_3$ | H | \multicolumn{2}{l|}{$-(CH_2)_2-CH(OC_3H_7)-(CH_2)_2-$} | O | O | $i-C_4H_9$ |
| $CH_3$ | $CH_3$ | H | \multicolumn{2}{l|}{$-(CH_2)_2-CH(O-i-C_3H_7)-(CH_2)_2-$} | O | O | $i-C_4H_9$ |
| $CH_3$ | $CH_3$ | H | \multicolumn{2}{l|}{$-(CH_2)_2-CH(O-t-C_4H_9)-(CH_2)_2-$} | O | O | $i-C_4H_9$ |
| $CH_3$ | $CH_3$ | H | \multicolumn{2}{l|}{$-(CH_2)_3-CH(SCH_3)-CH_2-$} | O | O | $i-C_4H_9$ |
| $CH_3$ | $CH_3$ | H | \multicolumn{2}{l|}{$-(CH_2)_2-CH(SCH_3)-(CH_2)_2-$} | O | O | $i-C_4H_9$ |

TABLE 3-continued

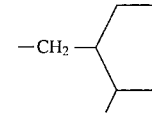

(Ic)

| X | Y | $Z_n$ | A | B | L | M | $R^2$ |
|---|---|---|---|---|---|---|---|
| $CH_3$ | $CH_3$ | H | | 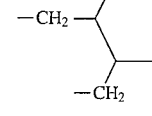 | O | O | $i-C_4H_9$ |
| $CH_3$ | $CH_3$ | H | | 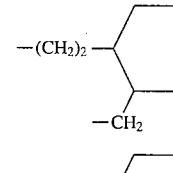 | O | O | $i-C_4H_9$ |
| $CH_3$ | $CH_3$ | H | | 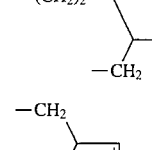 | O | O | $i-C_4H_9$ |
| $CH_3$ | $CH_3$ | H | | 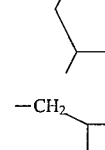 | O | O | $i-C_4H_9$ |
| $CH_3$ | $CH_3$ | H | | 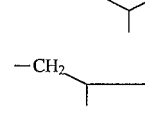 | O | O | $i-C_4H_9$ |
| $CH_3$ | $CH_3$ | H | | 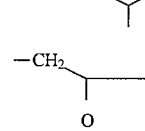 | O | O | $i-C_4H_9$ |
| $CH_3$ | $CH_3$ | H | | 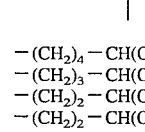 | O | O | $i-C_4H_9$ |
| $CH_3$ | $CH_3$ | H | | 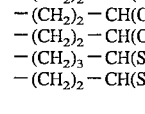 | O | O | $i-C_4H_9$ |
| $CH_3$ | $CH_3$ | H | $-(CH_2)_4-CH(OCH_3)-$ | | O | O | $s-C_4H_9$ |
| $CH_3$ | $CH_3$ | H | $-(CH_2)_3-CH(OCH_3)-CH_2-$ | | O | O | $s-C_4H_9$ |
| $CH_3$ | $CH_3$ | H | $-(CH_2)_2-CH(OCH_3)-(CH_2)_2-$ | | O | O | $s-C_4H_9$ |
| $CH_3$ | $CH_3$ | H | $-(CH_2)_2-CH(OC_2H_5)-(CH_2)_2-$ | | O | O | $s-C_4H_9$ |
| $CH_3$ | $CH_3$ | H | $-(CH_2)_2-CH(OC_3H_7)-(CH_2)_2-$ | | O | O | $s-C_4H_9$ |
| $CH_3$ | $CH_3$ | H | $-(CH_2)_2-CH(O-i-C_3H_7)-(CH_2)_2-$ | | O | O | $s-C_4H_9$ |
| $CH_3$ | $CH_3$ | H | $-(CH_2)_2-CH(O-t-C_4H_9)-(CH_2)_2-$ | | O | O | $s-C_4H_9$ |
| $CH_3$ | $CH_3$ | H | $-(CH_2)_3-CH(SCH_3)-CH_2-$ | | O | O | $s-C_4H_9$ |
| $CH_3$ | $CH_3$ | H | $-(CH_2)_2-CH(SCH_3)-(CH_2)_2-$ | | O | O | $s-C_4H_9$ |

TABLE 3-continued

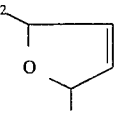
(Ic)

| X | Y | Z_n | A | B | L | M | R² |
|---|---|---|---|---|---|---|---|
| CH₃ | CH₃ | H | —CH₂— | 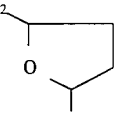 | O | S | i-C₃H₇ |
| CH₃ | CH₃ | H | —CH₂— | 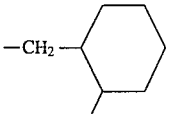 | O | S | i-C₃H₇ |
| CH₃ | CH₃ | H | —(CH₂)₄—CH(OCH₃)— | | O | O | i-C₄H₉ |
| CH₃ | CH₃ | H | —(CH₂)₃—CH(OCH₃)—CH₂— | | O | O | i-C₄H₉ |
| CH₃ | CH₃ | H | —(CH₂)₂—CH(OCH₃)—(CH₂)₂— | | O | O | i-C₄H₉ |
| CH₃ | CH₃ | H | —(CH₂)₂—CH(OC₂H₅)—(CH₂)₂— | | O | O | i-C₄H₉ |
| CH₃ | CH₃ | H | —(CH₂)₂—CH(OC₃H₇)—(CH₂)₂— | | O | O | i-C₄H₉ |
| CH₃ | CH₃ | H | —(CH₂)₂—CH(O-i-C₃H₇)—(CH₂)₂— | | O | O | i-C₄H₉ |
| CH₃ | CH₃ | H | —(CH₂)₂—CH(O-t-C₄H₉)—(CH₂)₂— | | O | O | i-C₄H₉ |
| CH₃ | CH₃ | H | —(CH₂)₃—CH(SCH₃)—CH₂— | | O | O | i-C₄H₉ |
| CH₃ | CH₃ | H | —(CH₂)₂—CH(SCH₃)—(CH₂)₂— | | O | O | i-C₄H₉ |
| CH₃ | CH₃ | H | —CH₂— | 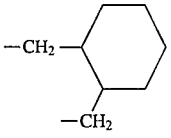 | O | O | i-C₄H₉ |
| CH₃ | CH₃ | H | —CH₂— —CH₂— | 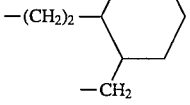 | O | O | i-C₄H₉ |
| CH₃ | CH₃ | H | —(CH₂)₂— —CH₂— | 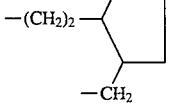 | O | O | i-C₄H₉ |
| CH₃ | CH₃ | H | —(CH₂)₂— —CH₂— | 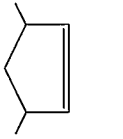 | O | O | i-C₄H₉ |
| CH₃ | CH₃ | H | —CH₂— | 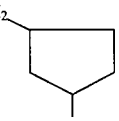 | O | O | i-C₄H₉ |
| CH₃ | CH₃ | H | —CH₂— | | O | O | i-C₄H₉ |

TABLE 3-continued

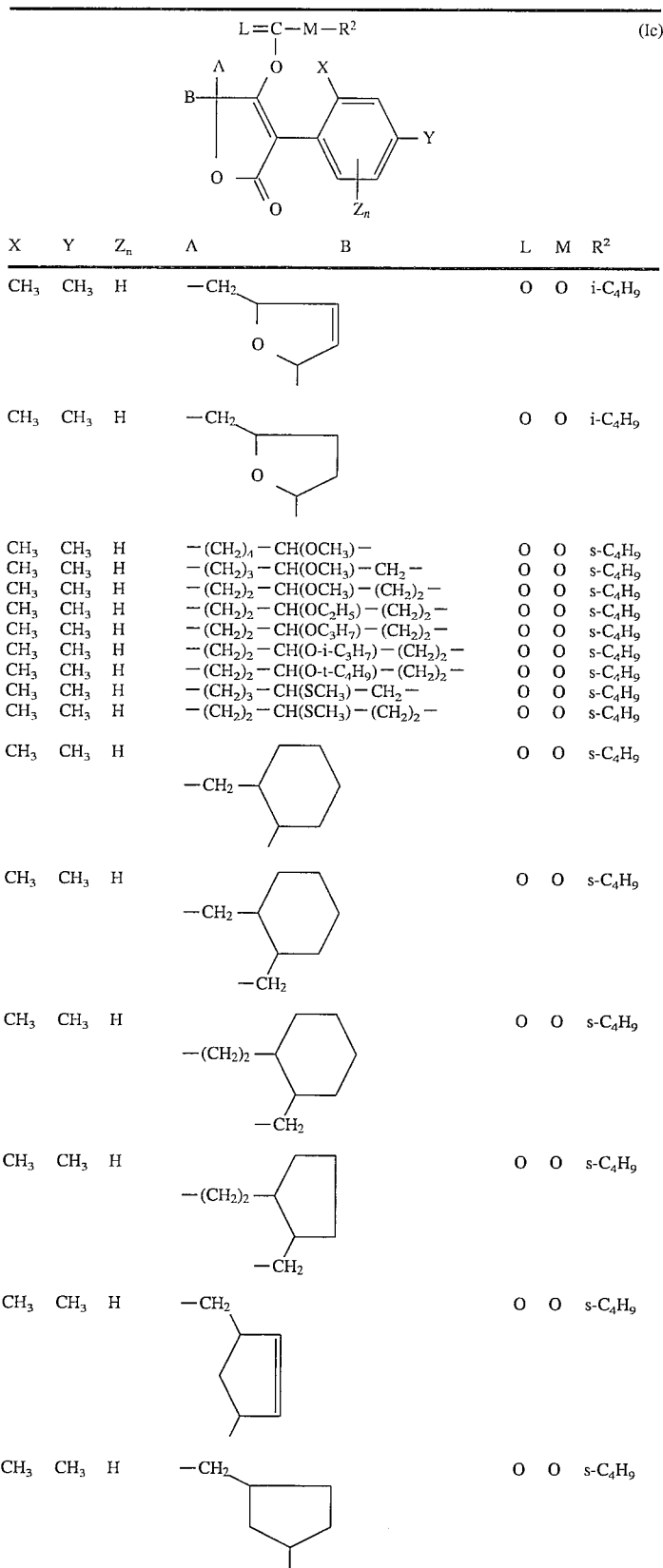

| X | Y | Z_n | A | B | L | M | R² |
|---|---|---|---|---|---|---|---|
| $CH_3$ | $CH_3$ | H | $-CH_2$— (2H-furan ring) | | O | O | $i-C_4H_9$ |
| $CH_3$ | $CH_3$ | H | $-CH_2$— (tetrahydrofuran ring) | | O | O | $i-C_4H_9$ |
| $CH_3$ | $CH_3$ | H | $-(CH_2)_4-CH(OCH_3)-$ | | O | O | $s-C_4H_9$ |
| $CH_3$ | $CH_3$ | H | $-(CH_2)_3-CH(OCH_3)-CH_2-$ | | O | O | $s-C_4H_9$ |
| $CH_3$ | $CH_3$ | H | $-(CH_2)_2-CH(OCH_3)-(CH_2)_2-$ | | O | O | $s-C_4H_9$ |
| $CH_3$ | $CH_3$ | H | $-(CH_2)_2-CH(OC_2H_5)-(CH_2)_2-$ | | O | O | $s-C_4H_9$ |
| $CH_3$ | $CH_3$ | H | $-(CH_2)_2-CH(OC_3H_7)-(CH_2)_2-$ | | O | O | $s-C_4H_9$ |
| $CH_3$ | $CH_3$ | H | $-(CH_2)_2-CH(O\text{-}i\text{-}C_3H_7)-(CH_2)_2-$ | | O | O | $s-C_4H_9$ |
| $CH_3$ | $CH_3$ | H | $-(CH_2)_2-CH(O\text{-}t\text{-}C_4H_9)-(CH_2)_2-$ | | O | O | $s-C_4H_9$ |
| $CH_3$ | $CH_3$ | H | $-(CH_2)_3-CH(SCH_3)-CH_2-$ | | O | O | $s-C_4H_9$ |
| $CH_3$ | $CH_3$ | H | $-(CH_2)_2-CH(SCH_3)-(CH_2)_2-$ | | O | O | $s-C_4H_9$ |
| $CH_3$ | $CH_3$ | H | $-CH_2$— (cyclohexyl) | | O | O | $s-C_4H_9$ |
| $CH_3$ | $CH_3$ | H | $-CH_2$—cyclohexyl—$-CH_2$ | | O | O | $s-C_4H_9$ |
| $CH_3$ | $CH_3$ | H | $-(CH_2)_2$—cyclohexyl—$-CH_2$ | | O | O | $s-C_4H_9$ |
| $CH_3$ | $CH_3$ | H | $-(CH_2)_2$—cyclopentyl—$-CH_2$ | | O | O | $s-C_4H_9$ |
| $CH_3$ | $CH_3$ | H | $-CH_2$— (cyclopentenyl) | | O | O | $s-C_4H_9$ |
| $CH_3$ | $CH_3$ | H | $-CH_2$— (methylcyclopentyl) | | O | O | $s-C_4H_9$ |

TABLE 3-continued $$L=C-M-R^2$$
(structure Ic: phenyl ring with substituents X (ortho), Y (para), $Z_n$; attached to =C(O-)- group with spiro ring containing A and B, and a C(=O)O- group)

| X | Y | $Z_n$ | A | B | L | M | $R^2$ |
|---|---|---|---|---|---|---|---|
| CH₃ | CH₃ | H | —CH₂— | (2,5-dihydrofuran-2-yl, 5-methyl) | O | O | s-C₄H₉ |
| CH₃ | CH₃ | H | —CH₂— | (tetrahydrofuran-2-yl, 5-methyl) | O | O | s-C₄H₉ |
| CH₃ | CH₃ | 6-CH₃ | —(CH₂)₄—CH(OCH₃)— | | O | O | C₂H₅ |
| CH₃ | CH₃ | 6-CH₃ | —(CH₂)₃—CH(OCH₃)—CH₂— | | O | O | C₂H₅ |
| CH₃ | CH₃ | 6-CH₃ | —(CH₂)₂—CH(OCH₃)—(CH₂)₂— | | O | O | C₂H₅ |
| CH₃ | CH₃ | 6-CH₃ | —(CH₂)₂—CH(OC₂H₅)—(CH₂)₂— | | O | O | C₂H₅ |
| CH₃ | CH₃ | 6-CH₃ | —(CH₂)₂—CH(OC₃H₇)—(CH₂)₂— | | O | O | C₂H₅ |
| CH₃ | CH₃ | 6-CH₃ | —(CH₂)₂—CH(O-i-C₃H₇)—(CH₂)₂— | | O | O | C₂H₅ |
| CH₃ | CH₃ | 6-CH₃ | —(CH₂)₂—CH(O-t-C₄H₉)—(CH₂)₂— | | O | O | C₂H₅ |
| CH₃ | CH₃ | 6-CH₃ | —(CH₂)₃—CH(SCH₃)—CH₂— | | O | O | C₂H₅ |
| CH₃ | CH₃ | 6-CH₃ | —(CH₂)₂—CH(SCH₃)—(CH₂)₂— | | O | O | C₂H₅ |
| CH₃ | CH₃ | 6-CH₃ | —CH₂—(2-methylcyclohexyl) | | O | O | C₂H₅ |
| CH₃ | CH₃ | 6-CH₃ | —CH₂—(cyclohexane-1,2-diyl)—CH₂— | | O | O | C₂H₅ |
| CH₃ | CH₃ | 6-CH₃ | —(CH₂)₂—(cyclohexane-1,2-diyl)—CH₂— | | O | O | C₂H₅ |
| CH₃ | CH₃ | 6-CH₃ | —(CH₂)₂—(cyclopentane-1,2-diyl)—CH₂— | | O | O | C₂H₅ |
| CH₃ | CH₃ | 6-CH₃ | —CH₂—(4-methylcyclohex-2-en-1-yl) | | O | O | C₂H₅ |
| CH₃ | CH₃ | 6-CH₃ | —CH₂—(3-methylcyclopentyl) | | O | O | C₂H₅ |

TABLE 3-continued $$\text{(Ic)}$$

Structure: L=C(O-M-R²)-C(A,B)(connected via O-C(=O) ring) with phenyl group bearing X, Y, Z_n substituents.

| X | Y | Z_n | A | B | L | M | R² |
|---|---|---|---|---|---|---|---|
| CH₃ | CH₃ | 6-CH₃ | —CH₂— | (2,5-dihydrofuran-2-yl) | O | O | C₂H₅ |
| CH₃ | CH₃ | 6-CH₃ | —CH₂— | (tetrahydrofuran-2-yl) | O | O | C₂H₅ |
| CH₃ | CH₃ | 6-CH₃ | —(CH₂)₄—CH(OCH₃)— | | O | O | i-C₃H₇ |
| CH₃ | CH₃ | 6-CH₃ | —(CH₂)₃—CH(OCH₃)—CH₂— | | O | O | i-C₃H₇ |
| CH₃ | CH₃ | 6-CH₃ | —(CH₂)₂—CH(OCH₃)—(CH₂)₂— | | O | O | i-C₃H₇ |
| CH₃ | CH₃ | 6-CH₃ | —(CH₂)₂—CH(OC₂H₅)—(CH₂)₂— | | O | O | i-C₃H₇ |
| CH₃ | CH₃ | 6-CH₃ | —(CH₂)₂—CH(OC₃H₇)—(CH₂)₂— | | O | O | i-C₃H₇ |
| CH₃ | CH₃ | 6-CH₃ | —(CH₂)₂—CH(O-i-C₃H₇)—(CH₂)₂— | | O | O | i-C₃H₇ |
| CH₃ | CH₃ | 6-CH₃ | —(CH₂)₂—CH(O-t-C₄H₉)—(CH₂)₂— | | O | O | i-C₃H₇ |
| CH₃ | CH₃ | 6-CH₃ | —(CH₂)₃—CH(SCH₃)—CH₂— | | O | O | i-C₃H₇ |
| CH₃ | CH₃ | 6-CH₃ | —(CH₂)₂—CH(SCH₃)—(CH₂)₂— | | O | O | i-C₃H₇ |
| CH₃ | CH₃ | 6-CH₃ | —CH₂—(2-methylcyclohexyl) | | O | O | i-C₃H₇ |
| CH₃ | CH₃ | 6-CH₃ | —CH₂—(cyclohexane-1,2-diyl)—CH₂— | | O | O | i-C₃H₇ |
| CH₃ | CH₃ | 6-CH₃ | —(CH₂)₂—(cyclohexane-1,2-diyl)—CH₂— | | O | O | i-C₃H₇ |
| CH₃ | CH₃ | 6-CH₃ | —(CH₂)₂—(cyclopentane-1,2-diyl)—CH₂— | | O | O | i-C₃H₇ |
| CH₃ | CH₃ | 6-CH₃ | —CH₂—(4-methylcyclopent-2-en-1-yl) | | O | O | i-C₃H₇ |
| CH₃ | CH₃ | 6-CH₃ | —CH₂—(3-methylcyclopentyl) | | O | O | i-C₃H₇ |

TABLE 3-continued $$\text{(Ic)}$$

| X | Y | $Z_n$ | A | B | L | M | $R^2$ |
|---|---|---|---|---|---|---|---|
| $CH_3$ | $CH_3$ | 6-$CH_3$ | —$CH_2$— | (2,5-dihydrofuran-2,5-diyl) | O | O | i-$C_3H_7$ |
| $CH_3$ | $CH_3$ | 6-$CH_3$ | —$CH_2$— | (tetrahydrofuran-2,5-diyl) | O | O | i-$C_3H_7$ |
| $CH_3$ | $CH_3$ | 6-$CH_3$ | —$(CH_2)_4$—CH($OCH_3$)— | | O | S | i-$C_3H_7$ |
| $CH_3$ | $CH_3$ | 6-$CH_3$ | —$(CH_2)_3$—CH($OCH_3$)—$CH_2$— | | O | S | i-$C_3H_7$ |
| $CH_3$ | $CH_3$ | 6-$CH_3$ | —$(CH_2)_2$—CH($OCH_3$)—$(CH_2)_2$— | | O | S | i-$C_3H_7$ |
| $CH_3$ | $CH_3$ | 6-$CH_3$ | —$(CH_2)_2$—CH($OC_2H_5$)—$(CH_2)_2$— | | O | S | i-$C_3H_7$ |
| $CH_3$ | $CH_3$ | 6-$CH_3$ | —$(CH_2)_2$—CH($OC_3H_7$)—$(CH_2)_2$— | | O | S | i-$C_3H_7$ |
| $CH_3$ | $CH_3$ | 6-$CH_3$ | —$(CH_2)_2$—CH(O-i-$C_3H_7$)—$(CH_2)_2$— | | O | S | i-$C_3H_7$ |
| $CH_3$ | $CH_3$ | 6-$CH_3$ | —$(CH_2)_2$—CH(O-t-$C_4H_9$)—$(CH_2)_2$— | | O | S | i-$C_3H_7$ |
| $CH_3$ | $CH_3$ | 6-$CH_3$ | —$(CH_2)_3$—CH($SCH_3$)—$CH_2$— | | O | S | i-$C_3H_7$ |
| $CH_3$ | $CH_3$ | 6-$CH_3$ | —$(CH_2)_2$—CH($SCH_3$)—$(CH_2)_2$— | | O | S | i-$C_3H_7$ |
| $CH_3$ | $CH_3$ | 6-$CH_3$ | —$CH_2$—(2-methylcyclohexyl) | | O | S | i-$C_3H_7$ |
| $CH_3$ | $CH_3$ | 6-$CH_3$ | —$CH_2$—(cyclohexane-1,2-diyl)—$CH_2$— | | O | S | i-$C_3H_7$ |
| $CH_3$ | $CH_3$ | 6-$CH_3$ | —$(CH_2)_2$—(cyclohexane-1,2-diyl)—$CH_2$— | | O | S | i-$C_3H_7$ |
| $CH_3$ | $CH_3$ | 6-$CH_3$ | —$(CH_2)_2$—(cyclopentane-1,2-diyl)—$CH_2$— | | O | S | i-$C_3H_7$ |
| $CH_3$ | $CH_3$ | 6-$CH_3$ | —$CH_2$—(4-methyl-2-cyclopentenyl) | | O | S | i-$C_3H_7$ |
| $CH_3$ | $CH_3$ | 6-$CH_3$ | —$CH_2$—(3-methylcyclopentyl) | | O | S | i-$C_3H_7$ |

TABLE 3-continued

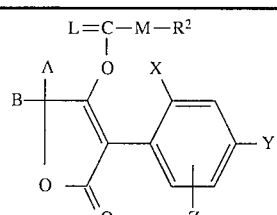
(Ic)

| X | Y | $Z_n$ | A | B | L | M | $R^2$ |
|---|---|---|---|---|---|---|---|
| $CH_3$ | $CH_3$ | 6-$CH_3$ | $-CH_2-$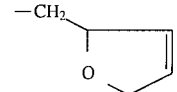 | | O | S | i-$C_3H_7$ |
| $CH_3$ | $CH_3$ | 6-$CH_3$ | $-CH_2-$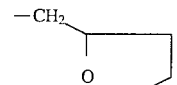 | | O | S | i-$C_3H_7$ |
| $CH_3$ | $CH_3$ | 6-$CH_3$ | $-(CH_2)_4-CH(OCH_3)-$ | | O | O | i-$C_4H_9$ |
| $CH_3$ | $CH_3$ | 6-$CH_3$ | $-(CH_2)_3-CH(OCH_3)-CH_2-$ | | O | O | i-$C_4H_9$ |
| $CH_3$ | $CH_3$ | 6-$CH_3$ | $-(CH_2)_2-CH(OCH_3)-(CH_2)_2-$ | | O | O | i-$C_4H_9$ |
| $CH_3$ | $CH_3$ | 6-$CH_3$ | $-(CH_2)_2-CH(OC_2H_5)-(CH_2)_2-$ | | O | O | i-$C_4H_9$ |
| $CH_3$ | $CH_3$ | 6-$CH_3$ | $-(CH_2)_2-CH(OC_3H_7)-(CH_2)_2-$ | | O | O | i-$C_4H_9$ |
| $CH_3$ | $CH_3$ | 6-$CH_3$ | $-(CH_2)_2-CH(O\text{-}i\text{-}C_3H_7)-(CH_2)_2-$ | | O | O | i-$C_4H_9$ |
| $CH_3$ | $CH_3$ | 6-$CH_3$ | $-(CH_2)_2-CH(O\text{-}t\text{-}C_4H_9)-(CH_2)_2-$ | | O | O | i-$C_4H_9$ |
| $CH_3$ | $CH_3$ | 6-$CH_3$ | $-(CH_2)_3-CH(SCH_3)-CH_2-$ | | O | O | i-$C_4H_9$ |
| $CH_3$ | $CH_3$ | 6-$CH_3$ | $-(CH_2)_2-CH(SCH_3)-(CH_2)_2-$ | | O | O | i-$C_4H_9$ |
| $CH_3$ | $CH_3$ | 6-$CH_3$ | 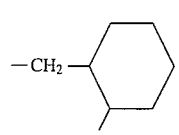 | | O | O | i-$C_4H_9$ |
| $CH_3$ | $CH_3$ | 6-$CH_3$ | 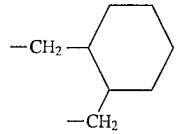 | | O | O | i-$C_4H_9$ |
| $CH_3$ | $CH_3$ | 6-$CH_3$ | 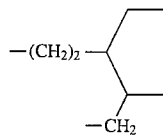 | | O | O | i-$C_4H_9$ |
| $CH_3$ | $CH_3$ | 6-$CH_3$ | 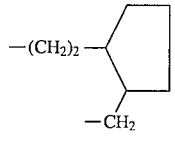 | | O | O | i-$C_4H_9$ |
| $CH_3$ | $CH_3$ | 6-$CH_3$ | $-CH_2$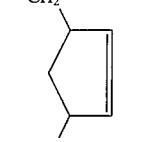 | | O | O | i-$C_4H_9$ |
| $CH_3$ | $CH_3$ | 6-$CH_3$ | $-CH_2$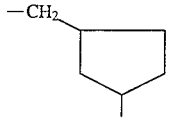 | | O | O | i-$C_4H_9$ |

TABLE 3-continued $$\text{(Ic)}$$

Structure (Ic): phenyl ring substituted with X (ortho), Y (para), $Z_n$; attached via a =C to an enol-lactone system with substituents A, B on a carbon bearing O and C(=O)O (forming a ring), and the enol oxygen connected to L=C-M-R².

| X | Y | $Z_n$ | A | B | L | M | R² |
|---|---|---|---|---|---|---|---|
| $CH_3$ | $CH_3$ | 6-$CH_3$ | -$CH_2$- | (2,5-dihydrofuran-2,5-diyl) | O | O | i-$C_4H_9$ |
| $CH_3$ | $CH_3$ | 6-$CH_3$ | -$CH_2$- | (tetrahydrofuran-2,5-diyl) | O | O | i-$C_4H_9$ |
| $CH_3$ | $CH_3$ | 6-$CH_3$ | -($CH_2$)$_4$-CH(OCH$_3$)- | | O | O | s-$C_4H_9$ |
| $CH_3$ | $CH_3$ | 6-$CH_3$ | -($CH_2$)$_3$-CH(OCH$_3$)-$CH_2$- | | O | O | s-$C_4H_9$ |
| $CH_3$ | $CH_3$ | 6-$CH_3$ | -($CH_2$)$_2$-CH(OCH$_3$)-($CH_2$)$_2$- | | O | O | s-$C_4H_9$ |
| $CH_3$ | $CH_3$ | 6-$CH_3$ | -($CH_2$)$_2$-CH(OC$_2$H$_5$)-($CH_2$)$_2$- | | O | O | s-$C_4H_9$ |
| $CH_3$ | $CH_3$ | 6-$CH_3$ | -($CH_2$)$_2$-CH(OC$_3$H$_7$)-($CH_2$)$_2$- | | O | O | s-$C_4H_9$ |
| $CH_3$ | $CH_3$ | 6-$CH_3$ | -($CH_2$)$_2$-CH(O-i-C$_3$H$_7$)-($CH_2$)$_2$- | | O | O | s-$C_4H_9$ |
| $CH_3$ | $CH_3$ | 6-$CH_3$ | -($CH_2$)$_2$-CH(O-t-C$_4$H$_9$)-($CH_2$)$_2$- | | O | O | s-$C_4H_9$ |
| $CH_3$ | $CH_3$ | 6-$CH_3$ | -($CH_2$)$_3$-CH(SCH$_3$)-$CH_2$- | | O | O | s-$C_4H_9$ |
| $CH_3$ | $CH_3$ | 6-$CH_3$ | -($CH_2$)$_2$-CH(SCH$_3$)-($CH_2$)$_2$- | | O | O | s-$C_4H_9$ |
| $CH_3$ | $CH_3$ | 6-$CH_3$ | -$CH_2$-(cyclohexane-1,2-diyl) | | O | O | s-$C_4H_9$ |
| $CH_3$ | $CH_3$ | 6-$CH_3$ | -$CH_2$-(cyclohexane-1,2-diyl)-$CH_2$- | | O | O | s-$C_4H_9$ |
| $CH_3$ | $CH_3$ | 6-$CH_3$ | -($CH_2$)$_2$-(cyclohexane-1,2-diyl)-$CH_2$- | | O | O | s-$C_4H_9$ |
| $CH_3$ | $CH_3$ | 6-$CH_3$ | -($CH_2$)$_2$-(cyclopentane-1,2-diyl)-$CH_2$- | | O | O | s-$C_4H_9$ |
| $CH_3$ | $CH_3$ | 6-$CH_3$ | -$CH_2$-(cyclopent-2-ene-1,4-diyl) | | O | O | s-$C_4H_9$ |
| $CH_3$ | $CH_3$ | 6-$CH_3$ | -$CH_2$-(cyclopentane-1,3-diyl) | | O | O | s-$C_4H_9$ |

TABLE 3-continued (Ic)

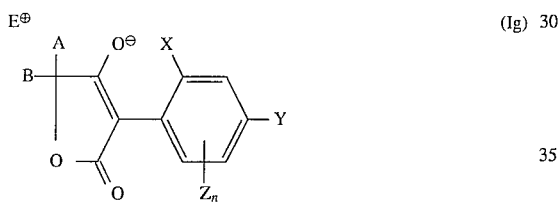

| X | Y | $Z_n$ | A | B | L | M | $R^2$ |
|---|---|---|---|---|---|---|---|
| $CH_3$ | $CH_3$ | 6-$CH_3$ | $-CH_2-$ | (2,5-dihydrofuranyl) | O | O | s-$C_4H_9$ |
| $CH_3$ | $CH_3$ | 6-$CH_3$ | $-CH_2-$ | (tetrahydrofuranyl) | O | O | s-$C_4H_9$ |

The following 3-aryl-4-hydroxy-$\Delta^3$-dihydrofuranone derivatives of the formula (Ig) may be mentioned individually in addition to the compounds mentioned in the preparation examples:

(Ig)

TABLE 4

| X | Y | $Z_n$ | A | B | $E^{\oplus}$ |
|---|---|---|---|---|---|
| Cl | Cl | H | $-(CH_2)_4-CH(OCH_3)-$ | | Na |
| Cl | Cl | H | $-(CH_2)_3-CH(OCH_3)-CH_2-$ | | Na |
| Cl | Cl | H | $-(CH_2)_2-CH(OCH_3)-(CH_2)_2-$ | | Na |
| Cl | Cl | H | $-(CH_2)_2-CH(OC_2H_5)-(CH_2)_2-$ | | Na |
| Cl | Cl | H | $-(CH_2)_2-CH(OC_3H_7)-(CH_2)_2-$ | | Na |
| Cl | Cl | H | $-(CH_2)_2-CH(O\text{-}i\text{-}C_3H_7)-(CH_2)_2-$ | | Na |
| Cl | Cl | H | $-(CH_2)_2-CH(O\text{-}t\text{-}C_4H_9)-(CH_2)_2-$ | | Na |
| Cl | Cl | H | $-(CH_2)_3-CH(SCH_3)-CH_2-$ | | Na |
| Cl | Cl | H | $-(CH_2)_2-CH(SCH_3)-(CH_2)_2-$ | | Na |
| Cl | Cl | H | $-CH_2-$(cyclohexyl) | | Na |
| Cl | Cl | H | $-CH_2-$(cyclohexyl)$-CH_2-$ | | Na |
| Cl | Cl | H | $-(CH_2)_2-$(cyclohexyl)$-CH_2-$ | | Na |

TABLE 4-continued

| X | Y | $Z_n$ | A | B | $E^{\oplus}$ |
|---|---|---|---|---|---|
| Cl | Cl | H | —(CH$_2$)$_2$— | 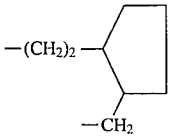 | Na |
| Cl | Cl | H | —CH$_2$— | 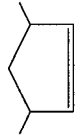 | Na |
| Cl | Cl | H | —CH$_2$— | 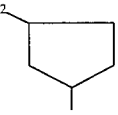 | Na |
| Cl | Cl | H | —CH$_2$— | 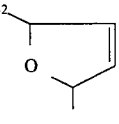 | Na |
| Cl | Cl | H | —CH$_2$— | 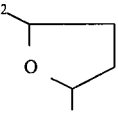 | Na |
| Cl | Cl | H | —(CH$_2$)$_4$—CH(OCH$_3$)— | | —NH$_3$-i-C$_3$H$_7$ |
| Cl | Cl | H | —(CH$_2$)$_3$—CH(OCH$_3$)—CH$_2$— | | —NH$_3$-i-C$_3$H$_7$ |
| Cl | Cl | H | —(CH$_2$)$_2$—CH(OCH$_3$)—(CH$_2$)$_2$— | | —NH$_3$-i-C$_3$H$_7$ |
| Cl | Cl | H | —(CH$_2$)$_2$—CH(OC$_2$H$_5$)—(CH$_2$)$_2$— | | —NH$_3$-i-C$_3$H$_7$ |
| Cl | Cl | H | —(CH$_2$)$_2$—CH(OC$_3$H$_7$)—(CH$_2$)$_2$— | | —NH$_3$-i-C$_3$H$_7$ |
| Cl | Cl | H | —(CH$_2$)$_2$—CH(O-i-C$_3$H$_7$)—(CH$_2$)$_2$— | | —NH$_3$-i-C$_3$H$_7$ |
| Cl | Cl | H | —(CH$_2$)$_2$—CH(O-t-C$_4$H$_9$)—(CH$_2$)$_2$— | | —NH$_3$-i-C$_3$H$_7$ |
| Cl | Cl | H | —(CH$_2$)$_3$—CH(SCH$_3$)—CH$_2$— | | —NH$_3$-i-C$_3$H$_7$ |
| Cl | Cl | H | —(CH$_2$)$_2$—CH(SCH$_3$)—(CH$_2$)$_2$— | | —NH$_3$-i-C$_3$H$_7$ |
| Cl | Cl | H | —CH$_2$— | 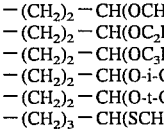 | —NH$_3$-i-C$_3$H$_7$ |
| Cl | Cl | H | —CH$_2$— | 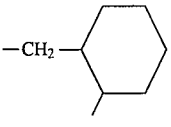 | —NH$_3$-i-C$_3$H$_7$ |
| Cl | Cl | H | —(CH$_2$)$_2$— | 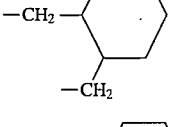 | —NH$_3$-i-C$_3$H$_7$ |
| Cl | Cl | H | —(CH$_2$)$_2$— | 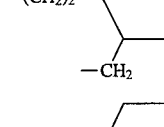 | —NH$_3$-i-C$_3$H$_7$ |

TABLE 4-continued

| X | Y | $Z_n$ | A | B | $E^\oplus$ |
|---|---|---|---|---|---|
| Cl | Cl | H | $-CH_2-$ | cyclopentenyl | $-NH_3\text{-i-}C_3H_7$ |
| Cl | Cl | H | $-CH_2-$ | cyclopentyl | $-NH_3\text{-i-}C_3H_7$ |
| Cl | Cl | H | $-CH_2-$ | 2,5-dihydrofuranyl | $-NH_3\text{-i-}C_3H_7$ |
| Cl | Cl | H | $-CH_2-$ | tetrahydrofuranyl | $-NH_3\text{-i-}C_3H_7$ |
| $CH_3$ | $CH_3$ | H | $-(CH_2)_4-CH(OCH_3)-$ | | Na |
| $CH_3$ | $CH_3$ | H | $-(CH_2)_3-CH(OCH_3)-CH_2-$ | | Na |
| $CH_3$ | $CH_3$ | H | $-(CH_2)_2-CH(OCH_3)-(CH_2)_2-$ | | Na |
| $CH_3$ | $CH_3$ | H | $-(CH_2)_2-CH(OC_2H_5)-(CH_2)_2-$ | | Na |
| $CH_3$ | $CH_3$ | H | $-(CH_2)_2-CH(OC_3H_7)-(CH_2)_2-$ | | Na |
| $CH_3$ | $CH_3$ | H | $-(CH_2)_2-CH(\text{O-i-}C_3H_7)-(CH_2)_2-$ | | Na |
| $CH_3$ | $CH_3$ | H | $-(CH_2)_2-CH(\text{O-t-}C_4H_9)-(CH_2)_2-$ | | Na |
| $CH_3$ | $CH_3$ | H | $-(CH_2)_3-CH(SCH_3)-CH_2-$ | | Na |
| $CH_3$ | $CH_3$ | H | $-(CH_2)_2-CH(SCH_3)-(CH_2)_2-$ | | Na |
| $CH_3$ | $CH_3$ | H | $-CH_2-$ cyclohexyl | | Na |
| $CH_3$ | $CH_3$ | H | $-CH_2-$ cyclohexyl $-CH_2-$ | | Na |
| $CH_3$ | $CH_3$ | H | $-(CH_2)_2-$ cyclohexyl $-CH_2-$ | | Na |
| $CH_3$ | $CH_3$ | H | $-(CH_2)_2-$ cyclopentyl $-CH_2-$ | | Na |
| $CH_3$ | $CH_3$ | H | $-CH_2-$ cyclopentenyl | | Na |

TABLE 4-continued

| X | Y | $Z_n$ | A | B | $E^{\oplus}$ |
|---|---|---|---|---|---|
| CH₃ | CH₃ | H | —CH₂ | | Na |
| CH₃ | CH₃ | H | —CH₂ | | Na |
| CH₃ | CH₃ | H | —CH₂ | | Na |
| CH₃ | CH₃ | H | —(CH₂)₄—CH(OCH₃)— | | —NH₃-i-C₃H₇ |
| CH₃ | CH₃ | H | —(CH₂)₃—CH(OCH₃)—CH₂— | | —NH₃-i-C₃H₇ |
| CH₃ | CH₃ | H | —(CH₂)₂—CH(OCH₃)—(CH₂)₂— | | —NH₃-i-C₃H₇ |
| CH₃ | CH₃ | H | —(CH₂)₂—CH(OC₂H₅)—(CH₂)₂— | | —NH₃-i-C₃H₇ |
| CH₃ | CH₃ | H | —(CH₂)₂—CH(OC₃H₇)—(CH₂)₂— | | —NH₃-i-C₃H₇ |
| CH₃ | CH₃ | H | —(CH₂)₂—CH(O-i-C₃H₇)—(CH₂)₂— | | —NH₃-i-C₃H₇ |
| CH₃ | CH₃ | H | —(CH₂)₂—CH(O-t-C₄H₉)—(CH₂)₂— | | —NH₃-i-C₃H₇ |
| CH₃ | CH₃ | H | —(CH₂)₃—CH(SCH₃)—CH₂— | | —NH₃-i-C₃H₇ |
| CH₃ | CH₃ | H | —(CH₂)₂—CH(SCH₃)—(CH₂)₂— | | —NH₃-i-C₃H₇ |
| CH₃ | CH₃ | H | 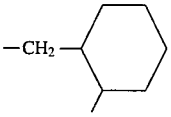 | | —NH₃-i-C₃H₇ |
| CH₃ | CH₃ | H | 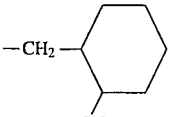 | | —NH₃-i-C₃H₇ |
| CH₃ | CH₃ | H | 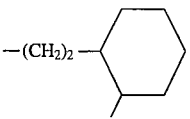 | | —NH₃-i-C₃H₇ |
| CH₃ | CH₃ | H | 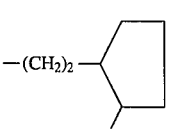 | | —NH₃-i-C₃H₇ |
| CH₃ | CH₃ | H | —CH₂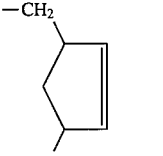 | | —NH₃-i-C₃H₇ |
| CH₃ | CH₃ | H | —CH₂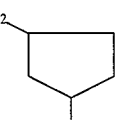 | | —NH₃-i-C₃H₇ |
| CH₃ | CH₃ | H | —CH₂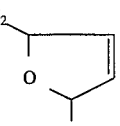 | | —NH₃-i-C₃H₇ |

TABLE 4-continued

| X | Y | $Z_n$ | A | B | $E^{\oplus}$ |
|---|---|---|---|---|---|
| $CH_3$ | $CH_3$ | H | $-CH_2-$ | (2-methyltetrahydrofuran-5-yl) | $-NH_3\text{-}i\text{-}C_3H_7$ |
| $CH_3$ | $CH_3$ | 6-$CH_3$ | | $-(CH_2)_4-CH(OCH_3)-$ | Na |
| $CH_3$ | $CH_3$ | 6-$CH_3$ | | $-(CH_2)_3-CH(OCH_3)-CH_2-$ | Na |
| $CH_3$ | $CH_3$ | 6-$CH_3$ | | $-(CH_2)_2-CH(OCH_3)-(CH_2)_2-$ | Na |
| $CH_3$ | $CH_3$ | 6-$CH_3$ | | $-(CH_2)_2-CH(OC_2H_5)-(CH_2)_2-$ | Na |
| $CH_3$ | $CH_3$ | 6-$CH_3$ | | $-(CH_2)_2-CH(OC_3H_7)-(CH_2)_2-$ | Na |
| $CH_3$ | $CH_3$ | 6-$CH_3$ | | $-(CH_2)_2-CH(O\text{-}i\text{-}C_3H_7)-(CH_2)_2-$ | Na |
| $CH_3$ | $CH_3$ | 6-$CH_3$ | | $-(CH_2)_2-CH(O\text{-}t\text{-}C_4H_9)-(CH_2)_2-$ | Na |
| $CH_3$ | $CH_3$ | 6-$CH_3$ | | $-(CH_2)_3-CH(SCH_3)-CH_2-$ | Na |
| $CH_3$ | $CH_3$ | 6-$CH_3$ | | $-(CH_2)_2-CH(SCH_3)-(CH_2)_2-$ | Na |
| $CH_3$ | $CH_3$ | 6-$CH_3$ | $-CH_2-$(2-methylcyclohexyl) | | Na |
| $CH_3$ | $CH_3$ | 6-$CH_3$ | $-CH_2-$(cyclohexane-1,2-diyl)$-CH_2-$ | | Na |
| $CH_3$ | $CH_3$ | 6-$CH_3$ | $-(CH_2)_2-$(cyclohexane-1,2-diyl)$-CH_2-$ | | Na |
| $CH_3$ | $CH_3$ | 6-$CH_3$ | $-(CH_2)_2-$(cyclopentane-1,2-diyl)$-CH_2-$ | | Na |
| $CH_3$ | $CH_3$ | 6-$CH_3$ | $-CH_2-$(cyclopent-2-en-1,4-diyl) | | Na |
| $CH_3$ | $CH_3$ | 6-$CH_3$ | $-CH_2-$(cyclopentan-1,3-diyl) | | Na |
| $CH_3$ | $CH_3$ | 6-$CH_3$ | $-CH_2-$(2,5-dihydrofuran-2,5-diyl) | | Na |
| $CH_3$ | $CH_3$ | 6-$CH_3$ | $-CH_2-$(tetrahydrofuran-2,5-diyl) | | Na |
| $CH_3$ | $CH_3$ | 6-$CH_3$ | | $-(CH_2)_4-CH(OCH_3)-$ | $-NH_3\text{-}i\text{-}C_3H_7$ |
| $CH_3$ | $CH_3$ | 6-$CH_3$ | | $-(CH_2)_3-CH(OCH_3)-CH_2-$ | $-NH_3\text{-}i\text{-}C_3H_7$ |
| $CH_3$ | $CH_3$ | 6-$CH_3$ | | $-(CH_2)_2-CH(OCH_3)-(CH_2)_2-$ | $-NH_3\text{-}i\text{-}C_3H_7$ |
| $CH_3$ | $CH_3$ | 6-$CH_3$ | | $-(CH_2)_2-CH(OC_2H_5)-(CH_2)_2-$ | $-NH_3\text{-}i\text{-}C_3H_7$ |
| $CH_3$ | $CH_3$ | 6-$CH_3$ | | $-(CH_2)_2-CH(OC_3H_7)-(CH_2)_2-$ | $-NH_3\text{-}i\text{-}C_3H_7$ |

TABLE 4-continued

| X | Y | $Z_n$ | A | B | $E^\oplus$ |
|---|---|---|---|---|---|
| $CH_3$ | $CH_3$ | 6-$CH_3$ | | $-(CH_2)_2-CH(O\text{-}i\text{-}C_3H_7)-(CH_2)_2-$ | $-NH_3\text{-}i\text{-}C_3H_7$ |
| $CH_3$ | $CH_3$ | 6-$CH_3$ | | $-(CH_2)_2-CH(O\text{-}t\text{-}C_4H_9)-(CH_2)_2-$ | $-NH_3\text{-}i\text{-}C_3H_7$ |
| $CH_3$ | $CH_3$ | 6-$CH_3$ | | $-(CH_2)_3-CH(SCH_3)-CH_2-$ | $-NH_3\text{-}i\text{-}C_3H_7$ |
| $CH_3$ | $CH_3$ | 6-$CH_3$ | | $-(CH_2)_2-CH(SCH_3)-(CH_2)_2-$ | $-NH_3\text{-}i\text{-}C_3H_7$ |
| $CH_3$ | $CH_3$ | 6-$CH_3$ | | $-CH_2-\text{cyclohexyl}$ | $-NH_3\text{-}i\text{-}C_3H_7$ |
| $CH_3$ | $CH_3$ | 6-$CH_3$ | | $-CH_2-\text{cyclohexyl}-CH_2-$ | $-NH_3\text{-}i\text{-}C_3H_7$ |
| $CH_3$ | $CH_3$ | 6-$CH_3$ | | $-(CH_2)_2-\text{cyclohexyl}-CH_2-$ | $-NH_3\text{-}i\text{-}C_3H_7$ |
| $CH_3$ | $CH_3$ | 6-$CH_3$ | | $-(CH_2)_2-\text{cyclopentyl}-CH_2-$ | $-NH_3\text{-}i\text{-}C_3H_7$ |
| $CH_3$ | $CH_3$ | 6-$CH_3$ | $-CH_2$ | cyclopentenyl | $-NH_3\text{-}i\text{-}C_3H_7$ |
| $CH_3$ | $CH_3$ | 6-$CH_3$ | $-CH_2$ | cyclopentyl | $-NH_3\text{-}i\text{-}C_3H_7$ |
| $CH_3$ | $CH_3$ | 6-$CH_3$ | $-CH_2$ | 2,5-dihydrofuranyl | $-NH_3\text{-}i\text{-}C_3H_7$ |
| $CH_3$ | $CH_3$ | 6-$CH_3$ | $-CH_2$ | tetrahydrofuranyl | $-NH_3\text{-}i\text{-}C_3H_7$ |

If, in accordance with process (A), ethyl 1-(2,6-dichlorophenylacetyloxy)-4-isopropoxy-cyclohexanecarboxylate is used, the course of the process according to the invention can be represented by the following equation:

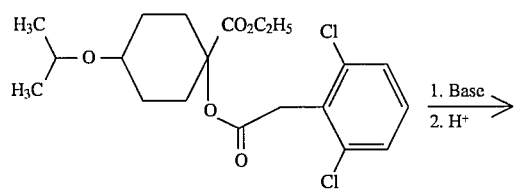

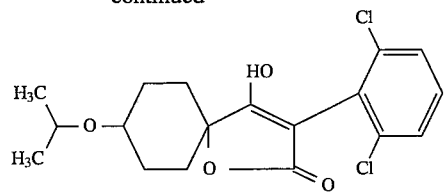

-continued

If, in accordance with process (B) (variant α), 3-(2,4,6-trimethylphenyl)-4-hydroxy-5,5-(2-ethoxy)pentamethylene-$\Delta^3$-dihydrofuran-2-one and pivaloyl chloride are used as starting substances, the course of the reaction according to the invention can be represented by the following equation:

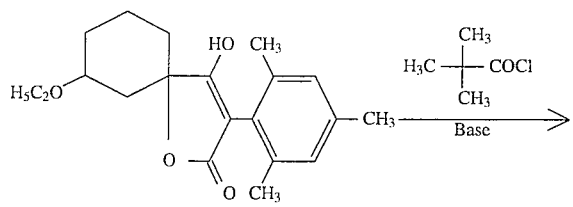

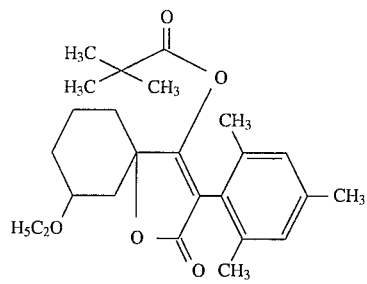

If, in accordance with process B (variant β), 3-(2,4,6-trimethylphenyl)-4-hydroxy-5,5-(2-methoxy)tetramethylene-Δ³-dihydrofuran-2-one and acetic anhydride are used as starting compounds, the course of the process according to the invention can be represented by the following equation:

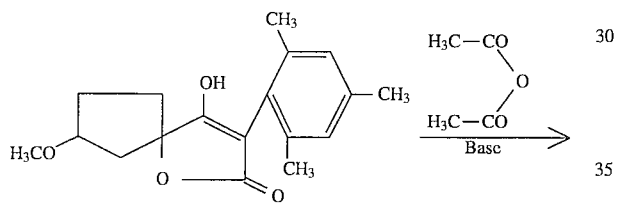

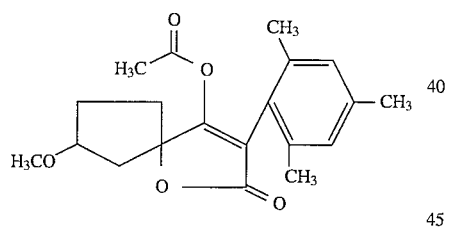

If, in accordance with process C, 3-(2,4-dichlorophenyl)-4-hydroxy-5,5-(3-propoxy)pentamethylene-Δ³-dihydrofuran-2-one and ethoxyethyl chloroformate are used as starting compounds, the course of the process according to the invention can be represented by the following equation:

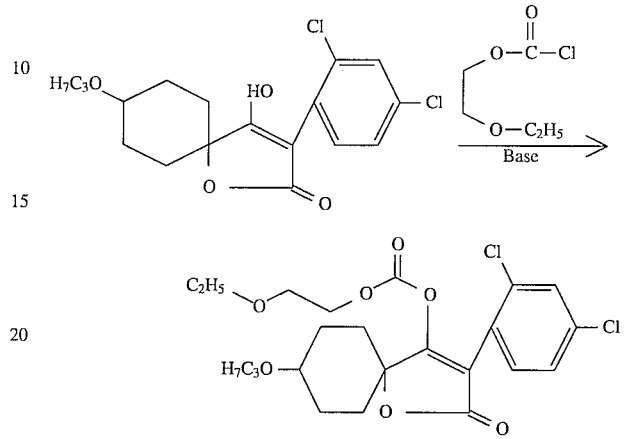

If, in accordance with process ($D_\alpha$), 3-(2,4,6-trimethylphenyl)-3-hydroxy-5,5-(3-tert-butoxy)pentamethylene-Δ³-dihydrofuran-2-one and methyl chloromonothioformate are used as starting materials, the course of the reaction can be represented as follows:

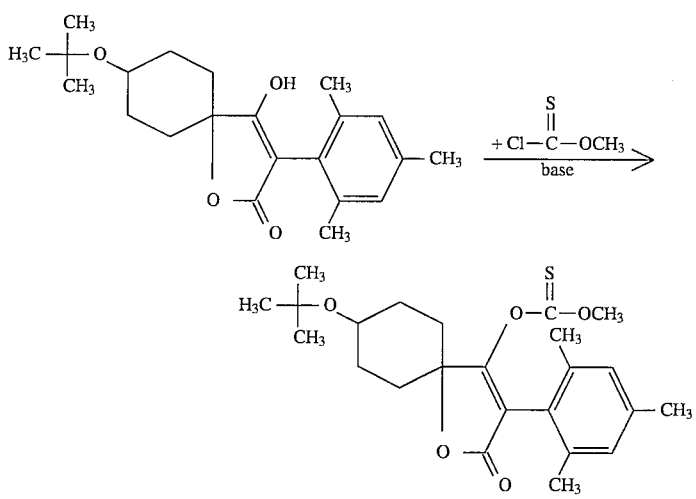

If, in accordance with process (E), 3-(2,4,6-trimethylphenyl-4-hydroxy-5,5-(1,2-tetramethylene)trimethylene-Δ³-dihydrofuran-2-one and methanesulphonyl chloride are used as starting materials, the course of the reaction can be represented by the following equation:

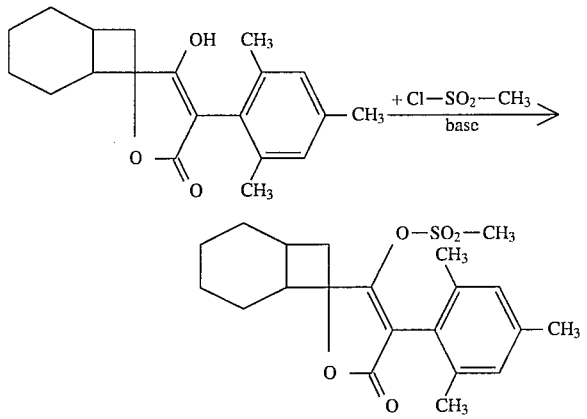

If, in accordance with process (F), 3-(2,4,6-trimethylphenyl-4-hydroxy-5,5-(1,4-oxy)pentamethylene-Δ³-dihydrofuran-2-one and 2,2,2-trifluoroethyl methanechlorothiophosphonate are used as starting materials, the course of the reaction can be represented by the following equation:

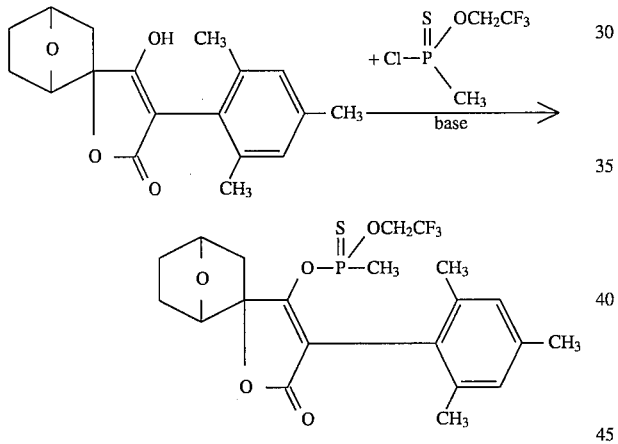

If, in accordance with process (G$_\alpha$) 3-(2,4,6-trimethylphenyl)-4-hydroxy-5,5-(2,3-tetramethylene)tetramethylene-Δ³-dihydrofuran-2-one and ethyl isocyanate are used as starting materials, the course of the reaction can be represented by the following equation:

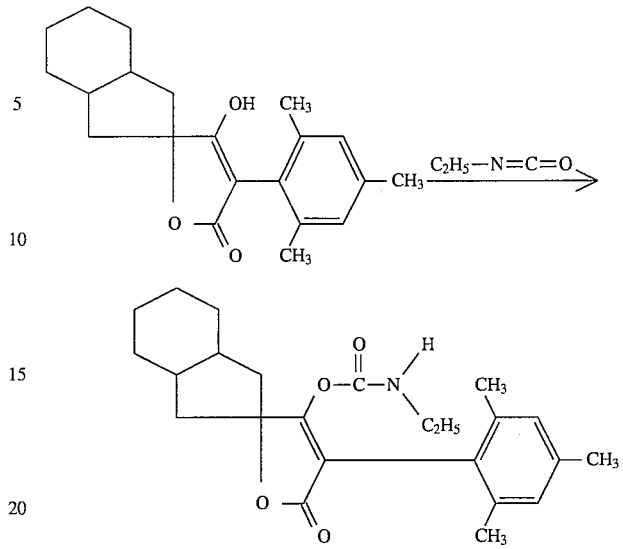

If, in accordance with process (G$_\beta$) 3-(2,4,6-trimethylphenyl)-4-hydroxy-5,5-(2-methylmercapto)pentamethylene-Δ³-dihydrofuran-2-one and dimethylcarbamoyl chloride are used as starting materials, the course of the reaction can be represented by the following equation:

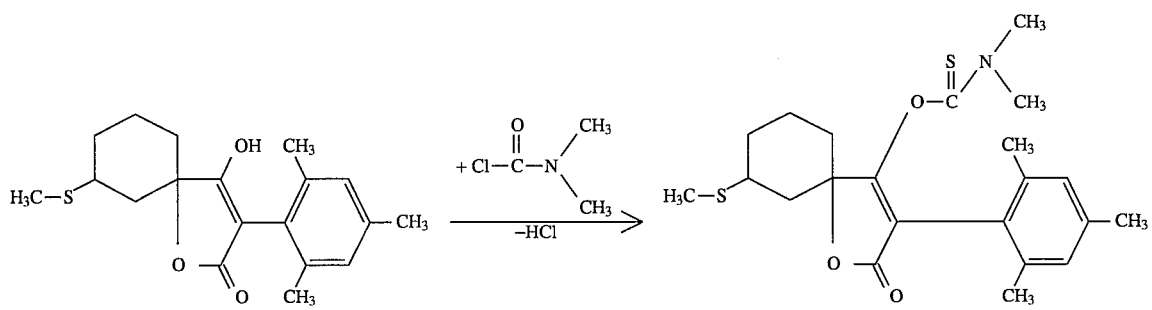

If, in accordance with process (H), 3-(2,4,6-trimethylphenyl)-4-hydroxy-5,5-(2-methoxy)pentamethylene-Δ³-dihydrofuran-2-one and NaOH are used as reactants, the course of the process according to the invention can be represented by the following equation:

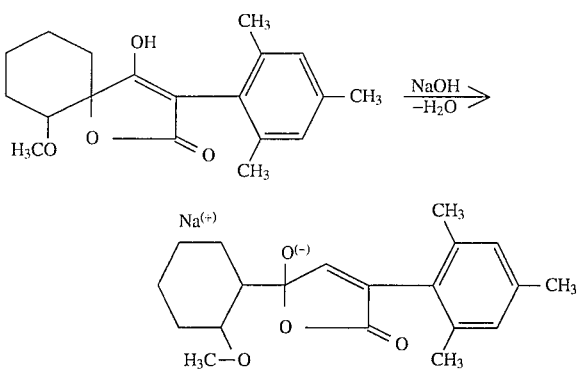

The compounds of the formula (II)

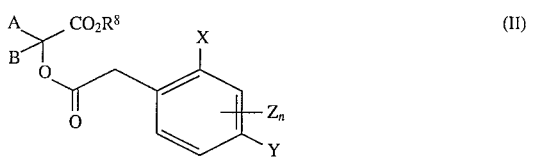

in which

A, B, X, Y, Z, n and $R^8$ have the abovementioned meaning and which are required as starting substances in the above process (A) are new, but can be prepared in a simple manner by processes known in principle. For example, O-acyl-α-hydroxy carboxylic esters of the formula (II) are obtained when a) 2-hydroxy carboxylic acid (esters) of the formula (XIII)

in which $R^{12}$ represents hydrogen (XIIIa) or alkyl (XIIIb) and

A and B have the abovementioned meaning, are acylated with phenylacetyl halides of the formula (XIV)

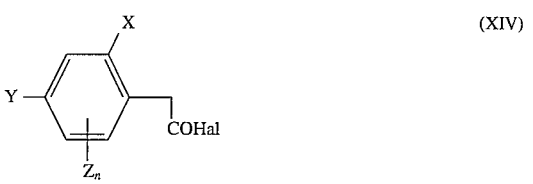

in which

X, Y, Z and n have the abovementioned meaning and Hal represents chlorine or bromine
(Chem. Reviews 52 237–416 (1953));
and optionally esterified,
or when hydroxy carboxylic acids of the formula (IIa)

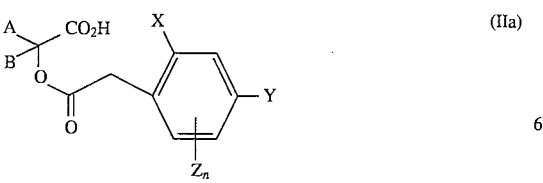

in which

A, B, X, Y, Z and n have the abovementioned meaning are esterified (Chem. Ind. (London) 1568 (1968).

Compounds of the formula (IIa) can be obtained, for example, from the phenylacetyl halides of the formula (XIII) and hydroxy carboxylic acids of the formula (XIIIa) (Chem. Reviews 52 237–416 (1953)).

The following compounds of the formula (II) may be mentioned by way of example:

Ethyl 1-(2,4-dichlorophenyl-acetyloxy)-2-methoxy-cyclohexanecarboxylate
Ethyl 1-(2,6-dichlorophenyl-acetyloxy)-2-methoxy-cyclohexanecarboxylate
Ethyl 1-(2-chloro-6-fluorophenyl-acetyloxy)-2-methoxycyclohexanecarboxylate
Ethyl 1-(2,4-dimethylphenyl-acetyloxy)-2-methoxy-cyclohexanecarboxylate
Ethyl 1-(2,6-dimethylphenyl-acetyloxy)-2-methoxy-cyclohexanecarboxylate
Ethyl 1-(2,4,6-trimethylphenyl-acetoxy)-2-methoxycyclohexanecarboxylate
Ethyl 1-(2,6-dichloro-4-trifluoromethylphenyl-acetoxy)-2-methoxy-cyclohexanecarboxylate
Ethyl 1-(2,4-dichlorophenyl-acetyloxy)-3-methoxy-cyclohexanecarboxylate
Ethyl 1-(2,6-dichlorophenyl-acetyloxy)-3-methoxy-cyclohexanecarboxylate
Ethyl 1-(2-chloro-6-fluorophenyl-acetyloxy)-3-methoxycyclohexanecarboxylate
Ethyl 1-(2,4-dimethylphenyl-acetyloxy)-3-methoxy-cyclohexanecarboxylate
Ethyl 1-(2,6-dimethylphenyl-acetyloxy)-3-methoxy-cyclohexanecarboxylate
Ethyl 1-(2,4,6-trimethylphenyl-acetoxy)-3-methoxycyclohexanecarboxylate
Ethyl 1-(2,6-dichloro-4-trifluoromethylphenyl-acetoxy)3-methoxy-cyclohexanecarboxylate
Ethyl 1-(2,4-dichlorophenyl-acetyloxy)-4-methoxy-cyclohexanecarboxylate
Ethyl 1-(2,6-dichlorophenyl-acetyloxy)-4-methoxy-cyclohexanecarboxylate
Ethyl 1-(2-chloro-6-fluorophenyl-acetyloxy)-4-methoxycyclohexanecarboxylate
Ethyl 1-(2,4-dimethylphenyl-acetyloxy)-4-methoxy-cyclohexanecarboxylate
Ethyl 1-(2,6-dimethylphenyl-acetyloxy)-4-methoxy-cyclohexanecarboxylate
Ethyl 1-(2,4,6-trimethylphenyl-acetoxy)-4-methoxycyclohexanecarboxylate
Ethyl 1-(2,6-dichloro-4-trifluoromethylphenyl-acetoxy)-4-methoxy-cyclohexanecarboxylate
Ethyl 1-(2,4-dichlorophenyl-acetyloxy)-4-ethoxy-cyclohexanecarboxylate
Ethyl 1-(2,6-dichlorophenyl-acetyloxy)-4-ethoxy-cyclohexanecarboxylate
Ethyl 1-(2-chloro-6-fluorophenyl-acetyloxy)-4-ethoxycyclohexanecarboxylate
Ethyl 1-(2,4-dimethylphenyl-acetyloxy)-4-ethoxy-cyclohexanecarboxylate
Ethyl 1-(2,6-dimethylphenyl-acetyloxy)-4-ethoxy-cyclohexanecarboxylate
Ethyl 1-(2,4,6-trimethylphenyl-acetoxy)-4-ethoxy-cyclohexanecarboxylate
Ethyl 1-(2,6-dichloro-4-trifluoromethylphenyl-acetoxy)-4-ethoxy-cyclohexanecarboxylate
Ethyl 1-(2,4-dichlorophenyl-acetyloxy)-4-isopropoxycyclohexanecarboxylate
Ethyl 1-(2,6-dichlorophenyl-acetyloxy)-4-isopropoxycyclohexanecarboxylate
Ethyl 1-(2-chloro-6-fluorophenyl-acetyloxy)-4-isopropoxycyclohexanecarboxylate
Ethyl 1-(2,4-dimethylphenyl-acetyloxy)-4-isopropoxycyclohexanecarboxylate Ethyl 1-(2,6-dimethylphenyl-acetyloxy)-4-isopropoxycyclohexanecarboxylate
Ethyl 1-(2,4,6-trimethylphenyl-acetoxy)-4-isopropoxycyclohexanecarboxylate
Ethyl 1-(2,6-dichloro-4-trifluoromethylphenyl-acetoxy)-4-isopropoxy-cyclohexanecarboxylate
Ethyl 1-(2,4-dichlorophenyl-acetyloxy)-4-t-butoxycyclohexanecarboxylate
Ethyl 1-(2,6-dichlorophenyl-acetyloxy)-4-t-butoxycyclohexanecarboxylate
Ethyl 1-(2-chloro-6-fluorophenyl-acetyloxy)-4-t-butoxycyclohexanecarboxylate
Ethyl 1-(2,4-dimethylphenyl-acetyloxy)-4-t-butoxycyclohexanecarboxylate
Ethyl 1-(2,6-dimethylphenyl-acetyloxy)-4-t-butoxycyclohexane carboxylate
Ethyl 1-(2,4,6-trimethylphenyl-acetoxy)-4-t-butoxycyclohexanecarboxylate
Ethyl 1-(2,6-dichloro-4-trifluoromethylphenyl-acetoxy)-4-t-butoxy-cyclohexanecarboxylate
Ethyl 1-(2,4-dichlorophenyl-acetyloxy)-3,4-trimethylene-cyclohexanecarboxylate
Ethyl 1-(2,6-dichlorophenyl-acetyloxy)-3,4-trimethylene-cyclohexanecarboxylate
Ethyl 1-(2-chloro-6-fluorophenyl-acetyloxy)-3,4-trimethylene-cyclohexanecarboxylate
Ethyl 1-(2,4-dimethylphenyl-acetyloxy)-3,4-trimethylene-cyclohexanecarboxylate
Ethyl 1-(2,6-dimethylphenyl-acetyloxy)-3,4-trimethylene-cyclohexanecarboxylate
Ethyl 1-(2,4,6-trimethylphenyl-acetoxy)-3,4-trimethylene-cyclohexane carboxylate
Ethyl 1-(2,6-dichloro-4-trifluoromethylphenyl-acetoxy)-3,4-trimethylene-cyclohexanecarboxylate
Ethyl 1-(2,4-dichlorophenyl-acetyloxy)-2,5-methylenecyclohexanecarboxylate
Ethyl 1-(2,6-dichlorophenyl-acetyloxy)-2,5-methylenecyclohexanecarboxylate
Ethyl 1-(2-chloro-6-fluorophenyl-acetyloxy)-2,5-methylene-cyclohexanecarboxylate
Ethyl 1-(2,4-dimethylphenyl-acetyloxy)-2,5-methylenecyclohexanecarboxylate
Ethyl 1-(2,6-dimethylphenyl-acetyloxy)-2,5-methylenecyclohexanecarboxylate
Ethyl 1-(2,4,6-trimethylphenyl-acetoxy)-2,5-methylenecyclohexanecarboxylate
Ethyl 1-(2,6-dichloro-4-trifluoromethylphenyl-acetoxy)-2,5-methylene-cyclohexanecarboxylate Process (A) is characterized in that compounds of the formula (II) in which A, B, X, Y, Z, n and $R^8$ have the abovementioned meaning are subjected to an intramolecular condensation reaction in the presence of bases.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. Alcohols, such as methanol, ethanol, propanol, iso-propanol, butanol, iso-butanol or tert-butanol, can furthermore be employed.

Bases (deprotonating agents) which can be employed when carrying out the process (A) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, all of which can be used in the presence of phase transfer catalysts, such as, for example, triethylbenzylammonium chloride, tetrabutylammonium bromide, Adogen 464 or TDA 1.* Alkali metals, such as sodium or potassium, can furthermore be used. Other substances which can be employed are alkali metal amides, alkali metal hydrides, alkaline earth metal amides and alkaline earth metal hydrides, such as sodium amide, sodium hydride and calcium hydride, and furthermore also alkali metal alcoholates, such as sodium methylate, sodium ethylate and potassium tert-butylate.

*Adogen 464=methyltrialkyl ($C_8$-$C_{10}$)ammonium chloride
TDA 1=tris-(methoxyethoxyethyl)amine When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formula (II) and the deprotonating bases are generally employed in approximately equimolar amounts. However, it is also possible to use one or the other components in a larger excess (up to 3 mol).

Process (Bα) is characterized in that compounds of the formula (Ia) are reacted with carbonyl halides of the formula (III).

If the acid halides are used, then diluents which can be employed in the process (Bα) according to the invention are all solvents which are inert to these compounds. The following can preferably be used: hydrocarbons, such as benzine, benzene, toluene, xylene and tetralin, furthermore, halogenohydrocarbons, such as methylene chloride, chloroform, carbon tetrachloride, chlorobenzene and o-dichlorobenzene, furthermore ketones, such as acetone and methyl isopropyl ketone, moreover ethers, such as diethyl ether, tetrahydrofuran and dioxane, in addition carboxylates, such as ethyl acetate, and also strongly polar solvents, such as dimethyl sulphoxide and sulpholane. If the acid halide is sufficiently stable to hydrolysis, the reaction can also be carried out in the presence of water.

If the corresponding carbonyl halides are used, then suitable acid-binding agents in the reaction in accordance with process (Bα) according to the invention are all customary acid acceptors. The following can preferably be used: tertiary amines, such as triethylamine, pyridine, diazabicyclooctane (DABCO), diazabicycloundecane (DBU), diazabicyclononene (DBN), Hünig base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate.

When carrying out the process (Bα) according to the invention and carbonyl halides are used, the reaction temperatures can also be varied within a substantial range. In general, the process is carried out at temperatures between −20° C. and +150° C., preferably between 0° C. and 100° C.

When carrying out the process (Bα) according to the invention, the starting substances of the formula (Ia) and the carbonyl halide of the formula (III) are generally used in approximately equivalent amounts. However, it is also possible to employ the carbonyl halide in a larger excess (up to 5 mol). Working-up is carried out by customary methods.

Process (Bβ) is characterized in that compounds of the formula (Ia) are reacted with carboxylic anhydrides of the formula (IV).

If, in process (Bβ) according to the invention, carboxylic anhydrides are used as reactants of the formula (IV), then suitable diluents which can be used are preferably those which are also preferably suitable when acid halides are used. An excess of the carboxylic anhydride employed can, furthermore, also act simultaneously as diluent.

When carrying out the process (Bβ) according to the invention and carboxylic anhydrides are used, the reaction temperatures can be varied within a substantial range. In general, the process is carried out at temperatures between −20° C. and +150° C., preferably between 0° C. and 100° C.

When carrying out the process (Bβ) according to the invention, the starting substances of the formula (Ia) and the carboxylic anhydride of the formula (IV) are generally used in approximately equivalent amounts. However, it is also possible to employ the carboxylic anhydride in a larger excess (up to 5 mol). Working-up is carried out by customary methods.

In general, a procedure is followed in which diluent and an excess of carboxylic anhydride and also the carboxylic acid which forms are removed by distillation or by washing with an organic solvent or with water.

Process (C) is characterized in that compounds of the formula (Ia) are reacted with chloroformic esters or chloroformic thioesters of the formula (V).

If the corresponding chloroformic esters or chloroformic thioesters are used, then suitable acid acceptors in the reaction in accordance with process (C) according to the invention are all customary acid acceptors. The following can preferably be used: tertiary amines, such as triethylamine, pyridine, DABCO, DBC, DBA, Hünig base and N,N-dimethyl-aniline, furthermore alkaline earth metal oxides, such as magnesium oxide and calcium oxide, and moreover alkali metal carbonates and alkaline earth metal carbonates, such as sodium carbonate, potassium carbonate and calcium carbonate.

Diluents which can be employed in process (C) according to the invention when the chloroformic esters or chloroformic thioesters are used are all solvents which are inert towards these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, in addition ethers, such as diethyl ether, tetrahydrofuran and dioxane, additionally carboxylates, such as ethyl acetate, and also strongly polar solvents, such as dimethyl sulphoxide and sulpholane.

When using the chloroformic esters or chloroformic thioesters as carboxylic acid derivatives of the formula (V), the reaction temperatures, when carrying out process (C) according to the invention, can be varied within a substantial range. If the process is carried out in the presence of a diluent and of an acid-binding agent, the reaction temperatures are generally between −20° C. and +100° C., preferably between 0° C. and 50° C.

Process (C) according to the invention is generally carried out under atmospheric pressure.

For carrying out the process (C) according to the invention, the starting substances of the formula (Ia) and the particular chloroformic ester or chloroformic thioester of the formula (V) are generally used in approximately equivalent amounts. However, it is also possible to employ one or the other components in a larger excess (up to 2 mol). Working-up is then carried out by customary methods. In general, a procedure is followed in which precipitated salts are removed and the reaction mixture which remains is concentrated by stripping off the diluent.

In preparation process D, approximately 1 mol of chloromonothioformic ester or chlorodithioformic ester of the formula (VI) is employed per mol of starting compound of the formula (Ia) at 0° to 120° C., preferably at 20° to 60° C.

Suitable diluents which may be added are all inert polar organic solvents, such as ethers, amides, alcohols, sulphones or sulphoxides.

Dimethyl sulphoxide, tetrahydrofuran, dimethylformamide and dimethyl sulphide are preferably employed.

If, in a preferred embodiment, the enolate salt of the compound Ia is prepared by adding strong deprotonating agents, such as, for example, sodium hydride or potassium tertiary burylate, a further addition of acid-binding agents can be dispensed with.

If acid-binding agents are employed, then suitable substances are customary inorganic or organic bases; sodium hydroxide, sodium carbonate, potassium carbonate, pyridine and triethylamine may be mentioned by way of example.

The reaction can be carried out under atmospheric pressure or under elevated pressure, it is preferably carried out under atmospheric pressure. Working-up is carried out by customary methods.

In preparation process (E), approximately 1 mol of sulphonyl chloride (VII) is reacted per mol of starting compound of the formula (Ia) at 0° to 150° C., preferably at 20° to 70° C.

Suitable diluents which may be added are all inert polar organic solvents, such as ethers, amides, nitriles, alcohols, sulphones and sulphoxides.

Dimethyl sulphoxide, tetrahydrofuran, dimethylformamide and dimethyl sulphide are preferably employed.

If, in a preferred embodiment, the enolate salt of the compound Ia is synthesized by adding strong deprotonating agents, (such as, for example, sodium hydride or potassium tertiary butylate), a further addition of acid-binding agents can be dispensed with.

If acid-binding agents are employed, then suitable substances are customary inorganic or organic bases; sodium hydroxide, sodium carbonate, potassium carbonate and pyridine may be mentioned by way of example.

The reaction can be carried out under atmospheric pressure or under elevated pressure, it is preferably carried out under atmospheric pressure. Working-up is carried out by customary methods.

To obtain compounds of the structure (Ie), in preparation process (F), 1 to 2, preferably 1 to 1.3, mol of the phosphorus compound of the formula (VIII) are employed per mol of the compound (Ia) at temperatures between −40° C. and 150° C., preferably between −10° and 110° C.

Suitable diluents which may be added are all inert, polar organic solvents, such as ethers, amides, nitriles, alcohols, sulphides, sulphones, sulphoxides and the like.

Acetonitrile, dimethyl sulphoxide, tetrahydrofuran, dimethylformamide and dimethyl sulphide are preferably employed.

Suitable acid-binding agents which may be added are customary inorganic or organic bases, such as hydroxides or carbonates. Examples which may be mentioned are sodium hydroxide, sodium carbonate, potassium carbonate and pyridine.

The reaction can be carried out under atmospheric pressure or under elevated pressure, it is preferably carried out under atmospheric pressure. Working-up is carried out by customary methods of organic chemistry. The end products obtained are preferably purified by crystallization, chromatography or by so-called "incipient distillation", i.e. removal of the volatile components in vacuo.

In preparation process $G_\alpha$, approximately 1 mol of isocyanate of the formula (IX) is reacted per mol of starting compound of the formula Ia at 0° to 100° C., preferably at 20° to 50° C.

Suitable diluents which may be added are all inert organic solvents, such as ethers, amides, nitriles, sulphones and sulphoxides.

If appropriate, catalysts can be added to accelerate the reaction. Catalysts which can be employed very advantageously are organotin compounds, such as, for example, dibutyltin dilaurate. The process is preferably carried out under atmospheric pressure.

In preparation process $G_\beta$, approximately 1 mol of carbamoyl chloride or thiocarbamoyl chloride of the formula (X) is reacted per mol of starting compound of the formula (Ia) at 0° to 150° C., preferably at 20° to 70° C.

Suitable diluents which may be added are all inert polar organic solvents, such as ethers, amides, alcohols, sulphones and sulphoxides, sulphides.

Dimethyl sulphoxide, tetrahydrofuran, dimethylformamide and dimethyl sulphide are preferably employed.

If, in a preferred embodiment, the enolate salt of the compound Ia is prepared by adding strong deprotonating agents (such as, for example, sodium hydride or potassium tertiary burylate), a further addition of acid-binding agents can be dispensed with.

If acid-binding agents are employed, then suitable substances are customary inorganic or organic bases; sodium hydroxide, sodium carbonate, potassium carbonate and pyridine may be mentioned by way of example.

The reaction can be carried out under atmospheric pressure or under elevated pressure, it is preferably carried out under atmospheric pressure. Working-up is carried out by customary methods.

Process (H) is characterized in that compounds of the formula (Ia) are reacted with metal hydroxides (XI) or amines (XII).

Diluents which can be employed in the process according to the invention are preferably ethers, such as tetrahydrofuran, dioxane, diethyl ether, or else alcohols, such as methanol, ethanol or isopropanol, but also water. Process (H) according to the invention is generally carried out under atmospheric pressure. The reaction temperatures are generally between −20° C. and 100° C., preferably between 0° C. and 50° C.

When carrying out the process (H) according to the invention, the starting substances of the formula (Ia) and (XII) or (XIII) are generally used in approximately equimolar amounts. However, it is also possible to employ one or the other component in a larger excess (up to 2 mol). In general, a procedure is followed in which the reaction mixture is concentrated by stripping off the diluent.

The compounds of the formula I according to the invention can be employed for combating pests. Pests are undesired animal pests, in particular insects, mites and nematodes, which are harmful to plants or higher animals. However, the pests also include undesired plants.

The active compounds according to the invention are suitable for combating animal pests, preferably arthropods, in particular insects, arachnida and nematodes, encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp..

From the order of the Anoplura, for example, *Phylloxera vastatrix,* Pemphigus spp., *Pediculus humanus corpotis,* Haematopinus spp. and Linognathus spp..

From the order of the Mallophaga, for example, Trichodecres spp. and Damalinea spp..

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp..

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp..

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., Spodoptera exigua, *Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp..

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp..

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, tylenchulus semipenetrans,* Heterodera spp., Meloidogyne spp., Aphelenchoides spp., Longidorus spp., Xiphinema spp. and Trichodorus spp..

Besides, the active compounds of the formula (I) according to the invention also have a good fungicidal activity and can be used for combating plant diseases, such as, for example, against the pathogen causing rice blast disease (*Pyricularia oryzae*).

For use as insecticides, acaricides and nematicides, the active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be between 0.0000001 and 95% by weight of active compound, preferably between 0.0001 and 1% by weight.

They are used in a customary manner suitable for the use form.

The compounds according to the invention are also specially suitable for the treatment of vegetative and generative propagation material, such as, for example, seeds of cereals, maize, vegetables and the like, or bulbs, cuttings and the like.

When used against hygiene pests and stored-product pests, the active compounds are distinguished by an outstanding residual action on wood and clay and by good stability to alkali on limed substrates.

The active compounds according to the invention can also be used as herbicides, preferably as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Arena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating monocotyledon weeds in dicotyledon cultures, by the pre- and also the post-emergence method.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxapropethyl, fluazifopbutyl, haloxyfop-methyl and quizalofopethyl; azinones such as, for example, chloridazon and norflurazon; carbamates such as, for example, chlorpropham, desmedipham, phenmedipham and propham; chloroacetanilides such as, for exmaple, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuronmethyl; thiocarbamates such as, for example, burylate, cycloate, diallate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulfosate and tridiphane.

Mixtures with other known active compounds, such as fungicides, insecticides, acaricides, nematicides, bird repellants, plant nutrients and agents which improve soil structure, are also possible.

The following insecticides may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alaycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptonophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamdon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, DMTP (O,O-dimethyl S[5-methoxy-1,3,4-thiadiazol-2(3H)-onyl-(3)-methyl] dithiophosphate), DDVP (dimethyl 2,2-dichlorovinyl phosphate), CYAP (O,O-dimethyl O-4-cyanophenyl thiophosphate), buprofezin, chlorfluazuron, diflubenzron, flucycloxuron, flufenoxuron, hexaflumuron, pyriproxifen, tebufenozide, teflubenzuron, triflumuron, imidacloprid, nitenpyram, N-[(6-chloro-3-pyridinyl)methyl]-N'-cyano-N-methylethaneimide-amide (NI-25), abamectin, amitrazin, avermectin, azadirachtin, bensultap, *Bacillus thuringiensis*, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, phoxim, prothiofos, pyrachlofos, sebufos, silafluofen, tebupirimphos, tefluthrin, terbufos, thiocarb, thiafenox, butylpyridaben, clofentezine, cyhexatin, difenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenfox, hexythiazox, ivemectin, methidathion, monocrotophos, moxidectin, naled, phosalone, profenofos, pyraclofos, pyridaben, pyrimidifen, tebufenpyrad, thuringiensin, triarathene and also 4-bromo-2-(4-chlorophenyl)-1-(ethoxymethyl)-5-(trifluoromethyl)-1H-pyrrole-3-carbonitrile (AC 303630), dicotol, chlorobenzilate, bromopropylate, chlorofenson, BPPS.

Particularly favorable mixing partners are furthermore, for example, the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulfate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl] acetate; 2-phenylphenol (OPP, aldimorph ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazime, carboxine, chinomethionate (quinomethionate), chloroneb, chloropicrin, chlorothalonil, chlozolinate, cufraneb, cymoxanil, cyproconazole, cyprofuram, dichloropren, diclobutrazole, diclofluanid, diclomezin, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenamirol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazole, imazalil, imibenconazole, iminoctadin, iprobenfos (IBP), iprodione, isoprothiolan, kasugamycin, copper formulations, such as: copper hydroxide, copper naphthenate, copper oxychloride, copper sulfate, copper dioxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel, dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidon, propamocarb, propioconazole, propineb, pyrazophos, pyrifenox, pyrimethanil, pyroquilon, quintozen (PCNB), sulfur and sulfur formulations, tebuconazole, tecloftalam, tecnazen, tetraconazole, thiabendazole, thicyofen, thiophanate-methyl, thiram, tolclophos-methyl, tolylfluanid, triadimefon, triadimenol, triazoxide, trichlamid, tricyclazole, tridemorph, triflumizole, triforin, triticonazole, validamycin A, vinclozolin, zineb, ziram.

Bactericides:

Bronopol, dichlorophen, nitrapyrin, nickel dimethyldithiocarbamate, kasugamycin, octhil inon, furancarboxylic acid, oxytetracycline, probenazole, streptomycin, tecloftalam, copper sulfate and other copper formulations.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

To prepare the pesticides, the active compounds according to the invention can be converted into the customary formulations, such as solutions, emulsions, suspensions, powders, foams, pastes, granules, aerosols, natural and synthetic materials impregnated with active compound, and very fine capsules in polymeric substances and in coating compositions for seeds, furthermore in formulations used with burning equipment, such as fumigating cartridges, fumigating cans, fumigating coils and the like, as well as ULV cold-mist and warm-mist formulations.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seeds, and furthermore in formulations used with burning equipment, such as fumigating cartridges, fumigating cans, fumigating coils and the like, as well as ULV cold-mist and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The compositions according to the invention preferably contain, besides at least one of a compound of the general formula (I) and, if appropriate, besides conventional extenders and auxiliaries, at least one surface-active substance.

The preparation of the compounds of the general formula (I) according to the invention will be illustrated by the preparation examples which follow, and the biological activity by the biological examples which follow.

The compounds listed below will be used as comparison substances in the use examples which follow:

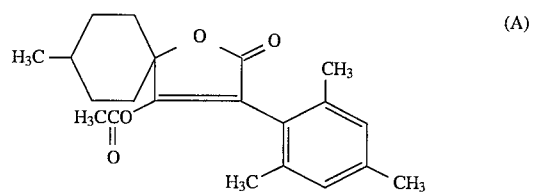
(A)

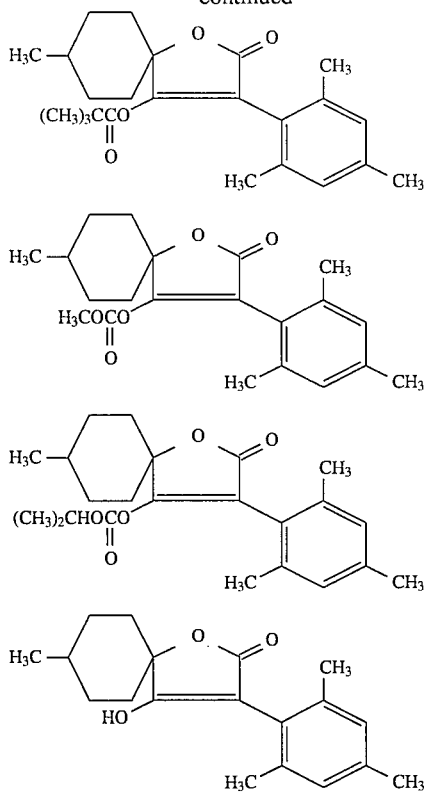

(all disclosed in EP 0,528,156)

EXAMPLE A

*Heliothis virescens* test
  Solvent: 7 parts by weight of dimethylformamide
  Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) are treated by being dipped into the preparation of active compound of the desired concentration and are infested with tobacco budwork caterpillars (*Heliothis virescens*) while the leaves are still moist.

After the specified periods of time, the destruction in % is determined. 100% means that all the caterpillars have been killed; 0% means that none of the caterpillars have been killed.

In this test, for example the compounds of Preparation Examples Ib-6, Ib-8, Ic-4 and Ic-5 resulted in a destruction of 100% after 7 days at an exemplary concentration of active compound of 0.1%, while the compounds of the prior art resulted in a destruction of not more than 40%.

EXAMPLE B

Myzus test
  Solvent: 7 parts by weight of dimethylformamide
  Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested with the green peach aphid (*Myzus persicae*) are treated by being dipped into the preparation of active compound of the desired concentration.

After the specified periods of time, the destruction in % is determined. 100% means that all the aphids have been killed; 0% means that none of the aphids have been killed.

In this test, for example the compounds of Preparation Examples Ic-4 and Ic-5 show a degree of destruction of not less than 85% after 6 days at an exemplary concentration of active compound of 0.01%.

EXAMPLE C

Critical concentration test/root-systemic action
  Test insect: *Phaedon cochleariae* larvae
  Solvent: 4 parts by weight of acetone
  Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (*Brassica oleracea*). The active compound can in this way be taken up from the soil by the roots of the plants and be transported into the leaves.

To demonstrate the root-systemic effect, the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, for example the compound of Preparation Example Ic-4 shows a degree of destruction of 100% at an exemplary concentration of active compound of 20 ppm.

EXAMPLE D

Tetranychus test (OP resistant)
  Solvent: 3 parts by weight of dimethylformamide
  Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the two-spotted spider mite (*Tetranychus urticae*) are sprayed with a preparation of active compound of the desired concentration.

After the specified periods of time, the destruction in % is estimated. 100% means that all the spider mites have been killed; 0% means that none of the spider mites have been killed.

In this test, for example the compound of Preparation Example Ic-5 showed a degree of destruction of 100% after 14 days at an exemplary concentration of active substance of 0.004%.

EXAMPLE E

Panonychus test
  Solvent: 3 parts by weight of dimethylformamide
  Emulsifier: 1 part by weight of alkylaryl polyglycol ether
  To produce a suitable preparation of active compound, 1 part by weight of active compound is mixed with the stated amount of solvent, and the concentrate is diluted with emulsifier-containing water to the desired concentration.

Plum trees (*Prunus domestica*) approximately 30 cm in height, which are heavily infested with all development stages of the red spider (*Panonychus ulmi*), are sprayed with a preparation of active compound of the desired concentration.

After the specified periods of time, the activity in % is determined. 100% means that all the spider mites have been killed; 0% means that none of the spider mites have been killed.

In this test, for example the compound of Preparation Example Ic-4 showed a degree of destruction of 100% after 14 days at an exemplary concentration of active substance of 0.004%.

EXAMPLE F

Pre-emergence test
  Solvent: 5 parts by weight of acetone
  Emulsifier: 1 part by weight of alkylaryl polyglycol ether
  To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:
  0%=no action (like untreated control)
  100%=total destruction A clearly superior activity and crop plant selectivity compared with the prior art are shown, in this test, for example by the compounds of Preparation Examples Ia-4, Ib-6, Ib-8, Ic-4 and Ic-5.

EXAMPLE G

Post-emergence test
  Solvent: 5 parts by weight of acetone
  Emulsifier: 1 part by weight of alkylaryl polyglycol ether
  To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control. The figures denote:
  0%=no action (like untreated control)
  100%=total destruction A clearly superior activity and crop plant selectivity compared with the prior art are shown, in this test, for example by the compounds of Preparation Examples Ia-4, Ib-6, Ib-8 and Ic-4.

EXAMPLE Ia-1

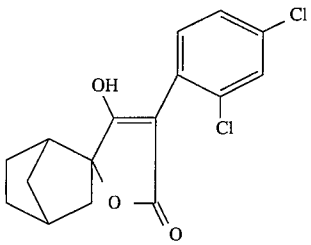

16.83 g (0.15 mol) of potassium tert-butylate are introduced into 100 ml of absolute DMF, a solution of 37.10 g (0.10 mol) of ethyl 2-O-(2,4-dichlorophenylacetyl)norbornane-2-carboxylate in 100 ml of absolute DMF is added dropwise at 0°–10° C., and the mixture is stirred for 16 hours at room temperature.

For working-up, the reaction mixture is added dropwise to 500 ml of 1N hydrochloric acid, and the product which has precipitated is filtered off with suction and dried in a vacuum drying oven.

Yield: 29.79 g (92% of theory) of a white solid of m.p. 227° C.

The compounds described in Table 5 were prepared analogously.

TABLE 5

(Ia) structure: phenyl ring with OH, X, Y, Z_n substituents, attached to cyclic diketone with A, B linker.

| Ex. No. | X | Y | Z_n | A | B | mp. °C. |
|---|---|---|---|---|---|---|
| Ia-2 | Cl | Cl | H | $-(CH_2)_2-CH(OCH_3)-(CH_2)_2-$ | | 220 |
| Ia-3 | $CH_3$ | $CH_3$ | H | $-(CH_2)_2-CH(OCH_3)-(CH_2)_2-$ | | 179 |
| Ia-4 | $CH_3$ | $CH_3$ | 6-$CH_3$ | $-(CH_2)_2-CH(OCH_3)-(CH_2)_2-$ | | 220–222 |
| Ia-5 | $CH_3$ | $CH_3$ | 6-$CH_3$ | $-CH_2-$(methylcyclohexyl) | | 140–145 |
| Ia-6 | $CH_3$ | $CH_3$ | 6-$CH_3$ | $-CH_2-$, $-CH_2-$ (cyclohexane-1,2-diyl) | | 204–205 |
| Ia-7 | $CH_3$ | $CH_3$ | 6-$CH_3$ | $-CH_2-$(methylcyclopentenyl) | | 217 (Z) |
| Ia-8 | $CH_3$ | $CH_3$ | H | $-CH_2-$(methylcyclopentyl) | | 210 |
| Ia-9 | $CH_3$ | $CH_3$ | 6-$CH_3$ | $-CH_2-$(cyclopentyl) | | >230 |
| Ia-4 trans | $CH_3$ | $CH_3$ | 6-$CH_3$ | $-(CH_2)_2-CH(OCH_3)-(CH_2)_2-$ | | 187 |
| Ia-4 cis | $CH_3$ | $CH_3$ | 6-$CH_3$ | $-(CH_2)_2-CH(OCH_3)-(CH_2)_2-$ | | >250 |
| Ia-10 | $CH_3$ | $CH_3$ | 6-$CH_3$ | $-(CH_2)_2-CH(OC_2H_5)-(CH_2)_2-$ | | Oil |
| Ia-11 | Cl | Cl | H | $-(CH_2)_2-CH(OC_2H_5)-(CH_2)_2-$ | | 204–210 |
| Ia-12 | $CH_3$ | $CH_3$ | H | $-(CH_2)_2-CH(OC_2H_5)-(CH_2)_2-$ | | 172–182 |
| Ia-13 | $CH_3$ | $CH_3$ | 6-$CH_3$ | $-(CH_2)_2-CH(O-n-C_3H_7)-(CH_2)_2-$ | | 172–175 |
| Ia-14 | $CH_3$ | $CH_3$ | 6-$CH_3$ | $-(CH_2)_2-CH(O-n-C_4H_9)-(CH_2)_2$ | | Oil |
| Ia-15 | $CH_3$ | t-$C_4H_9$ | H | $-(CH_2)_2-CH(OCH_3)-(CH_2)_2-$ | | 150–165 |
| Ia-16 | $CH_3$ | t-$C_4H_9$ | 6-$CH_3$ | $-(CH_2)-CH(OCH_3)_2-(CH_2)_2$ | | 206–210 |
| Ia-17 | $CH_3$ | $CH_3$ | 6-$CH_3$ | $-(CH_2)_2-$, $-CH_2-$ (cyclopentane-1,2-diyl) | | 218–220 |
| Ia-18 | Cl | Cl | H | $-(CH_2)_2-$, $-CH_2-$ (cyclopentane-1,2-diyl) | | 223 |

TABLE 5-continued

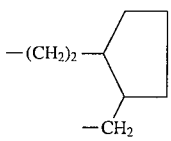

(Ia)

| Ex. No. | X | Y | $Z_n$ | A | B | mp. °C. |
|---|---|---|---|---|---|---|
| Ia-19 | $CH_3$ | $CH_3$ | H | | $-(CH_2)_2-$ cyclopentyl $-CH_2$ | 240–242 |
| Ia-20 | $CH_3$ | $CH_3$ | 6-$CH_3$ | $-CH_2-CH(SCH_3)-(CH_2)_3-$ | | 245–247 |
| Ia-21 | $CH_3$ | $CH_3$ | 6-$CH_3$ | $-CH(OCH_3)-(CH_2)_4-$ | | Oil |
| Ia-22 | $CH_3$ | $CH_3$ | 6-$CH_3$ | $-(CH_2)_2-CH(CO_2C_2H_5)-(CH_2)_2-$ | | 165–180 |
| Ia-23 | $CH_3$ | $CH_3$ | 6-$CH_3$ | $-(CH_2)_2-CH(CO_2H)-(CH_2)_2-$ | | >250 |

EXAMPLE Ib-1

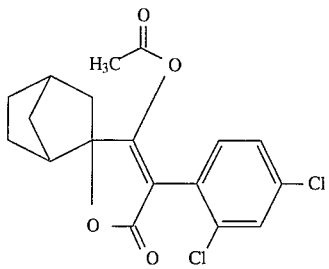

3.25 g (10 mmol) of the compound Ia-1 are introduced into 40 ml of absolute methylene chloride, 1.42 g (14 mmol) of triethylamine and a spatula-tip of DMAP were added, a solution of 0.94 g (12 mmol) of acetyl chloride in 20 ml of methylene chloride was added dropwise, and the mixture was stirred for 16 hours at room temperature.

For working-up, the reaction mixture is washed using aqueous citric acid, $NaHCO_3$ solution and NaCl solution, dried and evaporated in a rotary evaporator. Further purification is carried out by flash chromatography on silica gel using cyclohexane/ethyl acetate 3:1.

Yield: 1.70 g (46% of theory) of a solid of m.p. 126° C.

The compounds listed in Table 6 were prepared analogously.

TABLE 6

(Ib)

| Ex. No. | X | Y | $Z_n$ | A | B | $R^1$ | m.p.. °C. |
|---|---|---|---|---|---|---|---|
| Ib-2 | Cl | Cl | H | | $-(CH_2)_2-CH(OCH_3)-(CH_2)_2-$ | $-CH_3$ | Oil |
| Ib-3 | Cl | Cl | H | | $-(CH_2)_2-CH(OCH_3)-(CH_2)_2-$ | $-t-C_4H_9$ | Oil |
| Ib-4 | $CH_3$ | $CH_3$ | H | | $-(CH_2)_2-CH(OCH_3)-(CH_2)_2-$ | $-CH_3$ | Oil |
| Ib-5 | $CH_3$ | $CH_3$ | H | | $-(CH_2)_2-CH(OCH_3)-(CH_2)_2-$ | $-t-C_4H_9$ | 134 |
| Ib-6 | $CH_3$ | $CH_3$ | 6-$CH_3$ | | $-(CH_2)_2-CH(OCH_3)-(CH_2)_2-$ | $-CH_3$ | Oil |
| Ib-7 | $CH_3$ | $CH_3$ | 6-$CH_3$ | | $-(CH_2)_2-CH(OCH_3)-(CH_2)_2-$ | $-i-C_3H_7$ | Oil |
| Ib-8 | $CH_3$ | $CH_3$ | 6-$CH_3$ | | $-(CH_2)_2-CH(OCH_3)-(CH_2)_2-$ | $-t-C_4H_9$ | 78–80 |
| Ib-9 | $CH_3$ | $CH_3$ | 6-$CH_3$ | | $-(CH_2)_2-CH(OCH_3)-(CH_2)_2-$ | $-C-(CH_3)_2-CH_2Cl$ | 113–115 |
| Ib-10 | $CH_3$ | $CH_3$ | 6-$CH_3$ | | $-(CH_2)_2-CH(OCH_3)-(CH_2)_2-$ | $-CCH_3(CH_2Cl)_2$ | 118–120 |
| Ib-11 | $CH_3$ | $CH_3$ | 6-$CH_3$ | | $-(CH_2)_2-CH(OCH_3)-(CH_2)_2-$ | $-CCH_3(CH_2OCH_3)_2$ | 103–104 |

TABLE 6-continued (Ib)

| Ex. No. | X | Y | $Z_n$ | A B | $R^1$ | m.p. °C. |
|---|---|---|---|---|---|---|
| Ib-12 | $CH_3$ | $CH_3$ | 6-$CH_3$ | —$(CH_2)_2$—$CH(OCH_3)$—$(CH_2)_2$— | 1-methylcyclohexyl | 106–107 |
| Ib-13 | $CH_3$ | $CH_3$ | 6-$CH_3$ | —$(CH_2)_2$—$CH(OCH_3)$—$(CH_2)_2$— | —$C_2H_5$ | Oil |
| Ib-14 | $CH_3$ | $CH_3$ | 6-$CH_3$ | —$(CH_2)_2$—$CH(OCH_3)$—$(CH_2)_2$— | —CH($C_4H_9$)($C_2H_5$) | Oil |
| Ib-15 | $CH_3$ | $CH_3$ | 6-$CH_3$ | —$(CH_2)_2$—$CH(OCH_3)$—$(CH_2)_2$— | —$C(CH_3)_2C_2H_5$ | 107–108 |
| Ib-16 | $CH_3$ | $CH_3$ | 6-$CH_3$ | —$(CH_2)_2$—$CH(OCH_3)$—$(CH_2)_2$— | —$C(CH_3)_2$i-$C_3H_7$ | 94–96 |
| Ib-17 | $CH_3$ | $CH_3$ | 6-$CH_3$ | —$(CH_2)_2$—$CH(OCH_3)$—$(CH_2)_2$— | cyclopropyl | Oil |
| Ib-18 | $CH_3$ | $CH_3$ | 6-$CH_3$ | —$(CH_2)_2$—$CH(OCH_3)$—$(CH_2)_2$— | 1-chlorocyclopropyl | Oil |
| Ib-19 | $CH_3$ | $CH_3$ | 6-$CH_3$ | —$(CH_2)_2$—$CH(OCH_3)$—$(CH_2)_2$— | adamantyl | 200–202 |
| Ib-20 | $CH_3$ | $CH_3$ | 6-$CH_3$ | —$(CH_2)_2$—$CH(OCH_3)$—$(CH_2)_2$— | —$CH_2$-t-$C_4H_9$ | 126–129 |
| Ib-21 | $CH_3$ | $CH_3$ | 6-$CH_3$ | —$(CH_2)_2$—$CH(OCH_3)$—$(CH_2)_2$— | —$C_6H_5$ | Oil |
| Ib-22 | $CH_3$ | $CH_3$ | 6-$CH_3$ | —$(CH_2)_2$—$CH(OCH_3)$—$(CH_2)_2$— | —CH=$C(CH_3)_2$ | 107–108 |
| Ib-23 | $CH_3$ | $CH_3$ | 6-$CH_3$ | —$(CH_2)_2$—$CH(OCH_3)$—$(CH_2)_2$— | —$CH_2$-(2,4,6-trimethylphenyl) | Oil |
| Ib-24 | $CH_3$ | $CH_3$ | 6-$CH_3$ | —$CH_2$-(2-methylcyclohexyl) | t-$C_4H_9$ | Oil |
| Ib-25 | $CH_3$ | $CH_3$ | 6-$CH_3$ | —$CH_2$-cyclohexyl-$CH_2$— | —$CH_3$ | 76–78 |
| Ib-26 | $CH_3$ | $CH_3$ | 6-$CH_3$ | —$CH_2$-cyclohexyl-$CH_2$— | -i-$C_3H_7$ | Oil |
| Ib-27 | $CH_3$ | $CH_3$ | 6-$CH_3$ | —$CH_2$-cyclohexyl-$CH_2$— | -t-$C_4H_9$ | 114–116 |

TABLE 6-continued (Ib)

| Ex. No. | X | Y | $Z_n$ | A | B | $R^1$ | m.p. °C. |
|---|---|---|---|---|---|---|---|
| Ib-28 | $CH_3$ | $CH_3$ | 6-$CH_3$ | —$CH_2$ | cyclopentenyl | —$CH_3$ | 188–189 |
| Ib-29 | $CH_3$ | $CH_3$ | 6-$CH_3$ | —$CH_2$ | cyclopentenyl | -t-$C_4H_9$ | 131 |
| Ib-30 | Cl | Cl | H | —$CH_2$ | cyclopentyl | -t-$C_4H_9$ | 112 |
| Ib-31 | $CH_3$ | $CH_3$ | H | —$CH_2$ | cyclopentyl | —$CH_3$ | 105 |
| Ib-32 | $CH_3$ | $CH_3$ | H | —$CH_2$ | cyclopentyl | t-$C_4H_9$ | Oil |
| Ib-33 | $CH_3$ | $CH_3$ | 6-$CH_3$ | —$CH_2$ | cyclopentyl | —$CH_3$ | 159 |
| Ib-34 | $CH_3$ | $CH_3$ | 6-$CH_3$ | —$CH_2$ | cyclopentyl | -i-$C_3H_7$ | 104 |
| Ib-35 | $CH_3$ | $CH_3$ | 6-$CH_3$ | —$CH_2$ | cyclohexyl | -t-$C_4H_9$ | 102–103 |
| Ib-36 | $CH_3$ | $CH_3$ | 6-$CH_3$ | —$CH_2$ | cyclopentyl | —$C(CH_3)_2$—$CH_2Cl$ | 111 |
| Ib-37 | $CH_3$ | $CH_3$ | 6-$CH_3$ | —$CH_2$ | cyclopentyl | —$C(CH_2Cl)_2CH_3$ | 136 |

TABLE 6-continued

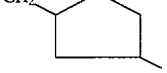

(Ib)

| Ex. No. | X | Y | $Z_n$ | A | B | $R^1$ | m.p. °C. |
|---|---|---|---|---|---|---|---|
| Ib-38 | $CH_3$ | $CH_3$ | 6-$CH_3$ | —$CH_2$ | 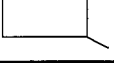 | —$C(CH_2—O—CH_3)_2CH_3$ | 119 |
| Ib-39 | $CH_3$ | $CH_3$ | 6-$CH_3$ | —$CH_2$ | 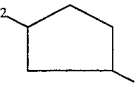 | —$C(CH_3)_2$—$C_2H_5$ | 105 |

| Ex. No. | X | Y | $Z_n$ | A | B | $R^1$ | m.p. °C. |
|---|---|---|---|---|---|---|---|
| Ib-40 | $CH_3$ | $CH_3$ | 6-$CH_3$ | —$CH_2$ |  | —$C(CH_3)_2$-i-$C_3H_7$ | 138 |
| Ib-41 | $CH_3$ | $CH_3$ | 6-$CH_3$ | —$CH_2$ | 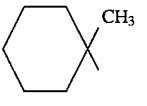 | 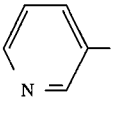 | 119 |
| Ib-43 | $CH_3$ | $CH_3$ | 6-$CH_3$ | —$(CH_2)_2$—$CH(OCH_3)$—$(CH_2)_2$— | | $Cl(CH_2)_3$— | Oil |
| Ib-44 | $CH_3$ | $CH_3$ | 6-$CH_3$ | —$(CH_2)_2$—$CH(OCH_3)$—$(CH_2)_2$— | | 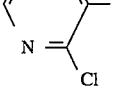 | 120 |
| Ib-45 | $CH_3$ | $CH_3$ | 6-$CH_3$ | —$(CH_2)_2$—$CH(OCH_3)$—$(CH_2)_2$— | | 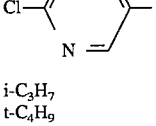 | Oil |
| Ib-46 | $CH_3$ | $CH_3$ | 6-$CH_3$ | —$(CH_2)_2$—$CH(OCH_3)$—$(CH_2)_2$— | | 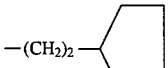 | Oil |
| Ib-47 | $CH_3$ | $CH_3$ | 6-$CH_3$ | —$(CH_2)_2$—$CH(OC_2H_5)$—$(CH_2)_2$— | | i-$C_3H_7$ | 130–134 |
| Ib-48 | $CH_3$ | $CH_3$ | 6-$CH_3$ | —$(CH_2)_2$—$CH(OC_2H_5)$—$(CH_2)_2$— | | t-$C_4H_9$ | 133–135 |
| Ib-49 | Cl | Cl | H | —$(CH_2)_2$—$CH(OC_2H_5)$—$(CH_2)_2$— | | t-$C_4H_9$ | Oil |
| Ib-50 | $CH_3$ | $CH_3$ | H | —$(CH_2)_2$—$CH(OC_2H_5)$—$(CH_2)_2$— | | t-$C_4H_9$ | 127 |
| Ib-51 | $CH_3$ | $CH_3$ | 6-$CH_3$ | —$(CH_2)_2$—$CH(OC_3H_7)$—$(CH_2)_2$— | | t-$C_4H_9$ | 127–130 |
| Ib-52 | $CH_3$ | $CH_3$ | 6-$CH_3$ | —$(CH_2)_2$—$CH(OC_4H_9)$—$(CH_2)_2$— | | t-$C_4H_9$ | 140 |
| Ib-53 | $CH_3$ | t-$C_4H_9$ | H | —$(CH_2)_2$—$CH(OCH_3)$—$(CH_2)_2$— | | t-$C_4H_9$ | 160 |
| Ib-54 | $CH_3$ | t-$C_4H_9$ | 6-$CH_3$ | —$(CH_2)_2$—$CH(OCH_3)$—$(CH_2)_2$— | | t-$C_4H_9$ | 188–190 |
| Ib-55 | $CH_3$ | $CH_3$ | 6-$CH_3$ | —$(CH_2)_2$ —$CH_2$ | | t-$C_3H_7$ | 114–116 |

-continued

| Ex. No. | X | Y | $Z_n$ | A B | $R^1$ | m.p. °C. |
|---|---|---|---|---|---|---|
| Ib-56 | $CH_3$ | $CH_3$ | 6-$CH_3$ | —(CH$_2$)$_2$—⟨cyclopentyl⟩—CH$_2$— | $t$-$C_4H_9$ | 116–118 |
| Ib-57 | Cl | Cl | H | —(CH$_2$)$_2$—⟨cyclopentyl⟩—CH$_2$— | $t$-$C_4H_9$ | 123–125 |
| Ib-58 | $CH_3$ | $CH_3$ | H | —(CH$_2$)$_2$—⟨cyclopentyl⟩—CH$_2$— | $t$-$C_4H_9$ | Oil |
| Ib-59 | $CH_3$ | $CH_3$ | 6-$CH_3$ | —$CH_2$—$CH(SCH_3)$—$(CH_2)_3$— | $i$-$C_3H_7$ | 136–137 |
| Ib-60 | $CH_3$ | $CH_3$ | 6-$CH_3$ | —$CH_2$—$CH(SCH_3)$—$(CH_2)_3$— | $t$-$C_4H_9$ | 120–121 |
| Ib-61 | $CH_3$ | $CH_3$ | 6-$CH_3$ | —$CH(OCH_3)$—$(CH_2)_4$— | $i$-$C_3H_7$ | Oil |
| Ib-62 | $CH_3$ | $CH_3$ | 6-$CH_3$ | —$CH(OCH_3)$—$(CH_2)_4$— | $t$-$C_4H_9$ | Oil |
| Ib-63 | $CH_3$ | $CH_3$ | 6-$CH_3$ | —$(CH_2)_2$—$CH(CO_2C_2H_5)$—$(CH_2)_2$ | $t$-$C_4H_9$ | Oil |

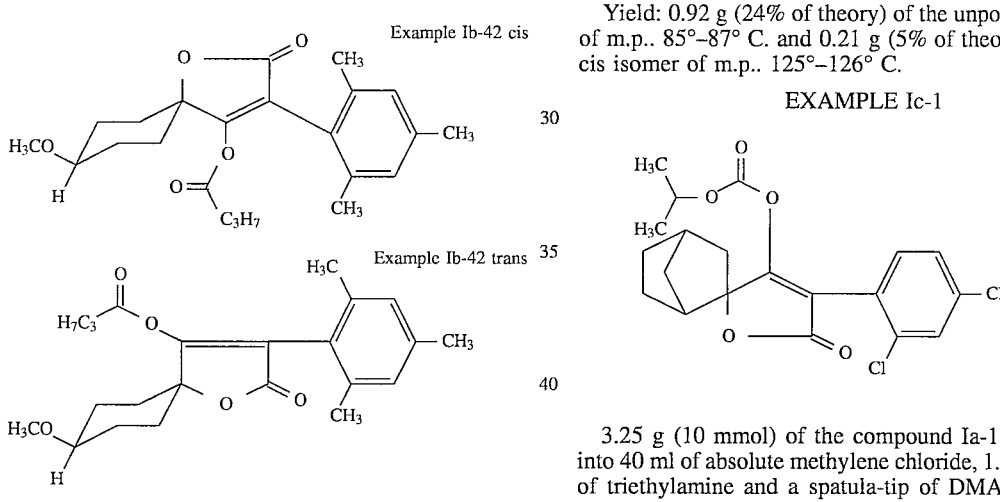

Example Ib-42 cis

Example Ib-42 trans 3.16 g (10 mmol) of the compound Ia-4 are introduced into 40 ml of absolute methylene chloride, 1.42 g (14 mmol) of triethylamine and a spatula-tip of DMAP is added, a solution of 1.38 g (13 mmol) of butyryl chloride in 20 ml of methylene chloride is added dropwise, and the mixture is stirred for 16 hours at room temperature.

For working-up, the reaction mixture is washed using aqueous citric acid, NaHCO$_3$ solution and NaCl solution, dried and evaporated in a rotary evaporator. Separation into the isomers is carried out by flash chromatography on silica gel using cyclohexane/ethyl acetate 6:1.

Yield: 0.92 g (24% of theory) of the unpolar trans isomer of m.p.. 85°–87° C. and 0.21 g (5% of theory) of the polar cis isomer of m.p.. 125°–126° C.

EXAMPLE Ic-1

3.25 g (10 mmol) of the compound Ia-1 are introduced into 40 ml of absolute methylene chloride, 1.42 g (14 mmol) of triethylamine and a spatula-tip of DMAP are added, a solution of 1.47 g (12 mmol) of isopropyl chloroformate in 20 ml of methylene chloride is added dropwise, and the mixture is stirred for 16 hours at room temperature.

For working-up, the reaction mixture is washed using aqueous citric acid, NaHCO$_3$ solution and NaCl solution, dried and evaporated in a rotary evaporator. Further purification is carried out by recrystallization from MTB ether/n-hexane.

Yield: 2.84 g (69% of theory) of a solid of m.p.. 136° C.

The compounds listed in Table 7 were prepared analogously:

TABLE 7

(Ic)

| Ex. No. | X | Y | $Z_n$ | A | B | L | M | $R^2$ | m.p. °C. |
|---|---|---|---|---|---|---|---|---|---|
| Ic-2 | Cl | Cl | H | $-(CH_2)_2-CH(OCH_3)-(CH_2)_2-$ | | O | O | -i-$C_3H_7$ | 100 |
| Ic-3 | $CH_3$ | $CH_3$ | H | $-(CH_2)_2-CH(OCH_3)-(CH_2)_2-$ | | O | O | i-$C_3H_7$ | Oil |
| Ic-4 | $CH_3$ | $CH_3$ | 6-$CH_3$ | $-(CH_2)_2-CH(OCH_3)-(CH_2)_2-$ | | O | O | $-CH_3$ | Oil |
| Ic-5 | $CH_3$ | $CH_3$ | 6-$CH_3$ | $-(CH_2)_2-CH(OCH_3)-(CH_2)_2-$ | | O | O | -i-$C_3H_7$ | Oil |
| Ic-6 | $CH_3$ | $CH_3$ | 6-$CH_3$ | $-(CH_2)_2-CH(OCH_3)-(CH_2)_2-$ | | O | O | -i-$C_4H_9$ | Oil |
| Ic-7 | $CH_3$ | $CH_3$ | 6-$CH_3$ | $-(CH_3)_2-CH(OCH_3)-(CH_2)_2-$ | | O | O | -s-$C_4H_9$ | Oil |
| Ic-8 | $CH_3$ | $CH_3$ | 6-$CH_3$ | $-(CH_2)_2-CH(OCH_3)-(CH_2)_2-$ | | O | O | $-C_2H_5$ | Oil |
| Ic-9 | $CH_3$ | $CH_3$ | 6-$CH_3$ | $-(CH_2)_2-CH(OCH_3)-(CH_2)_2-$ | | O | O | -t-$C_4H_9$ | 120–130 |
| Ic-10 | $CH_3$ | $CH_3$ | 6-$CH_3$ | $-(CH_2)-CH(OCH_3)-(CH_2)_2-$ | | O | O | $-C_6H_5$ | Oil |
| Ic-11 | $CH_3$ | $CH_3$ | 6-$CH_3$ | $-(CH_2)_2-CH(OCH_3)-(CH_2)_2-$ | | O | O | $-CH_2-CH(C_4H_9)C_2H_5$ | Oil |
| Ic-12 | $CH_3$ | $CH_3$ | 6-$CH_3$ | $-(CH_2)_2-CH(OCH_3)-(CH_2)_2-$ | | O | O | $-CH(CH_3)-CH_2-O-C_3H_7$ | Oil |
| Ic-13 | $CH_3$ | $CH_3$ | 6-$CH_3$ | $-(CH_2)_2-CH(OCH_3)-(CH_2)_2-$ | | O | S | -i-$C_3H_7$ | 131–140 |
| Ic-14 | $CH_3$ | $CH_3$ | 6-$CH_3$ | $-CH_2-$(cyclohexane-1,2-diyl)$-CH_2-$ | | O | O | -i-$C_3H_7$ | 87–89 |
| Ic-15 | $CH_3$ | $CH_3$ | H | $-CH_2-$(cyclopentane-1,3-diyl) | | O | O | -i-$C_3H_7$ | 84 |
| Ic-16 | $CH_3$ | $CH_3$ | 6-$CH_3$ | $-CH_2-$(cyclopentane-1,3-diyl) | | O | O | -i-$C_3H_7$ | 73 |
| Ic-17 | $CH_3$ | $CH_3$ | 6-$CH_3$ | $-CH_2-$(cyclopentane-1,3-diyl) | | O | O | -i-$C_4H_9$ | Oil |
| Ic-18 | $CH_3$ | $CH_3$ | 6-$CH_3$ | $-(CH_2)_2-CH(OC_2H_5)-(CH_2)_2-$ | | O | O | $C_2H_5$ | Oil |
| Ic-19 | $CH_3$ | $CH_3$ | 6-$CH_3$ | $-(CH_2)_2-CH(OC_2H_5)-(CH_2)_2-$ | | O | O | i-$C_3H_7$ | Oil |
| Ic-20 | Cl | Cl | H | $-(CH_2)_2-CH(OC_2H_5)-(CH_2)_2-$ | | O | O | i-$C_3H_7$ | Oil |
| Ic-21 | $CH_3$ | $CH_3$ | H | $-(CH_2)_2-CH(OC_2H_5)-(CH_2)_2-$ | | O | O | i-$C_3H_7$ | Oil |
| Ic-22 | $CH_3$ | $CH_3$ | 6-$CH_3$ | $-(CH_2)_2-CH(OC_4H_9)-(CH_2)_2-$ | | O | O | i-$C_3H_7$ | Oil |
| Ic-23 | $CH_3$ | t-$C_4H_9$ | H | $-(CH_2)_2-CH(OCH_3)-(CH_2)_2-$ | | O | O | i-$C_3H_7$ | Oil |
| Ic-24 | $CH_3$ | $CH_3$ | 6-$CH_3$ | $-(CH_2)_2-CH(OCH_3)-(CH_2)_2-$ | | O | S | t-$C_4H_9$ | Oil |

TABLE 7-continued (Ic)

[Structure: biphenyl compound with L, O, M—R², A, B, X, Y, Z_n substituents and lactone O=C-O group]

| Ex. No. | X | Y | $Z_n$ | A | B | L | M | $R^2$ | m.p. °C. |
|---|---|---|---|---|---|---|---|---|---|
| Ic-25 | $CH_3$ | $CH_3$ | 6-$CH_3$ | | $-(CH_2)_2-$ [cyclopentane] $-CH_2$ | O | O | $C_2H_5$ | Oil |
| Ic-26 | $CH_3$ | $CH_3$ | 6-$CH_3$ | | $-(CH_2)_2-$ [cyclopentane] $-CH_2$ | O | O | i-$C_3H_7$ | Oil |
| Ic-27 | Cl | Cl | H | | $-(CH_2)_2-$ [cyclopentane] $-CH_2$ | O | O | i-$C_3H_7$ | 106–108 |
| Ic-28 | $CH_3$ | $CH_3$ | H | | $-(CH_2)_2-$ [cyclopentane] $-CH_2$ | O | O | i-$C_3H_7$ | 134–136 |
| Ic-29 | $CH_3$ | $CH_3$ | 6-$CH_3$ | | $-CH_2-CH(SCH_3)-(CH_2)_3-$ | O | O | $C_2H_5$ | 99–101 |
| Ic-30 | $CH_3$ | $CH_3$ | 6-$CH_3$ | | $-CH_2-CH(SCH_3)-(CH_2)_3-$ | O | O | i-$C_3H_7$ | 128–129 |
| Ic-31 | $CH_3$ | $CH_3$ | 6-$CH_3$ | | $-CH(OCH_3)-(CH_2)_4-$ | O | O | $C_2H_5$ | Oil |
| Ic-32 | $CH_3$ | $CH_3$ | 6-$CH_3$ | | $-CH(OCH_3)-(CH_2)_4-$ | O | O | i-$C_3H_7$ | 111–112 |
| Ic-33 | $CH_3$ | $CH_3$ | 6-$CH_3$ | | $-(CH_2)_2-CH(CO_2C_2H_5)-(CH_2)_2-$ | O | O | i-$C_3H_7$ | Oil |

EXAMPLE 1d-1

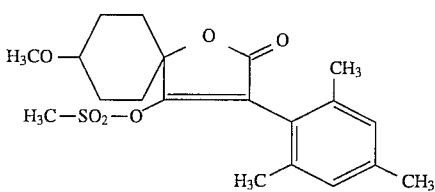

To 3.16 g (10 mmol) of enole Ia-4 in 40 ml of absolute $CH_2Cl_2$ are first added 1.52 g (15 mmol) of triethylamine and then at 0°–10° C. a solution of 1.48 g (13 mmol) $CH_3SO_2Cl$ in 10 ml $CH_2Cl_2$ are added dropwise.

The mixture is stirred for 2 hours at room temperature, then washed with aqueous citric acid (10%) and $NaHCO_3$ solution, dried and evaporated.

The crude product is then mixed with 20 ml of petrol ether, suction filtered and dried.

Yield: 2.40 g of a solid (61% of theory), m.p. 130°–155° C.

The compounds listed in Table 8 were prepared analogously.

TABLE 8

(Id)

Structure: O—SO₂—R³ with substituents

| Ex. No. | X | Y | $Z_n$ | A B | R³ | m.p. °C. |
|---|---|---|---|---|---|---|
| Id-2 | $CH_3$ | $CH_3$ | 6-$CH_3$ | —$(CH_2)_2$—CH(OCH$_3$)—$(CH_2)_2$— | $H_3C$—⟨phenyl⟩— | 115–132 |

EXAMPLE Ie-1

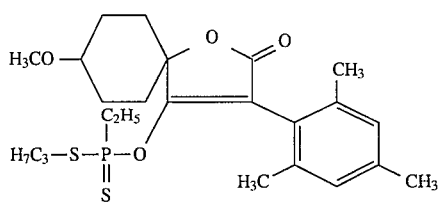

To a solution of 2.2 g of example No. Ia-4 in 10 ml of tetrahydrofuran are added 1.1 ml of triethylamine and then 1.42 g (0.007 mol) of ethanethiophosphonic acid propylthioether. The mixture is stirred for 3 hours at 50° C., evaporated and the residue is chromatographed over silica gel using hexane/ethyl acetate/acetone 30/10/1 as eluent. 2.1 g (62% of theory) of the compound shown are obtained as viscous oil (mixture of isomers).

$^1$H-NMR (300 MHz, CDCl$_3$): δ=2.19, 2.20, 2.25, 2.26, (4s, 9H, Phenyl-CH$_3$), 3.15–3.25, 3.57 (2m, 1H, CH—OCH$_3$), 3.33, 3.39 (2s, 3H, OCH$_3$), 6.87 (s, 2H, Phenyl-H)ppm $^{31}$P-NMR (162 MHz, CDCl$_3$): δ=119.05, 119.64 ppm.

The compounds listed in Table 9 are prepared analogously.

TABLE 9

(Ie)

| Ex. No. | X | Y | $Z_n$ | A B | L | R⁴ | R⁵ | NMR δ (ppm) |
|---|---|---|---|---|---|---|---|---|
| Ie-2 cis | $CH_3$ | $CH_3$ | 6-$CH_3$ | —$(CH_2)_2$—CH(OCH$_3$)—$(CH_2)_2$— | S | $C_2H_5$ | s-$C_4H_9$—S— | 3.39 (s, 3H, O$\underline{CH_3}$), 3.15–3.2 (m, 1H—$\underline{CH}$OCH$_3$) |
| Ie-2 trans | $CH_3$ | $CH_3$ | 6-$CH_3$ | —$(CH_2)_2$—CH(OCH$_3$)—$(CH_2)_2$— | S | $C_2H_5$ | s-$C_4H_9$—S— | 3.32 (s, 3H, O$\underline{CH_3}$), 3.57 (m, 1H, $\underline{CH}$—OCH$_3$) |
| Ie-3 cis | $CH_3$ | $CH_3$ | 6-$CH_3$ | —$(CH_2)_2$—CH(OCH$_3$)—$(CH_2)_2$— | S | $CH_3$ | $H_7C_3$—S— | 3.9 (s, 3H, O$\underline{CH_3}$) 3.18–3.23 (m, 1H, $\underline{CH}$OCH$_3$) |
| Ie-3 trans | $CH_3$ | $CH_3$ | 6-$CH_3$ | —$(CH_2)_2$—CH(OCH$_3$)—$(CH_2)_2$— | S | $CH_3$ | $H_7C_3$—S— | 3.33 (s, 3H, O$\underline{CH_3}$), 3.57 (m, 1H, $\underline{CH}$OCH$_3$), 6.87, 6.89 (s, 2H, Ar—$\underline{H}$) |

EXAMPLE II-1

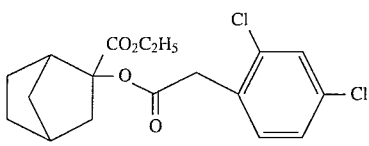

EXAMPLE II-2

18.40 g (0.10 mol) of ethyl 2-hydroxy-norbornane-2-carboxylate and 24.59 g (0.11 mol) of 2,4-dichlorophenylacetyl chloride are refluxed for 16 hours in 100 ml of absolute toluene and the mixture is evaporated in a rotary evaporator. The compound shown above is obtained in a yield of 37.10 g (quantitatively) in the form of an oil.

The compounds listed in Table 10 were prepared analogously.

TABLE 10

$$\text{(II)}$$

| Ex. No. | X | Y | $Z_n$ | A | B | $R^8$ | m.p. °C. |
|---|---|---|---|---|---|---|---|
| II-2 | Cl | Cl | H | $-(CH_2)_2-CH(OCH_3)-(CH_2)_2-$ | | $C_2H_5$ | Oil |
| II-3 | $CH_3$ | $CH_3$ | H | $-(CH_2)_2-CH(OCH_3)-(CH_2)_2-$ | | $C_2H_5$ | Oil |
| II-4 | $CH_3$ | $CH_3$ | 6-$CH_3$ | $-(CH_2)_2-CH(OCH_3)-(CH_2)_2-$ | | $C_2H_5$ | Oil |
| II-5 | $CH_3$ | $CH_3$ | 6-$CH_3$ | $-CH_2-$cyclohexyl | | $C_2H_5$ | Oil |
| II-6 | $CH_3$ | $CH_3$ | 6-$CH_3$ | $-CH_2-$cyclohexyl-$CH_2-$ | | $C_2H_5$ | Oil |
| II-7 | $CH_3$ | $CH_3$ | 6-$CH_3$ | $-CH_2-$cyclopentenyl | | $C_2H_5$ | Oil |
| II-8 | $CH_3$ | $CH_3$ | H | $-CH_2-$cyclopentyl | | $C_2H_5$ | Oil |
| II-9 | $CH_3$ | $CH_3$ | 6-$CH_3$ | $-CH_2-$cyclopentyl | | $C_2H_5$ | Oil |
| II-10 | $CH_3$ | $CH_3$ | 6-$CH_3$ | $-(CH_2)_2-CH(OC_2H_5)-(CH_2)_2-$ | | $C_2H_5$ | Oil |
| II-11 | Cl | Cl | H | $-(CH_2)_2-CH(OC_2H_5)-(CH_2)_2-$ | | $C_2H_5$ | Oil |
| II-12 | $CH_3$ | $CH_3$ | H | $-(CH_2)_2-CH(OC_2H_5)-(CH_2)_2-$ | | $C_2H_5$ | Oil |
| II-13 | $CH_3$ | $CH_3$ | 6-$CH_3$ | $-(CH_2)_2-CH(O-n-C_3H_7)-(CH_2)_2-$ | | $C_2H_5$ | Oil |
| II-14 | $CH_3$ | $CH_3$ | 6-$CH_3$ | $-(CH_2)_2-CH(O-n-C_4H_9)-(CH_2)_2-$ | | $C_2H_5$ | Oil |

TABLE 10-continued

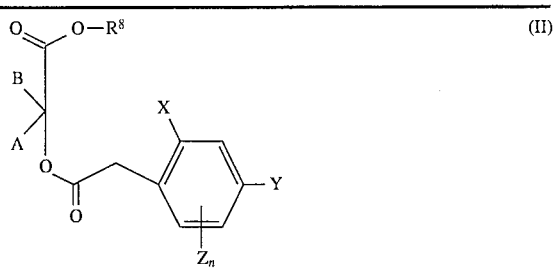

(II)

| Ex. No. | X | Y | $Z_n$ | A | B | $R^8$ | m.p. °C. |
|---|---|---|---|---|---|---|---|
| II-15 | $CH_3$ | $t\text{-}C_4H_9$ | H | \multicolumn{2}{l\|}{$-(CH_2)_2-CH(OCH_3)-(CH_2)_2-$} | $C_2H_5$ | Oil |
| II-16 | $CH_3$ | $t\text{-}C_4H_9$ | 6-$CH_3$ | \multicolumn{2}{l\|}{$-(CH_2)_2-CH(OCH_3)-(CH_2)_2-$} | $C_2H_5$ | Oil |
| II-17 | $CH_3$ | $CH_3$ | 6-$CH_3$ | \multicolumn{2}{l\|}{$-(CH_2)_2-$ cyclopentyl $-CH_2$} | $C_2H_5$ | Oil |
| II-18 | Cl | Cl | H | \multicolumn{2}{l\|}{$-(CH_2)_2-$ cyclopentyl $-CH_2$} | $C_2H_5$ | Oil |
| II-19 | $CH_3$ | $CH_3$ | H | \multicolumn{2}{l\|}{$-(CH_2)_2-$ cyclopentyl $-CH_2$} | $C_2H_5$ | Oil |
| II-20 | $CH_3$ | $CH_3$ | 6-$CH_3$ | \multicolumn{2}{l\|}{$-CH_2-CH_2(SCH_3)-(CH_2)_3-$} | $C_2H_5$ | Oil |
| II-21 | $CH_3$ | $CH_3$ | 6-$CH_3$ | \multicolumn{2}{l\|}{$-CH(OCH_3)-(CH_2)_4-$} | $C_2H_5$ | Oil |
| II-22 | $CH_3$ | $CH_3$ | 6-$CH_3$ | \multicolumn{2}{l\|}{$-(CH_2)_2-CH(CO_2C_2H_5)-(CH_2)_2-$} | $C_2H_5$ | Oil |
| II-23 | $CH_3$ | $CH_3$ | 6-$CH_3$ | \multicolumn{2}{l\|}{$-(CH_2)_2-CH(CO_2H)-(CH_2)_2-$} | $C_2H_5$ | Oil |

We claim:

1. 3-Aryl-4-hydroxy-$\Delta^3$-dihydrofuranone derivatives of the general formula (I)

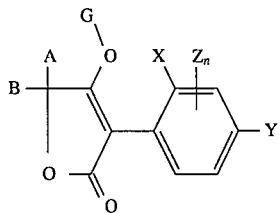

(I)

in which

X represents alkyl, halogen, alkoxy or halogenoalkyl,

Y represents hydrogen, alkyl, halogen, alkoxy or halogenoalkyl,

Z represents alkyl, halogen or alkoxy, n represents a number from 0–3, or in which the radicals X and Z together with the phenyl radical to which they are bonded form the naphthalene radical of the formula

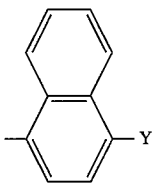

in which Y has the abovementioned meaning,

G represents hydrogen (a) or the groups

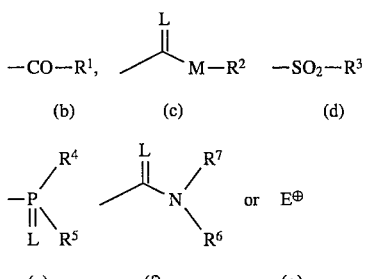

A and B together with the carbon atom to which they are bonded form a cycle which is substituted by alkoxy, alkylthio, alkylsulphoxyl, alkylsulphonyl, carboxyl or $CO_2R^2$ or A and B together with the carbon atom to which they are bonded represent a cycle in which two substituents together with the carbon atoms to which they are bonded represent a saturated cycle which is optionally substituted by alkyl, alkoxy or halogen and which can be interrupted by oxygen or sulphur, $E^{\oplus}$ represents a metal ion equivalent or an ammonium ion, L and M represent in each case oxygen or sulphur, $R^1$ represents in each case optionally substituted alkyl, alkenyl, alkoxyalkyl, alkylthioalkyl, polyalkoxyalkyl or cycloalkyl which can be interrupted by at least one hetero atom, in each case optionally substituted phenyl, phenylalkyl, hetaryl, phenoxyalkyl or hetaryloxyalkyl and $R^2$ represents alkyl, cycloalkyl, alkenyl, alkoxyalkyl or polyalkoxyalkyl, each of which is optionally substituted or represents in each case optionally substituted phenyl or benzyl, $R^3$, $R^4$ and $R^5$ independently of one another represent alkyl, alkoxy, alkylamino, dialkylamino, alkylthio, alkenylthio, alkinylthio or cycloalkylthio, each of which is optionally substituted by halogen, and in each case optionally substituted phenyl, phenoxy or phenylthio, $R^6$ and $R^7$ independently of one another represent hydrogen, or represent alkyl, alkenyl, alkoxy or alkoxyalkyl, each of which is optionally substituted by halogen, optionally substituted phenyl, optionally substituted benzyl, or in which $R^6$ and $R^7$ together represent an alkylene radical which is optionally interrupted by oxygen or sulphur, and the stereomerically and enantiomerically pure forms and their mixtures.

2. Process for the preparation of 3-aryl-4-hydroxy-$\Delta^3$-dihydrofuranone derivatives of the formula I according to claim 1 characterized in that (A) to prepare compounds of the formula Ia

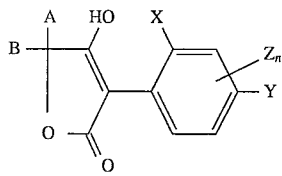

in which

A, B, X, Y, Z and n have the abovementioned meaning, carboxylic esters of the formula (II)

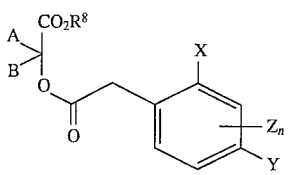

in which

A, B, X, Y, Z and n have the abovementioned meaning and $R^8$ represents alkyl, are subjected to an intramolecular condensation reaction in the presence of a diluent and in the presence of a base, or (B) to prepare compounds of the formula (Ib)

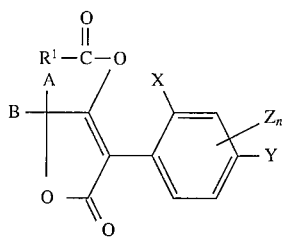

in which

A, B, X, Y, Z, $R^1$ and n have the abovementioned meaning, compounds of the formula (Ia)

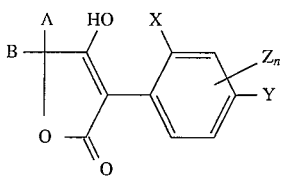

in which

A, B, X, Y, Z and n have the abovementioned meaning,

α) are reacted with acid halides of the general formula (III)

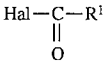

in which $R^1$ has the abovementioned meaning and

Hal represents halogen, if appropriate in the presence of a diluent and if appropriate in the presence of an acid-binding agent, or β) are reacted with carboxylic anhydrides of the general formula (IV)

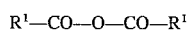

in which $R^1$ has the abovementioned meaning if appropriate in the presence of a diluent and if appropriate in the presence of an acid-binding agent, or (C) to prepare compounds of the formula (Ic)

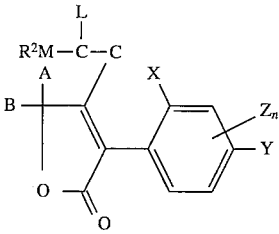

in which

A, B, X, Y, Z, $R^2$ and n have the abovementioned meaning

L represents oxygen and

M represents oxygen or sulphur, compounds of the formula (Ia)

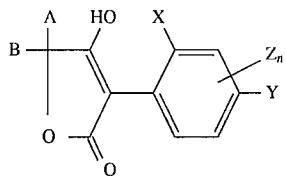

in which

A, B, X, Y, Z and n have the abovementioned meaning are reacted with chloroformic esters or chloroformic thioesters of the general formula (V)

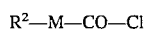

in which $R^2$ and M have the abovementioned meaning, if appropriate in the presence of a diluent and if appropriate in the presence of an acid-binding agent, or (D)

to prepare compounds of the formula (Ic)

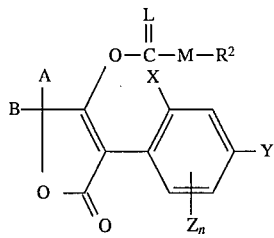

in which

A, B, $R^2$, X, Y, Z and n have the abovementioned meaning,

L represents sulphur and

M represents oxygen or sulphur, compounds of the formula (Ia)

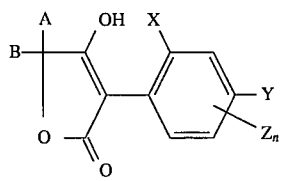

in which

A, B, X, Y, Z and n have the abovementioned meaning are reacted with chloromonothioformic esters or chlorodithioformic esters of the general formula (VI)

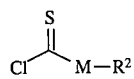

in which

M and $R^2$ have the abovementioned meaning,
if appropriate in the presence of a diluent and if appropriate in the presence of an acid-binding agent, or (E)

to prepare compounds of the formula (Id)

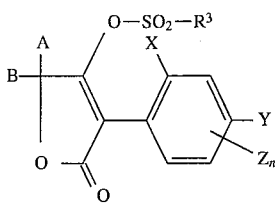

in which

A, B, X, Y, Z, $R^3$ and n have the abovementioned meaning, compounds of the formula (Ia)

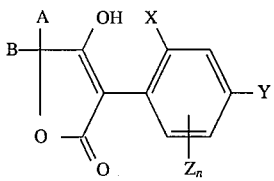

in which

A, B, X, Y, Z and n have the abovementioned meaning, are reacted with sulphonyl chlorides of the general formula (VII)

$$R^3\!-\!SO_2\!-\!Cl \qquad (VII)$$

in which $R^3$ has the abovementioned meaning,
if appropriate in the presence of a diluent and if appropriate in the presence of an acid-binding agent,
or (F)

to prepare compounds of the formula (Ie)

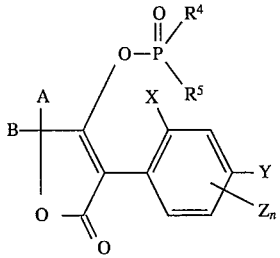

in which

A, B, L, X, Y, Z, $R^4$, $R^5$ and n have the abovementioned meaning, compounds of the formula (Ia)

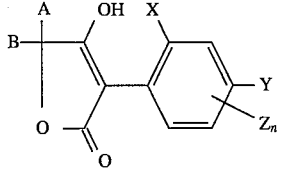

in which

A, B, X, Y, Z and n have the abovementioned meaning are reacted with phosphorus compounds of the general formula (IX)

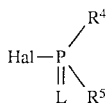

in which

L, $R^4$ and $R^5$ have the abovementioned meaning and

Hal represents halogen, if appropriate in the presence of a diluent and if appropriate in the presence of an acid-binding agent, or (G)

to prepare compounds of the formula (If)

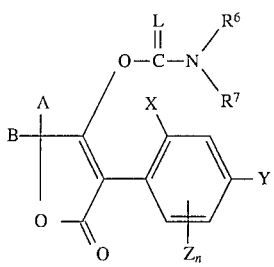

in which

A, B, L, X, Y, Z, $R^6$, $R^7$ and n have the abovementioned meaning, compounds of the formula (Ia),

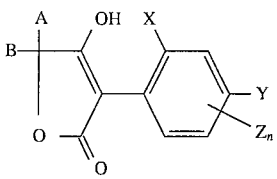

in which

A, B, X, Y, Z and n have the abovementioned meaning,

α) are reacted with isocyanates of the general formula (IX)

in which

L and $R^6$ have the abovementioned meaning, if appropriate in the presence of a diluent and if appropriate in the presence of a catalyst, or β) are reacted with carbamoyl chlorides or thiocarbamoyl chlorides of the general formula (X)

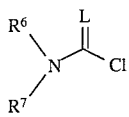

in which

L, $R^6$ and $R^7$ have the abovementioned meaning, if appropriate in the presence of a diluent and if appropriate in the presence of an acid-binding agent, or (H)

to prepare compounds of the formula (Ig)

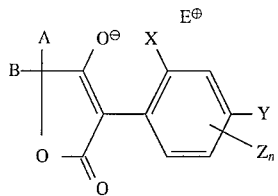

in which

X, Y, Z, A, B and n have the abovementioned meaning, and $E^{\oplus}$ represents a metal ion equivalent or an ammonium ion, compounds of the formula (Ia)

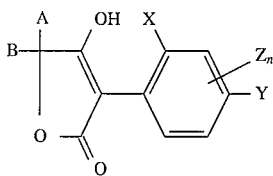

in which

X, Y, Z, A, B and n have the abovementioned meaning, are reacted with metal compounds or amines of the general formulae (XI) and (XII)

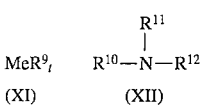

in which

Me represents mono- or divalent metal ions, t represents the number 1 or 2, $R^9$ represents hydrogen, hydroxy or alkoxy and $R^{10}$, $R^{11}$ and $R^{12}$ independently of one another represent hydrogen or alkyl, if appropriate in the presence of a diluent.

3. 3-Aryl-4-hydroxy-$\Delta^3$-dihydrofuranone derivatives of the general formula (I) according to claim 1 which, taking into consideration the various meanings of (a), (b), (c), (d), (e), (f) and (g) of group G have the following structures (Ia) to (Ig):

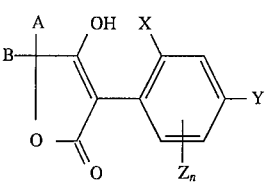

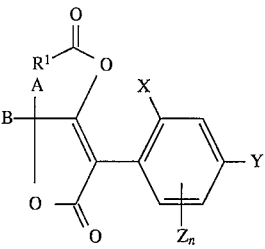

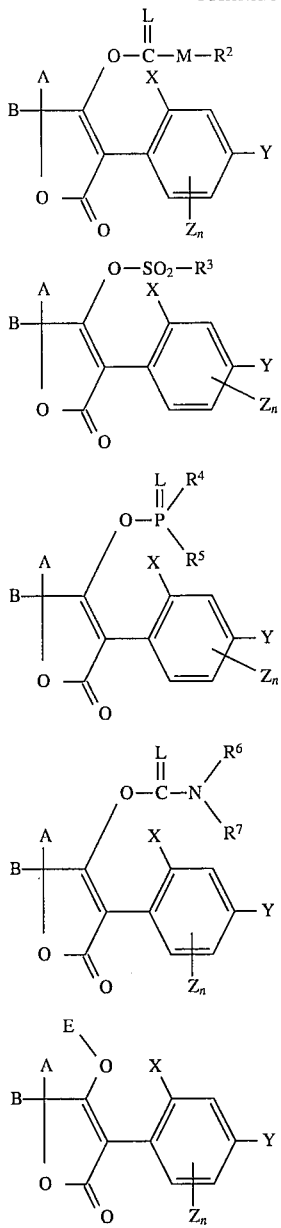

in which

A, B, E, L, M, X, Y, $Z_n$, $R^1$, $R^2$, $R^3$, $R^4$, $R^5$, $R^6$ and $R^7$ have the meaning given in claim 1.

4. 3-Aryl-4-hydroxy-$\Delta^3$-dihydrofuranone derivatives of the general formula (I) according to claim 1, in which X represents $C_1$–$C_6$-alkyl, halogen, $C_1$–$C_6$-alkoxy or $C_1$–$C_3$-halogenoalkyl, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number from 0 to 3, or in which the radicals X and Z together with the phenyl radical to which they are bonded form the naphthalene radical of the formula (Ic)

in which Y has the abovementioned meaning,
or in which

A and B together with the carbon atom to which they are bonded form a saturated or unsaturated 3- to 8-membered ring which is substituted by $C_1$–$C_6$-alkoxy, $C_1$–$C_4$-alkylthio, $C_1$–$C_4$-alkylsulphoxyl or $C_1$–$C_4$-alkylsulphonyl, carboxyl or $CO_2R^2$ or A and B together with the carbon atom to which they are bonded represent a $C_3$–$C_8$-membered ring in which two substituents together with the carbon atoms to which they are bonded represent a saturated $C_5$–$C_7$-ring which is optionally substituted by $C_1$–$C_6$-alkyl, $C_1$–$C_6$-alkoxy or halogen and which can be interrupted by oxygen or sulphur, G represents hydrogen (a) or the groups $-CO-R^1$, (b)  $\overset{L}{\underset{}{=}}M-R^2$ (c)  $-SO_2-R^3$ (d)

$-\overset{L}{\underset{L}{P}}\overset{R^4}{\underset{R^5}{}}$ (e)  $\overset{L}{\underset{}{=}}N\overset{R^7}{\underset{R^6}{}}$ (f)  or $E^\oplus$ (g)

in which $E^\oplus$ represents a metal ion equivalent or an ammonium ion,

L and M in each case represent oxygen or sulphur, $R^1$ represents optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_1$–$C_8$-alkyl or $C_3$–$C_8$-cycloalkyl, which is optionally substituted by halogen or $C_1$–$C_6$-alkyl and which can be interrupted by at east one oxygen and/or sulphur atom, phenyl which is optionally substituted by halogen, nitro, $C_1$–$C_6$-alkyl, $C_1$–$C_6$-alkoxy, $C_1$–$C_6$-halogenoalkyl or $C_1$–$C_6$-halogenoalkoxy;

phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy hetaryl which is optionally substituted by halogen and/or $C_1$–$C_6$-alkyl, phenoxy-$C_1$–$C_6$-alkyl which is optionally substituted by halogen and/or $C_1$–$C_6$-alkyl, hetaryloxy-$C_1$–$C_6$-alkyl which is optionally substituted by halogen, amino and/or $C_1$–$C_6$-alkyl, $R^2$ represents $C_1$–$C_{20}$-alkyl, $C_3$–$C_{20}$-alkenyl, $C_1$–$C_8$-alkoxy-$C_2$–$C_8$-alkyl or $C_1$–$C_8$-polyalkoxy-$C_2$–$C_8$-alkyl, each of which is optionally substituted by halogen, $C_3$–$C_8$-cycloalkyl, which is optionally substituted by halogen or $C_1$–$C_6$-alkyl, phenyl or benzyl, each of which is optionally substituted by halogen, nitro, $C_1$–$C_6$-alkyl, $C_1$–$C_6$-alkoxy or $C_1$–$C_6$-halogenoalkyl, R³, R⁴ and R⁵ independently of one another represent optionally halogen-substituted $C_1$–$C_8$-alkyl, $C_1$–$C_8$-alkoxy, $C_1$–$C_8$-alkylamino, di-($C_1$–$C_8$)-alkylamino, $C_1$–$C_8$)-alkylthio, $C_2$–$C_5$-alkenylthio, $C_2$–$C_5$-alkinylthio or $C_3$–$C_7$-cycloalkylthio, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, R⁶ and R⁷ independently of one another represent hydrogen or represent $C_1$–$C_{20}$-alkyl, $C_1$–$C_{20}$-alkoxy, $C_3$–$C_8$-alkenyl or $C_1$–$C_{20}$-alkoxy-$C_1$–$C_{20}$-alkyl, each of which is optionally substituted by halogen, phenyl which is optionally substituted by halogen, $C_1$–$C_{20}$-halogenoalkyl, $C_1$–$C_{20}$-alkyl or $C_1$–$C_{20}$-alkoxy, benzyl which is optionally substituted by halogen, $C_1$–$C_{20}$-alkyl, $C_1$–$C_{20}$-halogenoalkyl or $C_1$–$C_{20}$-alkoxy, or together represent a $C_4$–$C_6$-alkylene ring which is optionally interrupted by oxygen or sulphur, and the stereomerically and enantiomerically pure forms of these compounds and their mixtures.

5. 3-Aryl-4-hydroxy-$\Delta^3$-dihydrofuranone derivatives of the formula (I) according to claim 1, in which X represents $C_1$–$C_6$-alkyl, halogen, $C_1$–$C_6$-alkoxy or $C_1$–$C_2$-halogenoalkyl, Y represents hydrogen, $C_1$–$C_6$-alkyl, halogen, $C_1$–$C_6$-alkoxy or $C_1$–$C_2$-halogenoalkyl, Z represents $C_1$–$C_4$-alkyl, halogen or $C_1$–$C_4$-alkoxy, n represents a number from 0 to 2, or in which the radicals X and Z together with the phenyl radical to which they are bonded form the naphthalene radical of the formula

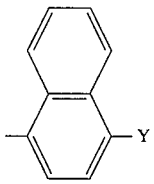

in which Y has the abovementioned meaning,

A and B together with the carbon atom to which they are bonded form a saturated or unsaturated, 5- to 7-membered ring which is substituted by $C_1$–$C_5$-alkoxy, $C_1$–$C_3$-alkylthio, $C_1$–$C_3$-alkylsulphoxyl, $C_1$–$C_3$-alkylsulphonyl, carboxyl or $CO_2R^2$ or A and B together with the carbon atom to which they are bonded represent a $C_4$–$C_7$-membered ring in which two substituents together with the carbon atoms to which they are bonded represent a saturated $C_5$–$C_6$-ring which is optionally substituted by $C_1$–$C_3$-alkyl, $C_1$–$C_3$-alkoxy, fluorine or chlorine and which can be interrupted by oxygen or sulphur, G represents hydrogen (a) or the groups

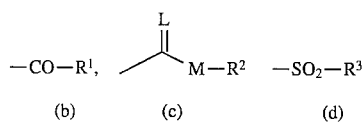

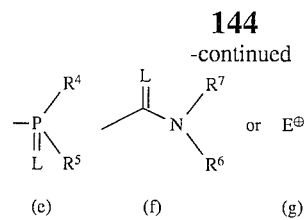

in which $E^\oplus$ represents a metal ion equivalent or an ammonium ion,

L and M in each case represent oxygen or sulphur,

R¹ represents in each case optionally halogen-substituted $C_1$–$C_{16}$-alkyl, $C_2$–$C_{16}$-alkenyl, $C_1$–$C_6$-alkoxy-$C_1$–$C_6$-alkyl, $C_1$–$C_{16}$-alkylthio-$C_1$–$C_6$-alkyl, $C_1$–$C_6$-polyalkoxy-$C_1$–$C_6$-alkyl or $C_3$–$C_7$-cycloalkyl, which is optionally substituted by chlorine or $C_1$–$C_4$-alkyl and which can be interrupted by 1–2 oxygen and/or sulphur atoms phenyl which is optionally substituted by halogen, nitro, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl, or $C_1$–$C_3$-halogenoalkoxy, or represents furanyl, thienyl, pyridyl, pyrimidyl, thiazolyl or pyrazolyl each of which is optionally substituted by halogen and/or $C_1$–$C_6$-alkyl, phenoxy-$C_1$–$C_5$-alkyl which is optionally substituted by halogen and/or $C_1$–$C_4$-alkyl, pyridyloxy-$C_1$–$C_5$-alkyl, pyrimidyloxyl-$C_1$–$C_5$-alkyl or thiazolyloxy-$C_1$–$C_5$-alkyl, each of which is optionally substituted by halogen, amino and/or $C_1$–$C_4$-alkyl, R² represents optionally halogen-substituted: $C_1$–$C_6$-alkyl, $C_3$–$C_6$-alkenyl, $C_1$–$C_6$-alkoxy-$C_2$–$C_6$-alkyl or $C_1$–$C_6$-polyalkoxy-$C_2$–$C_6$-alkyl, or represents $C_3$–$C_7$-cycloalkyl, which is optionally substituted by fluorine, chlorine or $C_1$–$C_4$-alkyl, phenyl or benzyl, each of which is optionally substituted by halogen, nitro, $C_1$–$C_4$-alkyl, $C_1$–$C_3$-alkoxy or $C_1$–$C_3$-halogenoalkyl, R³, R⁴ and R⁵ independently of one another represent $C_{1-C6}$-alkyl, $C_1$–$C_6$-alkoxy, $C_1$–$C_6$-alkylamino, di($C_1$–$C_6$)-alkylamino, $C_1$–$C_6$-alkylthio, $C_3$–$C_6$-alkenylthio, $C_2$–$C_4$-alkinylthio or $C_3$–$C_6$-cycloalkylthio, each of which is optionally substituted by halogen, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, R⁶ and R⁷ independently of one another represent hydrogen or represent $C_1$–$C_{20}$-alkyl, $C_1$–$C_{20}$-alkoxy, $C_3$–$C_8$-alkenyl or $C_1$–$C_{20}$-alkoxy-$C_1$–$C_{20}$-alkyl, each of which is optionally substituted by halogen, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, or together represent a $C_4$–$C_6$-alkylene ring which is optionally interrupted by oxygen or sulphur, and their stereomerically and enantiomerically pure forms and their mixtures.

6. 3-Aryl-4-hydroxy-$\Delta^3$-dihydrofuranone derivatives of the formula (I) according to claim 1, in which X represents methyl, ethyl, propyl, i-propyl, fluorine, chlorine, bromine, methoxy, ethoxy or trifluoromethyl, Y represents hydrogen, methyl, ethyl, propyl, i-propyl, butyl, i-butyl, tert-butyl, fluorine, chlorine, bromine, methoxy, ethoxy or trifluoromethyl, Z represents methyl, ethyl, i-propyl, butyl, i-butyl, tert-butyl, fluorine, chlorine, bromine, methoxy or ethoxy, n represents 0 or 1, A and B together with the carbon atom to which they are bonded form a saturated or unsaturated 5- to 6-membered ring which is substituted by $C_1$–$C_4$-alkoxy, $C_1$–$C_2$-alkylthio, $C_1$–$C_2$-alkylsulphoxyl, $C_1$–$C_2$-alkylsulphonyl, carboxyl or $CO_2R^2$ or A and B together with the carbon atom to which they are bonded represent a $C_4$–$C_6$-membered ring in which two substituents together with the carbon atoms to which they are bonded represent a saturated $C_5$–$C_6$-ring which is optionally substituted by methyl, ethyl, methoxy, ethoxy, fluorine or chlorine and which can be interrupted by oxygen or sulphur, G represents hydrogen (a) or the groups

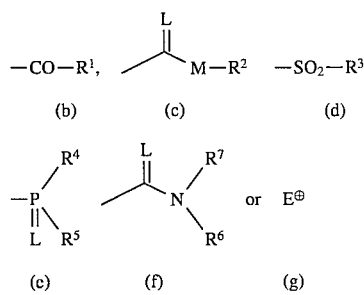

in which $E^\oplus$ represents a metal ion equivalent or an ammonium ion,

L and M in each case represent oxygen or sulphur, $R^1$ represents in each case optionally fluorine or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_1$–$C_4$-alkyl or $C_3$–$C_6$-cycloalkyl, which is optionally substituted by fluorine, chlorine, methyl or ethyl and which can be interrupted by 1–2 oxygen and/or sulphur atoms, or represents phenyl, which is optionally substituted by fluorine, chlorine, bromine, methyl, ethyl, propyl, i-propyl, methoxy, ethoxy, trifluoromethyl, trifluoromethoxy or nitro, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents furanyl, thienyl, pyridyl, pyrimidyl, thiazolyl or pyrazolyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl, $R^2$ represents $C_1$–$C_{14}$-alkyl, $C_3$–$C_{14}$-alkenyl, $C_1$–$C_4$-alkoxy-$C_2$–$C_6$-alkyl or $C_1$–$C_4$-polyalkoxy-$C_2$–$C_6$-alkyl, each of which is optionally substituted by fluorine or chlorine, or represents $C_3$–$C_6$-cycloalkyl, which is optinally substituted by fluorine, chlorine, methyl or ethyl, or represents phenyl or benzyl, each of which is optionally substituted by fluorine, chlorine, nitro, methyl, ethyl, propyl, i-propyl, methoxy, ethoxy, or trifluoromethyl, $R^3$, $R^4$ and $R^5$ independently of one another represent $C_1$–$C_4$-alkyl, $C_1$–$C_4$-alkoxy, $C_1$–$C_4$-alkylamino, di-($C_1$–$C_4$-alkyl)-amino or $C_1$–$C_4$-alkylthio, each of which is optionally substituted by fluorine or chlorine, or represents phenyl, phenoxy or phenylthio, each of which is optionally substituted by fluorine, chlorine, bromine, nitro, cyano, $C_1$–$C_2$-alkoxy, $C_1$–$C_4$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl, $R^6$ and $R^7$ independently of one another represent hydrogen or represent $C_1$–$C_{10}$-alkyl, $C_3$–$C_6$-alkenyl, $C_1$–$C_{10}$-alkoxy or $C_1$–$C_{10}$-alkoxy-$C_1$–$C_{10}$-alkyl, each of which is optionally substituted by fluorine, chlorine or bromine, or represent phenyl which is optionally substituted by fluorine, chlorine, bromine, $C_1$–$C_2$-halogenoalkyl, $C_1$–$C_2$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_4$-alkoxy, or together represent a $C_4$–$C_6$-alkylene ring which is optionally interrupted by oxygen or sulphur, and their stereomerically and enantiomerically pure forms and their mixtures.

7. Pesticides, characterized in that they contain at least one 3-aryl-4-hydroxy-$\Delta^3$-dihydrofuranone derivative of the formula (I) according to claim 1.

8. Process for the preparation of pesticides, characterized in that 3-aryl-4-hydroxy-$\Delta^3$-dihydrofuranone derivatives of the formula (I) according to claim 1 are mixed with extenders and/or surface-active agents.

9. Method of combating animal pests, characterized in that 3-aryl-4-hydroxy-$\Delta^3$-dihydro-furanone derivatives of the formula (I) according to claim 1 are applied to the pests and/or their environment.

10. A compound according to claim 1, wherein such compound is

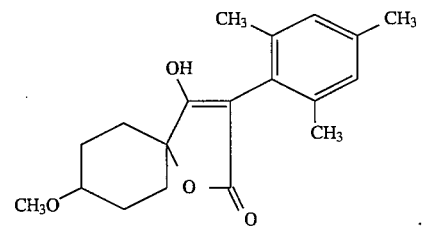

11. A compound according to claim 1, wherein such compound is

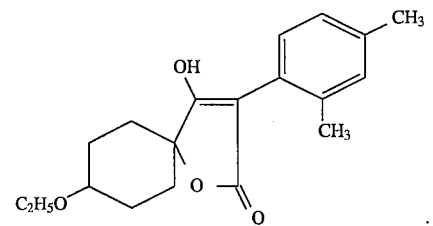

12. A compound according to claim 1, wherein such compound is
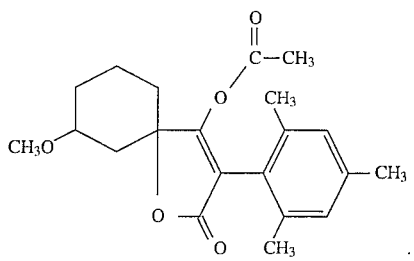
13. A compound according to claim 1, wherein such compound is
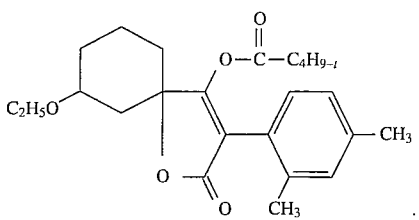
14. The method according to claim 9, wherein such compound is
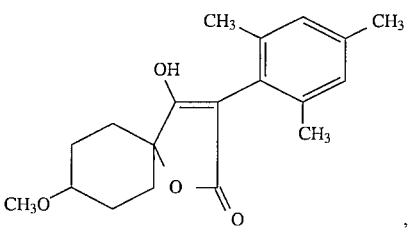,
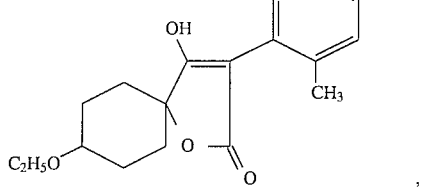,
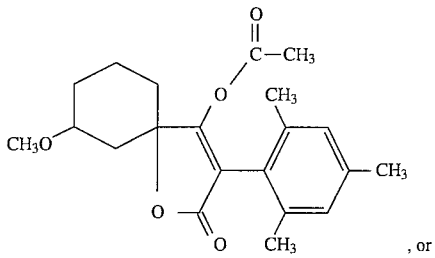, or
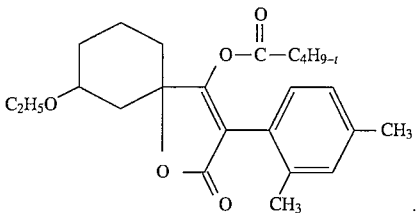
* * * * *

UNITED STATES PATENT AND TRADEMARK OFFICE
CERTIFICATE OF CORRECTION

Page 1 of 2

PATENT NO. : 5,610,122
DATED : March 11, 1997
INVENTOR(S) : Fischer, et al.

It is certified that error appears in the above-indentified patent and that said Letters Patent is hereby corrected as shown below:

Col. 138, line 45    Delete " 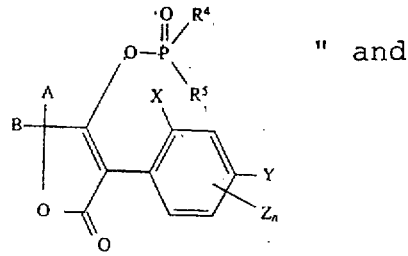 " and substitute

-- 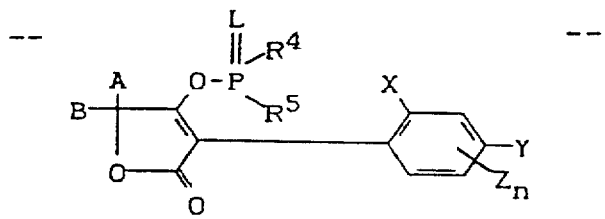 --

Col. 144, line 45    Delete " $C_1-C_6$-alkyl " and substitute -- $C_1-C_6$-alkyl --

UNITED STATES PATENT AND TRADEMARK OFFICE
CERTIFICATE OF CORRECTION

PATENT NO. : 5,610,122
DATED : March 11, 1997
INVENTOR(S) : Fischer, et al.

It is certified that error appears in the above-indentified patent and that said Letters Patent is hereby corrected as shown below:

Col. 144, line 46-47     Delete " $C_3$-$C_6$-alkenylthio " and substitute -- $C_3$-$C_4$-alkenylthio --

Signed and Sealed this

Fifteenth Day of July, 1997

Attest:

Attesting Officer

BRUCE LEHMAN

Commissioner of Patents and Trademarks